(12) United States Patent
Arumugham et al.

(10) Patent No.: US 9,089,510 B2
(45) Date of Patent: *Jul. 28, 2015

(54) A-β IMMUNOGENIC PEPTIDE CARRIER CONJUGATES AND METHODS OF PRODUCING SAME

(75) Inventors: Rasappa G. Arumugham, Chapel Hill, NC (US); A. Krishna Prasad, Chapel Hill, NC (US); Michael Hagen, Pittsford, NY (US)

(73) Assignees: Janssen Sciences Ireland UC, County Cork (IE); Wyeth LLC, New York, NY (US)

( * ) Notice: Subject to any disclaimer, the term of this patent is extended or adjusted under 35 U.S.C. 154(b) by 952 days.

This patent is subject to a terminal disclaimer.

(21) Appl. No.: 13/178,428

(22) Filed: Jul. 7, 2011

(65) Prior Publication Data

US 2011/0287042 A1    Nov. 24, 2011

Related U.S. Application Data

(60) Continuation of application No. 11/841,919, filed on Aug. 20, 2007, which is a division of application No. 10/583,503, filed as application No. PCT/US2004/044093 on Dec. 17, 2004, now Pat. No. 8,227,403.

(60) Provisional application No. 60/530,481, filed on Dec. 17, 2003.

(51) Int. Cl.
| | | |
|---|---|---|
| *A61K 38/04* | (2006.01) | |
| *C07K 7/06* | (2006.01) | |
| *C07K 17/00* | (2006.01) | |
| *G01N 33/532* | (2006.01) | |
| *A61K 39/00* | (2006.01) | |
| *A61K 47/48* | (2006.01) | |

(52) U.S. Cl.
CPC ......... *A61K 39/0007* (2013.01); *A61K 47/4833* (2013.01); *A61K 47/48284* (2013.01); *A61K 2039/6031* (2013.01); *A61K 2039/6081* (2013.01); *A61K 2039/62* (2013.01)

(58) Field of Classification Search
None
See application file for complete search history.

(56) References Cited

U.S. PATENT DOCUMENTS

| | | | |
|---|---|---|---|
| 4,882,317 A | | 11/1989 | Marburg et al. |
| 5,126,131 A | | 6/1992 | Dintzis et al. |
| 5,245,015 A | | 9/1993 | Fung et al. |
| 5,360,897 A | * | 11/1994 | Anderson et al. ............. 530/403 |
| 5,623,057 A | | 4/1997 | Marburg et al. |
| 5,723,127 A | | 3/1998 | Scott et al. |
| 5,866,129 A | | 2/1999 | Chang et al. |
| 5,877,220 A | | 3/1999 | Schwartz et al. |
| 6,645,503 B1 | | 11/2003 | Arumugham et al. |
| 6,710,226 B1 | | 3/2004 | Schenk |
| 6,743,427 B1 | | 6/2004 | Schenk |
| 6,750,324 B1 | | 6/2004 | Schenk et al. |
| 6,761,888 B1 | | 7/2004 | Schenk |
| 6,787,138 B1 | | 9/2004 | Schenk |
| 6,787,139 B1 | | 9/2004 | Schenk |
| 6,787,140 B1 | | 9/2004 | Schenk |
| 6,787,143 B1 | | 9/2004 | Schenk |
| 6,787,144 B1 | | 9/2004 | Schenk |
| 6,787,523 B1 | | 9/2004 | Schenk |
| 6,787,637 B1 | | 9/2004 | Schenk |
| 6,808,712 B2 | | 10/2004 | Schenk |
| 6,818,218 B2 | | 11/2004 | Schenk |
| 6,866,849 B2 | | 3/2005 | Schenk |
| 6,866,850 B2 | | 3/2005 | Schenk |
| 6,875,434 B1 | | 4/2005 | Schenk |
| 6,890,535 B1 | | 5/2005 | Schenk |
| 6,905,686 B1 | | 6/2005 | Schenk |
| 6,946,135 B2 | | 9/2005 | Schenk |
| 6,962,707 B2 | | 11/2005 | Schenk |
| 6,962,984 B2 | | 11/2005 | Ishiwata et al. |
| 6,972,127 B2 | | 12/2005 | Schenk |
| 6,982,084 B2 | | 1/2006 | Schenk |
| 7,014,855 B2 | | 3/2006 | Schenk |
| 7,575,880 B1 | | 8/2009 | Schenk et al. |
| 7,588,766 B1 | | 9/2009 | Schenk |

(Continued)

FOREIGN PATENT DOCUMENTS

| | | |
|---|---|---|
| CN | 1456353 A | 3/2003 |
| EP | 0 941 738 A1 | 9/1999 |

(Continued)

OTHER PUBLICATIONS

U.S. Appl. No. 11/841,993, filed Aug. 20, 2007, Arumugham et al.
U.S. Appl. No. 11/841,950, filed Aug. 20, 2007, Arumugham et al.
U.S. Appl. No. 11/841,897, filed Aug. 20, 2007, Arumugham et al.
U.S. Appl. No. 11/841,882, filed Aug. 20, 2007, Arumugham et al.
U.S. Appl. No. 11/841,849, filed Aug. 20, 2007, Arumugham et al.
U.S. Appl. No. 60/530,481, filed Dec. 17, 2003, Arumugham et al.
U.S. Appl. No. 60/530,480, filed Dec. 17, 2003, Arumugham et al.
Supplementary European Search Report dated Aug. 23, 2007 for application EP04814839.9.

(Continued)

*Primary Examiner* — Satyanarayana R Gudibande
(74) *Attorney, Agent, or Firm* — Alston & Bird LLP

(57) ABSTRACT

The present invention is directed to methods of producing conjugates of Aβ peptide immunogens with protein/polypeptide carrier molecules, which are useful as immunogens, wherein peptide immunogens are conjugated to protein carriers via activated functional groups on amino acid residues of the carrier or of the optionally attached linker molecule, and wherein any unconjugated reactive functional groups on amino acid residues are inactivated via capping, thus retaining the immunological functionality of the carrier molecule, but reducing the propensity for undesirable reactions that could render the conjugate less safe or effective. Furthermore, the invention also relates to such immunogenic products and immunogenic compositions containing such immunogenic products made by such methods.

21 Claims, 10 Drawing Sheets

(56) References Cited

U.S. PATENT DOCUMENTS

| | | | |
|---|---|---|---|
| 8,227,403 B2 | 7/2012 | Arumugham et al. | |
| 2002/0086847 A1 | 7/2002 | Chain | |
| 2003/0092145 A1 | 5/2003 | Jira et al. | |
| 2003/0135035 A1 | 7/2003 | Shannon | |
| 2003/0166558 A1 | 9/2003 | Frangione et al. | |
| 2003/0190322 A1 | 10/2003 | Kaastrup | |
| 2003/0207828 A1 | 11/2003 | Ishiwata et al. | |
| 2003/0224011 A1* | 12/2003 | Conley et al. | 424/189.1 |
| 2004/0081657 A1 | 4/2004 | Schenk | |
| 2004/0219146 A1 | 11/2004 | Schenk | |
| 2004/0247590 A1 | 12/2004 | Schenk et al. | |
| 2004/0265301 A1 | 12/2004 | Schenk et al. | |
| 2004/0265308 A1 | 12/2004 | Schenk | |
| 2005/0013815 A1 | 1/2005 | Schenk | |
| 2005/0019328 A1 | 1/2005 | Schenk et al. | |
| 2005/0019330 A1 | 1/2005 | Schenk et al. | |
| 2005/0048049 A1 | 3/2005 | Schenk | |
| 2005/0059591 A1 | 3/2005 | Schenk et al. | |
| 2005/0059802 A1 | 3/2005 | Schenk et al. | |
| 2005/0142132 A1 | 6/2005 | Schenk et al. | |
| 2005/0158304 A1 | 7/2005 | Schenk et al. | |
| 2005/0163788 A1 | 7/2005 | Schenk | |
| 2005/0191292 A1 | 9/2005 | Schenk | |
| 2005/0191314 A1 | 9/2005 | Schenk | |
| 2005/0196399 A1 | 9/2005 | Schenk | |
| 2005/0249727 A1 | 11/2005 | Schenk | |
| 2005/0255122 A1 | 11/2005 | Schenk | |
| 2006/0029611 A1 | 2/2006 | Schenk | |
| 2006/0034858 A1 | 2/2006 | Schenk | |
| 2006/0135403 A1 | 6/2006 | Gervais et al. | |
| 2007/0134762 A1 | 6/2007 | Arumugham et al. | |
| 2007/0161088 A1 | 7/2007 | Arumugham et al. | |
| 2008/0096818 A1 | 4/2008 | Schenk et al. | |
| 2008/0145373 A1 | 6/2008 | Arumugham et al. | |
| 2008/0227718 A1 | 9/2008 | Schenk et al. | |
| 2008/0227719 A1 | 9/2008 | Schenk et al. | |
| 2008/0299074 A1 | 12/2008 | Arumugham et al. | |
| 2009/0191231 A1 | 7/2009 | Schenk et al. | |
| 2009/0297511 A1 | 12/2009 | Schenk | |
| 2010/0207706 A1 | 8/2010 | Tamura et al. | |
| 2011/0287042 A1 | 11/2011 | Arumugham et al. | |
| 2012/0207706 A1 | 8/2012 | Arumugham et al. | |

FOREIGN PATENT DOCUMENTS

| | | |
|---|---|---|
| EP | 1 321 466 A1 | 6/2006 |
| GB | 2 333 706 A | 8/1999 |
| WO | WO 93/15760 A1 | 8/1993 |
| WO | WO 99/27944 A1 | 6/1999 |
| WO | WO 00/50077 A1 | 8/2000 |
| WO | WO 00/72880 * | 12/2000 |
| WO | WO 00/72880 A2 | 12/2000 |
| WO | WO 01/30390 A2 | 5/2001 |
| WO | WO 01/62284 A2 | 8/2001 |
| WO | WO 01/62284 A3 | 8/2001 |
| WO | WO 01/90182 A2 | 11/2001 |
| WO | WO 01/93804 A2 | 12/2001 |
| WO | WO 02/38177 A2 | 5/2002 |
| WO | WO 02/38177 A3 | 5/2002 |
| WO | WO 02/096350 A2 | 12/2002 |
| WO | WO 03/092619 A2 | 11/2003 |
| WO | WO 2004/080490 A2 | 9/2004 |
| WO | WO 2004/083251 A2 | 9/2004 |
| WO | WO 2005/027836 A2 | 3/2005 |
| WO | WO 2005/027836 A3 | 3/2005 |
| WO | WO 2005/058940 A2 | 6/2005 |
| WO | WO 2005/058940 A3 | 6/2005 |
| WO | WO 2005/058941 A2 | 6/2005 |
| WO | WO 2005/058941 A3 | 6/2005 |

OTHER PUBLICATIONS

Ecuador Patent Application No. SP 06-6655, English translation of Opposition Brief filed Mar. 16, 2007 by Asociacion de Laboratories Farmaceuticos (ALAFAR).

Ecuador Patent Application No. SP 06-6646, English translation of Opposition Brief submitted Mar. 16, 2007 by Asociacion de Laboratories Farmaceuticos (ALAFAR).

Extended European Search Report dated Jun. 29, 2011 for application EP11151428.7.

Holmes et al., "Long-term Effects of Aβ42 Immunisation in Alzheimer's Disease: Follow-up of a Randomised, Placebo-controlled Phase I Trial." Lancet. 372: 216-223 (2008).

Hyslop et al., "Will Anti-amyloid Therapies Work for Alzheimer's Disease?," Lancet, 372:180-182 (2008).

PCT International Preliminary Report on Patentability (Chapter I) of Sep. 13, 2006 with Written Opinion mailed Aug. 4, 2006 for application PCT/US04/42701.

PCT International Preliminary Report on Patentability (Chapter II) of Jul. 24, 2006 for application PCT/US04/44093.

PCT Written Opinion of Mar. 16, 2006 mailed Apr. 6, 2006 for application PCT/US04/44093.

Bernard et al., "A New Method of Preparing Hapten-Carrier Immungens by Coupling with *Saccharomyces cerevvisiae* by Periodate Oxidation," *Journal of Immunological Methods*, 61:351-357 (1983).

Gearing et al., "The Effect of Primary Immunization and Concanavalin A o the Production of Monoclonal Natural Antibodies," *Hyridoma*, 5(3):243-247 (1986).

Hansen et al., "Photochemical Conjugation of Peptides to Carrier Proteins Using 1,2,3-thiadiazole-4carboxylic acid," *Int. J. Peptide Protein Res.*, 47:419-426 (1996).

Peeters et al., "Comparison of Four Bifunctional Reagents for Coupling Peptides to Proteins and the Effect of the Three Moieties on the Immuno gencity of the Conjugates," *Journal of Immunological Methods*, 120:133-143 (1989).

Shimizu et al., "Isoaspartate Formation at Position 23 of Amyloid Beta Peptide Enhanced Fibril Formation and Deposited Onto Senile Plaques and Vascular Amyloids in Alzheimer's Disease," *Journal of Neuroscience Research*, 70:451-461 (2002).

Bard et al., "Epitope and Isotype Specificities of Antibodies to β-amyloid Peptide for Protection Against Alzheimer's Disease-like Neuropathology," PNAS, 100(4): 2023-2028 (2003).

Tam et al., "Synthetic Peptide Vaccine Design: Synthesis and Properties of High-Density Multiple Antigenic Peptide System," *Biochemistry*, 85:5409-5413 (1988).

Mariotti et al., "Immunogenicity of anti-Haemophilus Influenzae Tybe b $CRM_{197}$ Conjugate Following Mucosal Vaccination with Oligodeoxynucleotide Containing Immunostimulatory Sequences as Adjuvant," *Vaccine*, 20:2229-2239 (2002).

Brunswick et al., "Picogram Quantities of Anti-Ig Antibodies Coupled to Dextran Induce B Cell Proliferation," The Journal of Immunology, 140(10):3364-3372 (1988).

G.T. Hermanson, "Bioconjugate Techniques," Academic Press, pp. 514-515 (1996).

Supplementary European Search Report dated Aug. 31, 2009 for application EP 04817081.

Askelöf et al., "Protective Immunogenicity of Two Synthetic Peptides Selected From the Amino Acid Sequence of Bodetella Pertussis Toxin Subunit S1," *Microbiology*, Pro. Natl. Acad. Sci., 87:1347-1351 (1990).

Brinkley, "A Brief Survey of Methods for Preparing Protein Conjugates with Dyes, Haptens, and Cross-Linking Reagents," *Bioconjugate Chem*. 3:2-13 (1992).

Restriction Requirement for U.S. Appl. No. 11/841,919, mailed Dec. 10, 2010.

Non-final Office Action for U.S. Appl. No. 11/841,919, mailed Mar. 28, 2011.

Non-final Office Action for U.S. Appl. No. 11/841,993, mailed Jul. 13, 2009.

Final Office Action for U.S. Appl. No. 11/841,993, mailed Jan. 27, 2010.

Restriction Requirement for U.S. Appl. No. 10/583,503, mailed Jan. 6, 2009.

Non-final Office Action for U.S. Appl. No. 10/583,503, mailed May 19, 2010.

Final Office Action for U.S. Appl. No. 10/583,503, mailed Jan. 28, 2011.

(56) References Cited

OTHER PUBLICATIONS

Joyce, et al. Isolation, structural characterization, and immunological evaluation of a high-molecular-weight exopolysaccharide from *Staphylococcus aureus*. Carbohydrate Research. 338:903-922 (2003).

Restriction Requirement for U.S. Appl. No. 10/583,464, mailed Apr. 6, 2009.

Non-final Office Action for U.S. Appl. No. 10/583,464, mailed Dec. 30, 2009.

Final Office Action for U.S. Appl. No. 10/583,464, mailed Oct. 6, 2010.

Advisory Action for U.S. Appl. No. 10/583,464 mailed Mar. 8, 2011.

Extended European Search Report dated Jul. 30, 2013 for application EP12157147.

Final Office Action for U.S. Appl. No. 10/583,464, mailed Aug. 8, 2013.

Monsonego et al., "Immune hyporesponsiveness to amyloid B-peptide in amyloid precursor protein transgenic mice: Implications for the pathogenesis and treatment of Alzheimer's disease" *PNAS*, Aug. 28, 2001, vol. 98, No. 18, 10273-10278.

Non-final Office Action for U.S. Appl. No. 11/841,993, mailed Feb. 5, 2014.

Sigurdsson et al., : Immunization with a Nontoxic/Nonfibrillar Amyloid-B Homologous Peptide Reduces Alzheimer's Disease Associated Pathology in Transgenic Mice *American Journal of Pathology*, Aug. 2001, vol. 159 No. 2, p. 439-447.

U.S. Appl. No. 13/396,543, filed Feb. 14, 2012, Arumugham et al.

Final Office Action for U.S. Appl. No. 11/841,919, mailed Sep. 27, 2011.

Gudmundsson, et al., "Characterisation of residues in antibody binding sites by chemical modification of surface-adsorbed protein combined wih enzyme immunoassay," *J. Immunological Methods*, 158(2): 215-227 (1993).—Abstract Only.

Non-final Office Action for U.S. Appl. No. 10/583,464, mailed Nov. 10, 2011.

Notice of Allowance for U.S. Appl. No. 10/583,503, mailed Feb. 29, 2012.

Non-final Office Action for U.S. Appl. No. 13/396,543, mailed Dec. 19, 2014.

Non-Final Office Action for U.S. Appl. No. 11/841,919, mailed Oct. 30, 2014.

Notice of Allowance for U.S. Appl. No. 11/841,919, mailed Feb. 20, 2014.

Restriction Requirement for U.S. Appl. No. 13/396,543, mailed Sep. 11, 2014.

\* cited by examiner

SEQUENCE LISTING

```
<160> NUMBER OF SEQ ID NOS: 54

<210> SEQ ID NO 1
<211> LENGTH: 6
<212> TYPE: PRT
<213> ORGANISM: Homo sapiens

<400> SEQUENCE: 1
```

Asp Ala Glu Phe Arg Cys
1               5

<210> SEQ ID NO 2
<211> LENGTH: 8
<212> TYPE: PRT
<213> ORGANISM: Homo sapiens

<400> SEQUENCE: 2

Asp Ala Glu Phe Arg His Asp Cys
1               5

<210> SEQ ID NO 3
<211> LENGTH: 10
<212> TYPE: PRT
<213> ORGANISM: Homo sapiens

<400> SEQUENCE: 3

Asp Ala Glu Phe Arg His Asp Ser Gly Cys
1               5                   10

<210> SEQ ID NO 4
<211> LENGTH: 13
<212> TYPE: PRT
<213> ORGANISM: Homo sapiens

<400> SEQUENCE: 4

Asp Ala Glu Phe Arg His Asp Ser Gly Tyr Glu Val Cys
1               5                   10

<210> SEQ ID NO 5
<211> LENGTH: 10
<212> TYPE: PRT
<213> ORGANISM: Homo sapiens

<400> SEQUENCE: 5

Asp Ala Glu Phe Arg Gly Ala Gly Ala Cys
1               5                   10

<210> SEQ ID NO 6
<211> LENGTH: 12
<212> TYPE: PRT
<213> ORGANISM: Homo sapiens

<400> SEQUENCE: 6

Asp Ala Glu Phe Arg His Asp Gly Ala Gly Ala Cys
1               5                   10

<210> SEQ ID NO 7
<211> LENGTH: 14
<212> TYPE: PRT
<213> ORGANISM: Homo sapiens

<400> SEQUENCE: 7

Asp Ala Glu Phe Arg His Asp Ser Gly Gly Ala Gly Ala Cys
1               5                   10

<210> SEQ ID NO 8
<211> LENGTH: 17
<212> TYPE: PRT
<213> ORGANISM: Homo sapiens

<400> SEQUENCE: 8

Asp Ala Glu Phe Arg His Asp Ser Gly Tyr Glu Val Gly Ala Gly Ala

```
                1               5                   10                  15
Cys

<210> SEQ ID NO 9
<211> LENGTH: 13
<212> TYPE: PRT
<213> ORGANISM: Homo sapiens

<400> SEQUENCE: 9

Val Glu Tyr Gly Ser Asp His Arg Phe Glu Ala Asp Cys
1               5                   10

<210> SEQ ID NO 10
<211> LENGTH: 4
<212> TYPE: PRT
<213> ORGANISM: Homo sapiens

<400> SEQUENCE: 10

Gly Ala Gly Ala
1

<210> SEQ ID NO 11
<211> LENGTH: 13
<212> TYPE: PRT
<213> ORGANISM: Homo sapiens

<400> SEQUENCE: 11

Pro Lys Tyr Val Lys Gln Asn Thr Leu Lys Leu Ala Thr
1               5                   10

<210> SEQ ID NO 12
<211> LENGTH: 13
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 12

Ala Lys Xaa Val Ala Ala Trp Thr Leu Lys Ala Ala Ala
1               5                   10

<210> SEQ ID NO 13
<211> LENGTH: 16
<212> TYPE: PRT
<213> ORGANISM: Homo sapiens

<400> SEQUENCE: 13

Glu Lys Lys Ile Ala Lys Met Glu Lys Ala Ser Ser Val Phe Asn Val
1               5                   10                  15

<210> SEQ ID NO 14
<211> LENGTH: 10
<212> TYPE: PRT
<213> ORGANISM: Homo sapiens

<400> SEQUENCE: 14

Phe Glu Leu Leu Thr Arg Ile Leu Thr Ile
1               5                   10

<210> SEQ ID NO 15
<211> LENGTH: 19
<212> TYPE: PRT
<213> ORGANISM: Homo sapiens
```

```
<400> SEQUENCE: 15

Asp Gln Ser Ile Gly Asp Leu Ile Ala Glu Ala Met Asp Lys Val Gly
1               5                   10                  15

Asn Glu Gly

<210> SEQ ID NO 16
<211> LENGTH: 14
<212> TYPE: PRT
<213> ORGANISM: Homo sapiens

<400> SEQUENCE: 16

Gln Val His Phe Gln Pro Leu Pro Pro Ala Val Val Lys Leu
1               5                   10

<210> SEQ ID NO 17
<211> LENGTH: 15
<212> TYPE: PRT
<213> ORGANISM: Homo sapiens

<400> SEQUENCE: 17

Gln Tyr Ile Lys Ala Asn Ser Lys Phe Ile Gly Ile Thr Glu Leu
1               5                   10                  15

<210> SEQ ID NO 18
<211> LENGTH: 21
<212> TYPE: PRT
<213> ORGANISM: Homo sapiens

<400> SEQUENCE: 18

Phe Asn Asn Phe Thr Val Ser Phe Trp Leu Arg Val Pro Lys Val Ser
1               5                   10                  15

Ala Ser His Leu Glu
            20

<210> SEQ ID NO 19
<211> LENGTH: 15
<212> TYPE: PRT
<213> ORGANISM: Homo sapiens

<400> SEQUENCE: 19

Lys Gln Ile Ile Asn Met Trp Gln Glu Val Gly Lys Ala Met Tyr
1               5                   10                  15

<210> SEQ ID NO 20
<211> LENGTH: 51
<212> TYPE: PRT
<213> ORGANISM: Homo sapiens

<400> SEQUENCE: 20

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
            20                  25                  30

Leu Arg Val Pro Lys Val Ser Ala Ser His Leu Glu Asp Ala Glu Phe
        35                  40                  45

Arg His Asp
        50

<210> SEQ ID NO 21
<211> LENGTH: 42
<212> TYPE: PRT
```

```
<213> ORGANISM: Homo sapiens

<400> SEQUENCE: 21

Asp Ala Glu Phe Arg His Asp Ser Gly Tyr Glu Val His His Gln Lys
1               5                   10                  15

Leu Val Phe Phe Ala Glu Asp Val Gly Ser Asn Lys Gly Ala Ile Ile
                20                  25                  30

Gly Leu Met Val Gly Gly Val Val Ile Ala
            35                  40

<210> SEQ ID NO 22
<211> LENGTH: 22
<212> TYPE: PRT
<213> ORGANISM: Homo sapiens

<400> SEQUENCE: 22

Asp Ala Glu Phe Arg His Asp Gln Tyr Ile Lys Ala Asn Ser Lys Phe
1               5                   10                  15

Ile Gly Ile Thr Glu Leu
            20

<210> SEQ ID NO 23
<211> LENGTH: 28
<212> TYPE: PRT
<213> ORGANISM: Homo sapiens

<400> SEQUENCE: 23

Asp Ala Glu Phe Arg His Asp Phe Asn Asn Phe Thr Val Ser Phe Trp
1               5                   10                  15

Leu Arg Val Pro Lys Val Ser Ala Ser His Leu Glu
                20                  25

<210> SEQ ID NO 24
<211> LENGTH: 43
<212> TYPE: PRT
<213> ORGANISM: Homo sapiens

<400> SEQUENCE: 24

Asp Ala Glu Phe Arg His Asp Gln Tyr Ile Lys Ala Asn Ser Lys Phe
1               5                   10                  15

Ile Gly Ile Thr Glu Leu Phe Asn Asn Phe Thr Val Ser Phe Trp Leu
                20                  25                  30

Arg Val Pro Lys Val Ser Ala Ser His Leu Glu
            35                  40

<210> SEQ ID NO 25
<211> LENGTH: 22
<212> TYPE: PRT
<213> ORGANISM: Homo sapiens

<400> SEQUENCE: 25

Glu Phe Arg His Asp Ser Gly Tyr Ile Lys Ala Asn Ser Lys Phe
1               5                   10                  15

Ile Gly Ile Thr Glu Leu
            20

<210> SEQ ID NO 26
<211> LENGTH: 20
<212> TYPE: PRT
<213> ORGANISM: Homo sapiens
<220> FEATURE:
<221> NAME/KEY: misc_feature
```

<222> LOCATION: (3)..(3)
<223> OTHER INFORMATION: Xaa can be any naturally occurring amino acid

<400> SEQUENCE: 26

Ala Lys Xaa Val Ala Ala Trp Thr Leu Lys Ala Ala Ala Asp Ala Glu
1               5                   10                  15

Phe Arg His Asp
            20

<210> SEQ ID NO 27
<211> LENGTH: 34
<212> TYPE: PRT
<213> ORGANISM: Homo sapiens
<220> FEATURE:
<221> NAME/KEY: misc_feature
<222> LOCATION: (24)..(24)
<223> OTHER INFORMATION: Xaa can be any naturally occurring amino acid

<400> SEQUENCE: 27

Asp Ala Glu Phe Arg His Asp Ala Glu Phe Arg His Asp Ala
1               5                   10                  15

Glu Phe Arg His Asp Ala Lys Xaa Val Ala Ala Trp Thr Leu Lys Ala
            20                  25                  30

Ala Ala

<210> SEQ ID NO 28
<211> LENGTH: 34
<212> TYPE: PRT
<213> ORGANISM: Homo sapiens
<220> FEATURE:
<221> NAME/KEY: misc_feature
<222> LOCATION: (3)..(3)
<223> OTHER INFORMATION: Xaa can be any naturally occurring amino acid

<400> SEQUENCE: 28

Ala Lys Xaa Val Ala Ala Trp Thr Leu Lys Ala Ala Ala Asp Ala Glu
1               5                   10                  15

Phe Arg His Asp Asp Ala Glu Phe Arg His Asp Asp Ala Glu Phe Arg
            20                  25                  30

His Asp

<210> SEQ ID NO 29
<211> LENGTH: 20
<212> TYPE: PRT
<213> ORGANISM: Homo sapiens
<220> FEATURE:
<221> NAME/KEY: misc_feature
<222> LOCATION: (10)..(10)
<223> OTHER INFORMATION: Xaa can be any naturally occurring amino acid

<400> SEQUENCE: 29

Asp Ala Glu Phe Arg His Asp Ala Lys Xaa Val Ala Ala Trp Thr Leu
1               5                   10                  15

Lys Ala Ala Ala
            20

<210> SEQ ID NO 30
<211> LENGTH: 24
<212> TYPE: PRT
<213> ORGANISM: Homo sapiens

<400> SEQUENCE: 30

Asp Ala Glu Phe Arg His Asp Ile Ser Gln Ala Val His Ala Ala His
1               5                   10                  15

```
Ala Glu Ile Asn Glu Ala Gly Arg
            20

<210> SEQ ID NO 31
<211> LENGTH: 24
<212> TYPE: PRT
<213> ORGANISM: Homo sapiens

<400> SEQUENCE: 31

Phe Arg His Asp Ser Gly Tyr Ile Ser Gln Ala Val His Ala Ala His
1               5                   10                  15

Ala Glu Ile Asn Glu Ala Gly Arg
            20

<210> SEQ ID NO 32
<211> LENGTH: 24
<212> TYPE: PRT
<213> ORGANISM: Homo sapiens

<400> SEQUENCE: 32

Glu Phe Arg His Asp Ser Gly Tyr Ile Ser Gln Ala Val His Ala Ala His
1               5                   10                  15

Ala Glu Ile Asn Glu Ala Gly Arg
            20

<210> SEQ ID NO 33
<211> LENGTH: 34
<212> TYPE: PRT
<213> ORGANISM: Homo sapiens

<400> SEQUENCE: 33

Pro Lys Tyr Val Lys Gln Asn Thr Leu Lys Leu Ala Thr Asp Ala Glu
1               5                   10                  15

Phe Arg His Asp Asp Ala Glu Phe Arg His Asp Asp Ala Glu Phe Arg
            20                  25                  30

His Asp

<210> SEQ ID NO 34
<211> LENGTH: 27
<212> TYPE: PRT
<213> ORGANISM: Homo sapiens

<400> SEQUENCE: 34

Asp Ala Glu Phe Arg His Asp Pro Lys Tyr Val Lys Gln Asn Thr Leu
1               5                   10                  15

Lys Leu Ala Thr Asp Ala Glu Phe Arg His Asp
            20                  25

<210> SEQ ID NO 35
<211> LENGTH: 34
<212> TYPE: PRT
<213> ORGANISM: Homo sapiens

<400> SEQUENCE: 35

Asp Ala Glu Phe Arg His Asp Asp Ala Glu Phe Arg His Asp Asp Ala
1               5                   10                  15

Glu Phe Arg His Asp Pro Lys Tyr Val Lys Gln Asn Thr Leu Lys Leu
            20                  25                  30

Ala Thr
```

```
<210> SEQ ID NO 36
<211> LENGTH: 27
<212> TYPE: PRT
<213> ORGANISM: Homo sapiens

<400> SEQUENCE: 36

Asp Ala Glu Phe Arg His Asp Ala Glu Phe Arg His Asp Pro Lys
1               5                   10                  15

Tyr Val Lys Gln Asn Thr Leu Lys Leu Ala Thr
            20                  25

<210> SEQ ID NO 37
<211> LENGTH: 79
<212> TYPE: PRT
<213> ORGANISM: Homo sapiens

<400> SEQUENCE: 37

Asp Ala Glu Phe Arg His Asp Pro Lys Tyr Val Lys Gln Asn Thr Leu
1               5                   10                  15

Lys Leu Ala Thr Glu Lys Lys Ile Ala Lys Met Glu Lys Ala Ser Ser
            20                  25                  30

Val Phe Asn Val Gln Tyr Ile Lys Ala Asn Ser Lys Phe Ile Gly Ile
        35                  40                  45

Thr Glu Leu Phe Asn Asn Phe Thr Val Ser Phe Trp Leu Arg Val Pro
    50                  55                  60

Lys Val Ser Ala Ser His Leu Glu Asp Ala Glu Phe Arg His Asp
65                  70                  75

<210> SEQ ID NO 38
<211> LENGTH: 58
<212> TYPE: PRT
<213> ORGANISM: Homo sapiens

<400> SEQUENCE: 38

Asp Ala Glu Phe Arg His Asp Ala Glu Phe Arg His Asp Ala
1               5                   10                  15

Glu Phe Arg His Asp Gln Tyr Ile Lys Ala Asn Ser Lys Phe Ile Gly
            20                  25                  30

Ile Thr Glu Leu Cys Phe Asn Asn Phe Thr Val Ser Phe Trp Leu Arg
        35                  40                  45

Val Pro Lys Val Ser Ala Ser His Leu Glu
    50                  55

<210> SEQ ID NO 39
<211> LENGTH: 44
<212> TYPE: PRT
<213> ORGANISM: Homo sapiens

<400> SEQUENCE: 39

Asp Ala Glu Phe Arg His Asp Gln Tyr Ile Lys Ala Asn Ser Lys Phe
1               5                   10                  15

Ile Gly Ile Thr Glu Leu Cys Phe Asn Asn Phe Thr Val Ser Phe Trp
            20                  25                  30

Leu Arg Val Pro Lys Val Ser Ala Ser His Leu Glu
        35                  40

<210> SEQ ID NO 40
<211> LENGTH: 535
<212> TYPE: PRT
<213> ORGANISM: Homo sapiens
```

-continued

```
<400> SEQUENCE: 40

Gly Ala Asp Asp Val Val Asp Ser Ser Lys Ser Phe Val Met Glu Asn
1               5                   10                  15

Phe Ser Ser Tyr His Gly Thr Lys Pro Gly Tyr Val Asp Ser Ile Gln
            20                  25                  30

Lys Gly Ile Gln Lys Pro Lys Ser Gly Thr Gln Gly Asn Tyr Asp Asp
        35                  40                  45

Asp Trp Lys Glu Phe Tyr Ser Thr Asp Asn Lys Tyr Asp Ala Ala Gly
    50                  55                  60

Tyr Ser Val Asp Asn Glu Asn Pro Leu Ser Gly Lys Ala Gly Gly Val
65                  70                  75                  80

Val Lys Val Thr Tyr Pro Gly Leu Thr Lys Val Leu Ala Leu Lys Val
                85                  90                  95

Asp Asn Ala Glu Thr Ile Lys Lys Glu Leu Gly Leu Ser Leu Thr Glu
            100                 105                 110

Pro Leu Met Glu Gln Val Gly Thr Glu Glu Phe Ile Lys Arg Phe Gly
        115                 120                 125

Asp Gly Ala Ser Arg Val Val Leu Ser Leu Pro Phe Ala Glu Gly Ser
    130                 135                 140

Ser Ser Val Glu Tyr Ile Asn Asn Trp Glu Gln Ala Lys Ala Leu Ser
145                 150                 155                 160

Val Glu Leu Glu Ile Asn Phe Glu Thr Arg Gly Lys Arg Gly Gln Asp
                165                 170                 175

Ala Met Tyr Glu Tyr Met Ala Gln Ala Cys Ala Gly Asn Arg Val Arg
            180                 185                 190

Arg Ser Val Gly Ser Ser Leu Ser Cys Ile Asn Leu Asp Trp Asp Val
        195                 200                 205

Ile Arg Asp Lys Thr Lys Thr Lys Ile Glu Ser Leu Lys Glu His Gly
    210                 215                 220

Pro Ile Lys Asn Lys Met Ser Glu Ser Pro Asn Lys Thr Val Ser Glu
225                 230                 235                 240

Glu Lys Ala Lys Gln Tyr Leu Glu Glu Phe His Gln Thr Ala Leu Glu
                245                 250                 255

His Pro Glu Leu Ser Glu Leu Lys Thr Val Thr Gly Thr Asn Pro Val
            260                 265                 270

Phe Ala Gly Ala Asn Tyr Ala Ala Trp Ala Val Asn Val Ala Gln Val
        275                 280                 285

Ile Asp Ser Glu Thr Ala Asp Asn Leu Glu Lys Thr Thr Ala Ala Leu
    290                 295                 300

Ser Ile Leu Pro Gly Ile Gly Ser Val Met Gly Ile Ala Asp Gly Ala
305                 310                 315                 320

Val His His Asn Thr Glu Glu Ile Val Ala Gln Ser Ile Ala Leu Ser
                325                 330                 335

Ser Leu Met Val Ala Gln Ala Ile Pro Leu Val Gly Glu Leu Val Asp
            340                 345                 350

Ile Gly Phe Ala Ala Tyr Asn Phe Val Glu Ser Ile Ile Asn Leu Phe
        355                 360                 365

Gln Val Val His Asn Ser Tyr Asn Arg Pro Ala Tyr Ser Pro Gly His
    370                 375                 380

Lys Thr Gln Pro Phe Leu His Asp Gly Tyr Ala Val Ser Trp Asn Thr
385                 390                 395                 400
```

-continued

```
Val Glu Asp Ser Ile Ile Arg Thr Gly Phe Gln Gly Glu Ser Gly His
            405                 410                 415

Asp Ile Lys Ile Thr Ala Glu Asn Thr Pro Leu Pro Ile Ala Gly Val
            420                 425                 430

Leu Leu Pro Thr Ile Pro Gly Lys Leu Asp Val Asn Lys Ser Lys Thr
            435                 440                 445

His Ile Ser Val Asn Gly Arg Lys Ile Arg Met Arg Cys Arg Ala Ile
            450                 455                 460

Asp Gly Asp Val Thr Phe Cys Arg Pro Lys Ser Pro Val Tyr Val Gly
465                 470                 475                 480

Asn Gly Val His Ala Asn Leu His Val Ala Phe His Arg Ser Ser Ser
                485                 490                 495

Glu Lys Ile His Ser Asn Glu Ile Ser Ser Asp Ser Ile Gly Val Leu
            500                 505                 510

Gly Tyr Gln Lys Thr Val Asp His Thr Lys Val Asn Ser Lys Leu Ser
            515                 520                 525

Leu Phe Phe Glu Ile Lys Ser
    530                 535
```

<210> SEQ ID NO 41
<211> LENGTH: 17
<212> TYPE: PRT
<213> ORGANISM: Homo sapiens

<400> SEQUENCE: 41

```
Ile Ser Gln Ala Val His Ala Ala His Ala Glu Ile Asn Glu Ala Gly
1               5                   10                  15

Arg
```

<210> SEQ ID NO 42
<211> LENGTH: 42
<212> TYPE: PRT
<213> ORGANISM: Mus musculus

<400> SEQUENCE: 42

```
Asp Ala Glu Phe Gly His Asp Ser Gly Phe Glu Val Arg His Gln Lys
1               5                   10                  15

Leu Val Phe Phe Ala Glu Asp Val Gly Ser Asn Lys Gly Ala Ile Ile
            20                  25                  30

Gly Leu Met Val Gly Gly Val Val Ile Ala
        35                  40
```

<210> SEQ ID NO 43
<211> LENGTH: 9
<212> TYPE: PRT
<213> ORGANISM: Artificial
<220> FEATURE:
<223> OTHER INFORMATION: A-beta 18-25 + C

<400> SEQUENCE: 43

```
Val Phe Phe Ala Glu Asp Val Gly Cys
1               5
```

<210> SEQ ID NO 44
<211> LENGTH: 9
<212> TYPE: PRT
<213> ORGANISM: Artificial
<220> FEATURE:
<223> OTHER INFORMATION: A-beta 17-24 + C

```
<400> SEQUENCE: 44

Leu Val Phe Phe Ala Glu Asp Val Cys
1               5

<210> SEQ ID NO 45
<211> LENGTH: 9
<212> TYPE: PRT
<213> ORGANISM: Artificial
<220> FEATURE:
<223> OTHER INFORMATION: A-beta 16-23 + C

<400> SEQUENCE: 45

Lys Leu Val Phe Phe Ala Glu Asp Cys
1               5

<210> SEQ ID NO 46
<211> LENGTH: 9
<212> TYPE: PRT
<213> ORGANISM: Artificial
<220> FEATURE:
<223> OTHER INFORMATION: A-beta 18-25 + C

<400> SEQUENCE: 46

Cys Val Phe Phe Ala Glu Asp Val Gly
1               5

<210> SEQ ID NO 47
<211> LENGTH: 9
<212> TYPE: PRT
<213> ORGANISM: Artificial
<220> FEATURE:
<223> OTHER INFORMATION: C + A-beta 18-25

<400> SEQUENCE: 47

Cys Leu Val Phe Phe Ala Glu Asp Val
1               5

<210> SEQ ID NO 48
<211> LENGTH: 9
<212> TYPE: PRT
<213> ORGANISM: Artificial
<220> FEATURE:
<223> OTHER INFORMATION: C + A-beta 16-23

<400> SEQUENCE: 48

Cys Lys Leu Val Phe Phe Ala Glu Asp
1               5

<210> SEQ ID NO 49
<211> LENGTH: 8
<212> TYPE: PRT
<213> ORGANISM: Artificial
<220> FEATURE:
<223> OTHER INFORMATION: A-beta 18-24 + C

<400> SEQUENCE: 49

Val Phe Phe Ala Glu Asp Val Cys
1               5

<210> SEQ ID NO 50
<211> LENGTH: 8
<212> TYPE: PRT
<213> ORGANISM: Artificial
<220> FEATURE:
<223> OTHER INFORMATION: A-beta 17-23 + C
```

```
<400> SEQUENCE: 50

Leu Val Phe Phe Ala Glu Asp Cys
1               5

<210> SEQ ID NO 51
<211> LENGTH: 8
<212> TYPE: PRT
<213> ORGANISM: Artificial
<220> FEATURE:
<223> OTHER INFORMATION: A-beta 16-22 + C
<220> FEATURE:
<221> NAME/KEY: misc_feature
<222> LOCATION: (8)..(8)
<223> OTHER INFORMATION: CRM 197 added via terminal cysteine

<400> SEQUENCE: 51

Lys Leu Val Phe Phe Ala Glu Cys
1               5

<210> SEQ ID NO 52
<211> LENGTH: 8
<212> TYPE: PRT
<213> ORGANISM: Artificial
<220> FEATURE:
<223> OTHER INFORMATION: C + A-beta 18-24
<220> FEATURE:
<221> NAME/KEY: misc_feature
<222> LOCATION: (1)..(1)
<223> OTHER INFORMATION: CRM 197 added via N-terminal cysteine

<400> SEQUENCE: 52

Cys Val Phe Phe Ala Glu Asp Val
1               5

<210> SEQ ID NO 53
<211> LENGTH: 8
<212> TYPE: PRT
<213> ORGANISM: Artificial
<220> FEATURE:
<223> OTHER INFORMATION: C + A-beta 17-23

<400> SEQUENCE: 53

Cys Leu Val Phe Phe Ala Glu Asp
1               5

<210> SEQ ID NO 54
<211> LENGTH: 8
<212> TYPE: PRT
<213> ORGANISM: Artificial
<220> FEATURE:
<223> OTHER INFORMATION: C + A-beta 16-22 + C
<220> FEATURE:
<221> NAME/KEY: misc_feature
<222> LOCATION: (1)..(1)
<223> OTHER INFORMATION: CRM 197 added via N-terminal cysteine

<400> SEQUENCE: 54

Cys Lys Leu Val Phe Phe Ala Glu
1               5
```

A-β IMMUNOGENIC PEPTIDE CARRIER CONJUGATES AND METHODS OF PRODUCING SAME

CROSS-REFERENCES TO RELATED APPLICATIONS

This application is a continuation of U.S. application Ser. No. 11/841,919, filed Aug. 20, 2007, which is a divisional of U.S. application Ser. No. 10/583,503 filed Nov. 17, 2006, now U.S. Pat. No. 8,227,403, which is a national stage of PCT/US04/44093 filed Dec. 17, 2004, which claims the benefit under 35 U.S.C. §119(e) of U.S. Provisional Patent Application Ser. No. 60/530,481, filed Dec. 17, 2003, which is incorporated herein by reference in its entirety for all purposes.

PARTIES TO A JOINT RESEARCH AGREEMENT

The claimed invention was made pursuant to a written joint research agreement by and among American Home Products Corporation, together with Affiliates of American Home Products Corporation, acting through American Home Products Corporation's Wyeth-Ayerst Laboratories Division, and Neuralab Limited.

BACKGROUND OF THE INVENTION

The essence of adaptive immunity is the ability of an organism to react to the presence of foreign substances and produce components (antibodies and cells) capable of specifically interacting with and protecting the host from their invasion. An "antigen" or "immunogen" is a substance that is able to elicit this type of immune response and also is capable of interacting with the sensitized cells and antibodies that are manufactured against it.

Antigens or immunogens are usually macromolecules that contain distinct antigenic sites or "epitopes" that are recognized and interact with the various components of the immune system. They can exist as individual molecules composed of synthetic organic chemicals, proteins, lipoproteins, glycoproteins, RNA, DNA, or polysaccharides, or they may be parts of cellular structures (bacteria or fungi) or viruses (Harlow and Lane 1988a, b, c; Male et al., 1987).

Small molecules like short peptides, although normally able to interact with the products of an immune response, often cannot cause a response on their own. These peptide immunogens or "haptens" as they are also called, are actually incomplete antigens, and, although not able by themselves to cause immunogenicity or to elicit antibody production, can be made immunogenic by coupling them to a suitable carrier. Carriers typically are protein antigens of higher molecular weight that are able to cause an immunological response when administered in vivo.

In an immune response, antibodies are produced and secreted by the B-lymphocytes in conjunction with the T-helper ($T_H$) cells. In the majority of hapten-carrier systems, the B cells produce antibodies that are specific for both the hapten and the carrier. In these cases, the T lymphocytes will have specific binding domains on the carrier, but will not recognize the hapten alone. In a kind of synergism, the B and T cells cooperate to induce a hapten-specific antibody response. After such an immune response has taken place, if the host is subsequently challenged with only the hapten, usually it will respond by producing hapten-specific antibodies from memory cells formed after the initial immunization.

Synthetic haptens mimicking some critical epitopic structures on larger macromolecules are often conjugated to carriers to create an immune response to the larger "parent" molecule. For instance, short peptide segments can be synthesized from the known sequence of a protein and coupled to a carrier to induce immunogenicity toward the native protein. This type of synthetic approach to the immunogen production has become the basis of much of the current research into the creation of vaccines. However, in many instances, merely creating a B-cell response by using synthetic peptide-carrier conjugates, however well designed, will not always guarantee complete protective immunity toward an intact antigen. The immune response generated by a short peptide epitope from a larger viral particle or bacterial cell may only be sufficient to generate memory at the B cell level. In these cases it is generally now accepted that a cytotoxic T-cell response is a more important indicator of protective immunity. Designing peptide immunogens with the proper epitopic binding sites for both B-cell and T-cell recognition is one of the most challenging research areas in immunology today.

The approach to increasing immunogenicity of small or poorly immunogenic molecules by conjugating these molecules to large "carrier" molecules has been utilized successfully for decades (see, e.g., Goebel et al. (1939) *J. Exp. Med.* 69: 53). For example, many immunogenic compositions have been described in which purified capsular polymers have been conjugated to carrier proteins to create more effective immunogenic compositions by exploiting this "carrier effect." Schneerson et al. (1984) *Infect. Immun.* 45: 582-591). Conjugation has also been shown to bypass the poor antibody response usually observed in infants when immunized with a free polysaccharide (Anderson et al. (1985) *J. Pediatr.* 107: 346; Insel et al. (1986) *J. Exp. Med.* 158: 294).

Hapten-carrier conjugates have been successfully generated using various cross-linking/coupling reagents such as homobifunctional, heterobifunctional, or zero-length cross linkers. Many such methods are currently available for coupling of saccharides, proteins, and peptides to peptide carriers. Most methods create amine, amide, urethane, isothiourea, or disulfide bonds, or in some cases thioethers. A disadvantage to the use of coupling reagents, which introduce reactive sites in to the side chains of reactive amino acid molecules on carrier and/or hapten molecules, is that the reactive sites if not neutralized are free to react with any unwanted molecule either in vitro (thus adversely affecting the functionality or stability of the conjugate(s)) or in vivo (thus posing a potential risk of adverse events in persons or animals immunized with the preparations). Such excess reactive sites can be reacted or "capped", so as to inactivate these sites, utilizing various known chemical reactions, but these reactions may be otherwise disruptive to the functionality of the conjugates. This may be particularly problematic when attempting to create a conjugate by introducing the reactive sites into the carrier molecule, as its larger size and more complex structure (relative to the hapten) may render it more vulnerable to the disruptive effects of chemical treatment. In fact, no examples are known of methods whereby a conjugate is made by first activating the carrier, then reacting with the hapten in a conjugation reaction, and finally "capping" the remaining reactive sites, while preserving the ability of the resulting conjugate to function as an immunogenic composition having the desired properties of the "carrier effect".

BRIEF SUMMARY OF THE INVENTION

The present invention is directed to methods of producing an immunogenic conjugate of a peptide immunogen comprising Aβ peptide or fragments of Aβ or analogs thereof with a protein/polypeptide carrier, wherein the Aβ peptide or fragments of Aβ or analogs thereof is conjugated to the carrier via derivatized functional groups of amino acid residues of the carrier such as lysine residues, and wherein any unconjugated, derivatized functional groups of the amino acid residues are inactivated via capping to block them from reacting with other molecules, including proteins/polypeptides thereby preserving the functionality of the carrier, such that it retains its ability to elicit the desired immune responses against the peptide immunogen that would otherwise not occur without a carrier. Furthermore, the invention also relates to conjugates produced by the above methods, and to immunogenic compositions containing such conjugates.

In one embodiment, the invention is directed to a first method for conjugating a peptide immunogen comprising Aβ peptide or fragments of Aβ or analogs thereof via a reactive group of an amino acid residue of the peptide immunogen to a protein/polypeptide carrier having one or more functional groups, the method comprising the steps of: (a) derivatizing one or more of the functional groups of the protein/polypeptide carrier to generate a derivatized molecule with reactive sites; (b) reacting the derivatized protein/polypeptide carrier of step (a) with a reactive group of an amino acid residue of the peptide immunogen under reaction conditions such that the peptide immunogen is conjugated to the derivatized protein/polypeptide carrier via the functional groups; and (c) further reacting the conjugate with a capping reagent to inactivate free, reactive functional groups on the activated protein/polypeptide carrier, thereby preserving the functionality of the carrier such that it retains its ability to elicit the desired immune responses against the peptide immunogen that would otherwise not occur without a carrier.

In one embodiment, the protein/polypeptide carrier is selected from the group consisting of human serum albumin, keyhole limpet hemocyanin, immunoglobulin molecules, thyroglobulin, ovalbumin, influenza hemagglutinin, PAN-DR binding peptide (PADRE polypeptide), malaria circumsporozite (CS) protein, hepatitis B surface antigen ($HB_sAg_{19-28}$), Heat Shock Protein (HSP) 65, *Bacillus* Calmette-Guerin (BCG), cholera toxin, cholera toxin mutants with reduced toxicity, diphtheria toxin, $CRM_{197}$ protein that is cross-reactive with diphtheria toxin, recombinant Streptococcal C5a peptidase, *Streptococcus pyogenes* ORF1224, *Streptococcus pyogenes* ORF1664, *Streptococcus pyogenes* ORF 2452, *Streptococcus pneumoniae* pneumolysin, pneumolysin mutants with reduced toxicity, *Chlamydia pneumoniae* ORF T367, *Chlamydia pneumoniae* ORF T858, Tetanus toxoid, HIV gp120 T1, microbial surface components recognizing adhesive matrix molecules (MSCRAMMS), growth factor/hormone, cytokines and chemokines.

In another embodiment, the protein/polypeptide carrier contains a T-cell epitope.

In yet another embodiment, the protein/polypeptide carrier is a bacterial toxoid such as a tetanus toxoid, cholera toxin or cholera toxin mutant as described above. In a preferred embodiment, the protein/polypeptide carrier is $CRM_{197}$.

In still yet another embodiment, the protein/polypeptide carrier may be an influenza hemagglutinin, a PADRE polypeptide, a malaria CS protein, a Hepatitis B surface antigen ($HSBAg_{19-28}$), a heat shock protein 65 (HSP 65), or a polypeptide from *Mycobacterium tuberculosis* (BCG).

In a preferred embodiment, the protein/polypeptide carrier is selected from Streptococcal rC5a peptidase, *Streptococcus pyogenes* ORF1224, *Streptococcus pyogenes* ORF1664 or *Streptococcus pyogenes* ORF2452, *Streptococcus pneumoniae* pneumolysin, pneumolysin mutants with reduced toxicity, *Chlamydia pneumoniae* ORF T367, and *Chlamydia pneumoniae* ORF T858.

In one embodiment, protein/polypeptide carrier is a growth factor or hormone, which stimulates or enhances immune response and is selected from the group consisting of IL-1, IL-2, γ-interferon, IL-10, GM-CSF, MIP-1α, MIP-1β, and RANTES.

In one aspect, the invention provides a peptide immunogen comprising Aβ peptide or fragments of Aβ or analogs thereof eliciting an immunogenic response against certain epitopes within Aβ. Immunogenic peptides of the invention include immunogenic heterologous peptides. In some immunogenic peptides, an Aβ fragment is linked to a carrier to form an immunogenic heterologous peptide, and then this heterologous peptide is linked to a carrier using a method of the present invention to form a conjugate.

In another aspect of the invention, the peptide immunogen is a polypeptide comprising an N-terminal segment of at least residues 1-5 of Aβ, the first residue of Aβ being the N-terminal residue of the polypeptide, wherein the polypeptide is free of a C-terminal segment of Aβ. In yet another aspect of the invention, the peptide immunogen is a polypeptide comprising an N-terminal segment of Aβ, the segment beginning at residue 1-3 of Aβ and ending at residues 7-11 of Aβ. In some aspects of the invention, the peptide immunogen is an agent that induces an immunogenic response against an N-terminal segment of Aβ, the segment beginning at residue 1-3 of Aβ and ending at residues 7-11 of Aβ without inducing an immunogenic response against an epitope within residues 12-43 of Aβ43. In another aspect of the invention, the peptide immunogen is a heterologous polypeptide comprising a segment of Aβ linked to a heterologous amino acid sequence that induces a helper T-cell response against the heterologous amino acid sequence and thereby a B-cell response against the N-terminal segment.

In some peptide immunogens, the N-terminal segment of Aβ is linked at its C-terminus to a heterologous polypeptide. In some peptide immunogens, the N-terminal segment of Aβ is linked at its N-terminus to a heterologous polypeptide. In some peptide immunogens, the N-terminal segment of Aβ is linked at its N and C termini to first and second heterologous polypeptides. In some peptide immunogens, the N-terminal segment of Aβ is linked at its N terminus to a heterologous polypeptide, and at its C-terminus to at least one additional copy of the N-terminal segment. In some peptide immunogens, the polypeptide comprises from N-terminus to C-terminus, the N-terminal segment of Aβ, a plurality of additional copies of the N-terminal segment, and the heterologous amino acid segment.

In some of the above peptide immunogens, the polypeptide further comprises at least one additional copy of the N-terminal segment. In some of the above peptide immunogens, the fragment is free of at least the 5 C-terminal amino acids in Aβ43.

In some aspects of the above peptide immunogens, the fragment comprises up to 10 contiguous amino acids from Aβ.

In another aspect, the invention provides a peptide immunogen comprising Aβ peptide or fragments of Aβ or analogs thereof eliciting an immunogenic response against certain epitopes within Aβ may be in a configuration referred to as a multiple antigenic peptide (MAP) configuration.

In some of the above aspects of the invention, the peptide immunogen from the N-terminal half of Aβ. In some aspects of the invention, the peptide immunogen is an Aβ fragment selected from the group consisting of Aβ1-3, 1-4, 1-5, 1-6, 1-7, 1-10, 1-11, 1-12, 1-16, 3-6, and 3-7. In some of the above aspects of the invention, the peptide immunogen is from the internal region of Aβ. In some aspects of the invention, the peptide immunogen is an Aβ fragment selected from the group consisting of Aβ13-28, 15-24, 17-28, and 25-35. In some of the above aspects of the invention, the peptide immunogen from the C-terminal end of Aβ. In some aspects of the invention, the peptide immunogen is an Aβ fragment selected from the group consisting of Aβ33-42, 35-40, and 35-42. In some aspects of the invention, the peptide immunogen is an Aβ fragment selected from the group consisting of Aβ1-3, 1-4, 1-5, 1-6, 1-7, 1-10, 1-11, 1-12, 1-16, 1-28, 3-6, 3-7, 13-28, 15-24, 17-28, 25-35, 33-42, 35-40, and 35-42. In some aspects of the invention, the peptide immunogen is an Aβ fragment selected from the group consisting of Aβ1-5, Aβ1-7, Aβ1-9, and Aβ1-12. In some aspects of the invention, the peptide immunogen is an Aβ fragment selected from the group consisting of Aβ1-5-L, Aβ1-7-L, Aβ1-9-L, and Aβ1-12-L, where L is a linker. In some aspects of the invention, the peptide immunogen is an Aβ fragment selected from the group consisting of Aβ1-5-L-C, Aβ1-7-L-C, Aβ1-9-L-C, and Aβ1-12-L-C, where C is a cysteine amino acid residue.

In some aspects of the invention, the peptide immunogen is an Aβ fragment selected from the group consisting of Aβ16-22, Aβ16-23, Aβ17-23, Aβ17-24, Aβ18-24, and Aβ18-25. In some aspects of the invention, the peptide immunogen is an Aβ fragment selected from the group consisting of Aβ16-22-C, Aβ16-23-C, Aβ17-23-C, Aβ17-24-C, Aβ18-24-C, and Aβ18-25-C, where C is a cysteine amino acid residue. In other aspects of the invention, the peptide immunogen is an Aβ fragment selected from the group consisting of C-Aβ16-22, C-Aβ16-23, C-Aβ17-23, C-Aβ17-24, C-Aβ18-24, and C-Aβ18-25, where C is a cysteine amino acid residue.

In some of the above peptide immunogens, the heterologous polypeptide is selected from the group consisting of peptides having a T-cell epitope, a B-cell epitope and combinations thereof.

In one embodiment, the functional group of one or more amino acid molecules of the protein/polypeptide carrier or of the optionally attached polypeptide linker is derivatized using a cross-linking reagent. In another embodiment, the derivatizing reagent is a zero-length cross-linking reagent. In another embodiment, the derivatizing reagent is a homobifunctional cross-linking reagent. In yet another embodiment, the derivatizing reagent is a heterobifunctional cross-linking reagent.

In a preferred embodiment, the heterobifunctional reagent is a reagent that reacts with a primary or a ε-amine functional group of one or more amino acid molecules of the protein/polypeptide carrier and a pendant thiol group of one or more amino acid molecules of the peptide immunogen. In one embodiment, the heterobifunctional reagent is N-succinimidyl bromoacetate.

In another embodiment, the primary or ε-amine functional group is lysine. In yet another embodiment, the derivatization of the primary or ε-amine functional group of the lysine of the protein/polypeptide carrier with N-succinimidyl bromoacetate results in the bromoacetylation of the primary or ε-amine residues on lysine molecules on the protein/polypeptide carrier. In a more preferred embodiment, the pendant thiol group is a cysteine residue of the peptide immunogen, which may be localized at the amino-terminus of the peptide immunogen, at the carboxy-terminus of the peptide immunogen or internally in the peptide immunogen.

In another embodiment, the pendant thiol group is generated by a thiolating reagent such as N-acetyl homocysteinethio lactone, Traut's reagent (2-iminothilane) SATA (N-Succinimidyl S-acetylthioacetate), SMPT (4-Succinimidyloxycarbonyl-methyl2-pyridyldithio toluene), Sulfo LC SPDP (Sulfo Succinimidyl pyridyl dithio propionamido hexanoate), SPDP (Succinimidyl pyridyl dithio propionate). In a preferred embodiment, the capping reagent that is used to inactivate free reactive, functional groups on the activated protein/polypeptide carrier is selected from the reagent group consisting of cysteamine, N-acetylcysteamine, and ethanolamine.

In a particularly preferred embodiment, the capping reagent that is used to inactivate free reactive functional groups on the activated protein/polypeptide carrier is selected from the reagent group consisting of sodium hydroxide, sodium carbonate, ammonium bicarbonate and ammonia.

In one embodiment, the reactive group of the amino acid residue of the peptide immunogen is a free sulfhydryl group.

In another embodiment, one or more of the functional groups are on a linker, which is optionally attached to the protein/polypeptide carrier. In a preferred embodiment, the linker is a peptide linker. In a more preferred embodiment, the peptide linker is polylysine.

In another embodiment, the invention is directed to a second method for conjugating a peptide immunogen comprising Aβ peptide or fragments of Aβ or analogs thereof Aβ or analogs thereof with a protein/polypeptide carrier having the structure:

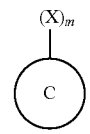

wherein,

C is a protein/polypeptide carrier and X is a derivatizable functional group of an amino acid residue on the protein/polypeptide carrier or optionally of an amino acid residue of a peptide linker covalently attached to the protein/polypeptide carrier, and wherein m is an integer greater than 0, but less than or equal to 85, the method comprising the steps of (a) derivatizing one or more of the functional groups of the protein/polypeptide carrier or of the optionally attached linker molecule to generate a derivatized molecule with reactive sites; (b) reacting the derivatized protein/polypeptide carrier of step (a) with a reactive group of an amino acid residue of the peptide immunogen to form a covalently coupled peptide immunogen-protein/polypeptide carrier conjugate; and (c) further reacting the said conjugate with a capping reagent to inactive the free reactive functional groups on the activated protein/polypeptide carrier, such that the capped groups are not free to react with other molecules, including proteins/polypeptides thereby preserving the functionality of the carrier, such that it retains its ability to elicit the desired immune responses against the peptide immunogen that would otherwise not occur without a carrier so as to generate a capped peptide immunogen-protein/polypeptide carrier conjugate having the formula:

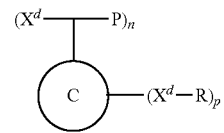

wherein,

C is the protein/polypeptide carrier and $X^d$ is a derivatized functional group of an amino acid residue of the protein/ polypeptide carrier or optionally of an amino acid residue of a peptide linker covalently attached to the protein/polypeptide carrier, and, wherein, P is the peptide immunogen molecule covalently attached to the derivatized functional group on the amino acid residue on the protein carrier or optionally on an amino acid residue on a peptide linker covalently attached to a protein/polypeptide carrier, R is a capping molecule covalently attached to the derivatized functional group on an amino acid residue on the protein/polypeptide carrier or optionally on an amino acid residue on a peptide linker covalently attached to a protein/polypeptide carrier, n is an integer greater than 0, but less than or equal to 85, and p is an integer greater than 0, but less than 85.

The detailed embodiments for the first method described above are also applicable to the conjugates just described prepared by the second method.

In one embodiment, the invention is directed to peptide immunogen-comprising peptide or fragments of Aβ or analogs thereof/polypeptide carrier conjugates wherein the protein/polypeptide carrier has the formula:

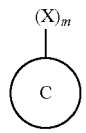

wherein,

C is a protein/polypeptide carrier and X is a derivatizable functional group of an amino acid residue on the protein/polypeptide carrier or optionally of an amino acid residue of a peptide linker covalently attached to the protein/polypeptide carrier, and, wherein, m is an integer greater than 0, but less than or equal to 85, and wherein the capped peptide immunogen-protein/polypeptide carrier conjugate has the formula:

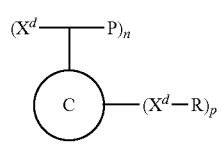

wherein,

C is the protein/polypeptide carrier and $X^d$ is a derivatized functional group of an amino acid residue of the protein/polypeptide carrier or optionally of an amino acid residue of a peptide linker covalently attached to the protein/polypeptide carrier, and, wherein, P is the peptide immunogen molecule covalently attached to the derivatized functional group of the amino acid residue of the protein carrier or optionally of an amino acid residue of a peptide linker covalently attached to a protein/polypeptide carrier, R is a capping molecule covalently attached to the derivatized functional group of an amino acid residue of the protein/polypeptide carrier or optionally of an amino acid residue of a peptide linker covalently attached to a protein/polypeptide carrier, thereby preserving the functionality of the carrier, such that it retains its ability to elicit the desired immune responses against the peptide immunogen that would otherwise not occur without a carrier, n is an integer greater than 0, but less than or equal to 85, and p is an integer greater than 0, but less than 85.

The detailed embodiments for the first and second methods described above are also applicable to the conjugates just described.

In another embodiment, the invention is directed to peptide immunogen-comprising Aβ peptide or fragments of Aβ or analogs thereof/polypeptide carrier conjugates generated according to the second method of the invention and having the formula:

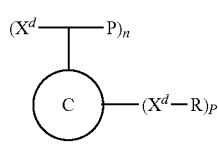

wherein,

C is the protein/polypeptide carrier and $X^d$ is a derivatized functional group of an amino acid residue of the protein/polypeptide carrier or optionally of an amino acid residue of a peptide linker covalently attached to the protein/polypeptide carrier, and, wherein, P is the peptide immunogen molecule covalently attached to the derivatized functional group of the amino acid residue of the protein carrier or optionally of an amino acid residue of a peptide linker covalently attached to a protein/polypeptide carrier, R is a capping molecule covalently attached to the derivatized functional group of an amino acid residue of the protein/polypeptide carrier or optionally of an amino acid residue of a peptide linker covalently attached to a protein/polypeptide carrier thereby preserving the functionality of the carrier, such that it retains its ability to elicit the desired immune responses against the peptide immunogen that would otherwise not occur without a carrier, n is an integer greater than 0, but less than or equal to 85, and p is an integer greater than 0, but less than 85.

The detailed embodiments for the second method described above are also applicable to the conjugates generated by the second method, as just described.

In another embodiment, the invention is directed to immunogenic compositions comprising a conjugate of a peptide immunogen with a protein/polypeptide carrier generated by the second method of the invention, together with one or more pharmaceutically acceptable excipients, diluents, and adjuvants.

The detailed embodiments for the second method and the conjugates generated thereby described above are also applicable to immunogenic compositions containing those conjugates as just described.

In another embodiment, the invention is directed to a method for inducing an immune response in a mammalian subject, which comprises administering an effective amount of an immunogenic composition of the present invention to the subject.

The detailed embodiments applicable to the immunogenic composition containing the conjugates of the present invention are also applicable to the embodiment of the invention directed to the method of use of these immunogenic compositions.

BRIEF DESCRIPTION OF SEQUENCES

Figure 1:
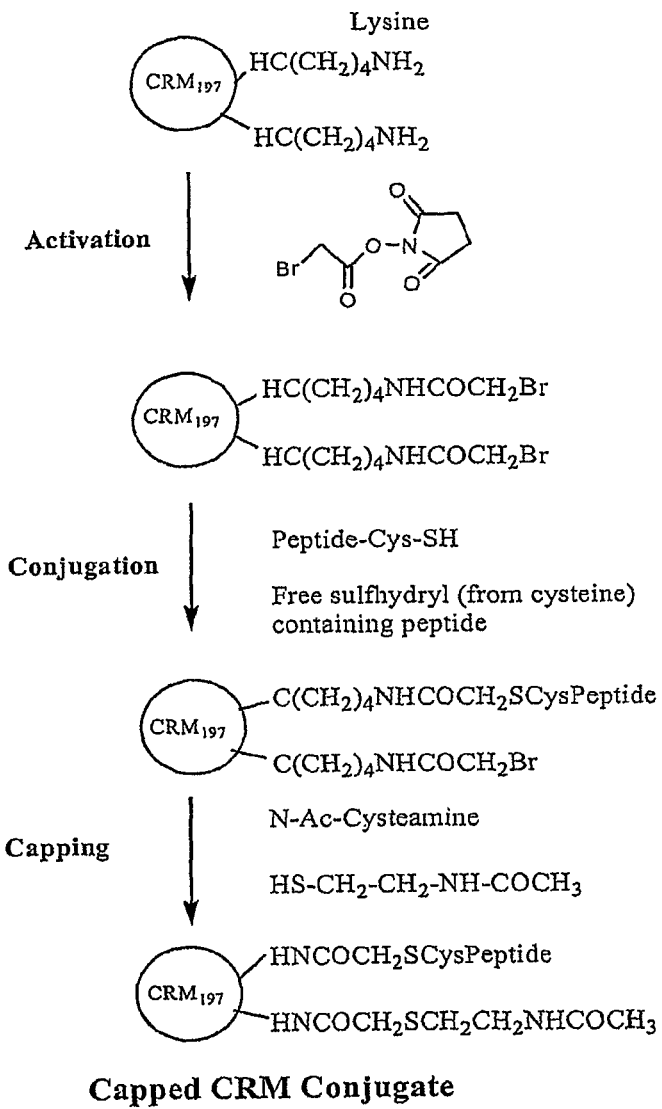
FIG. 1: Flow chart depicting the process chemistry used for conjugation of Aβ peptide fragments to protein/polypeptide carrier $CRM_{197}$ to form the $Aβ/CRM_{197}$ conjugate.

| SEQ ID NO: | Sequence | Description |
|---|---|---|
| 1 | DAEFR-C | Aβ1-5-C |
| 2 | DAEFRHD-C | Aβ1-7-C |
| 3 | DAEFRHDSG-C | Aβ1-9-C |
| 4 | DAEFRHDSGYEV-C | Aβ1-12-C |
| 5 | DAEFR-GAGA-C | Aβ1-5-L-C |
| 6 | DAEFRHD-GAGA-C | Aβ1-7-L-C |
| 7 | DAEFRHDSG-GAGA-C | Aβ1-9-L-C |
| 8 | DAEFRHDSGYEV-GAGA-C | Aβ1-12-L-C |
| 9 | VEYGSDHRFEAD-C | Aβ12-1-C |
| 10 | GAGA | Linker peptide |
| 11 | PKYVKQNTLKLAT | Influenza Hemagglutinin: HA$_{307-319}$ |
| 12 | AKXVAAWTLKAAA | PAN-DR Peptide (PADRE peptide) |
| 13 | EKKIAKMEKASSVFNV | Malaria CS: T3 epitope |
| 14 | FELLTRILTI | Hepatitis B surface antigen: HB$_s$Ag$_{19-28}$ |
| 15 | DQSIGDLIAEAMDKVGNEG | Heat Shock Protein 65: hsp65$_{153-171}$ |
| 16 | QVHFQPLPPAVVKL | Bacillus Calmette-Guerin (BCG) |
| 17 | QYIKANSKFIGITEL | Tetanus toxoid: TT$_{830-844}$ |
| 18 | FNNFTVSFWLRVPKVSASHLE | Tetanus toxoid: TT$_{947-967}$ |
| 19 | KQIINMWQEVGKAMY | HIV gp120 T1 |
| 20 | DAEFRHD-QYIKANSKFIGITEL-C-FNNFTVSFWLRVPKVSASHLE-DAEFRED | Aβ$_{1-7}$/TT$_{830-844}$/C/TT$_{947-967}$/Aβ$_{1-7}$ |
| 21 | DAEFRHDSGYEVHHQKLVFFAEDVGSNKGAIIGLMVGGVVIA | Aβ$_{1-42}$ |
| 22 | DAEFRHDQYEKANSKFIGITEL | AN90549: Aβ$_{1-7}$/TT$_{830-844}$ (used in a MAP4 configuration) |
| 23 | DAEFRHDFNNFTVSFWLRVPKVSASHLE | AN90550: Aβ$_{1-7}$/TT$_{947-967}$ (used in a MAP4 configuration) |

-continued

| SEQ ID NO: | Sequence | Description |
|---|---|---|
| 24 | DAEFRHD-QYIKANSKFIGITELFNNFTVSFWLRVPKVSASHLE | AN90542: $A\beta_{1-7}/TT_{830-844}$ + $TT_{947-967}$ (used in a linear configuration) |
| 25 | EFRHDSG-QYIKANSKFIGITEL | AN90576: $A\beta_{3-9}/TT_{830-844}$ (used in a MAP4 configuration) |
| 26 | AKXVAAWTLKAAA-DAEFRHD | AN90562: $A\beta_{1-7}$/PADRE |
| 27 | DAEFRHD-DAEFRHDD-AEFRHDAKXVAAWTLKAAA | AN90543: $A\beta_{1-7} \times 3$/PADRE |
| 28 | AKXVAAWTLKAAA-DAEFRHD-DAEFRHD-DAEFRHD | PADRE/$A\beta_{1-7} \times 3$ |
| 29 | DAEFRHD-AKXVAAWTLKAAA | $A\beta_{1-7} \times 3$/PADRE |
| 30 | DAEFRHD-ISQAVHAAHAEINEAGR | $A\beta_{1-7}$/albumin fragment |
| 31 | FRHDSGY-ISQAVHAAHAEINEAGR | $A\beta_{4-10}$/albumin fragment |
| 32 | EFRHDSG-ISQAVHAAHAEINEAGR | $A\beta_{3-9}$/albumin fragment |
| 33 | PKYVKQNTLKLAT-DAEFRHD-DAEFRHD-DAEFRHD | $HA_{307-319}/A\beta_{1-7} \times 3$ |
| 34 | DAEFRHD-PKYVKQNTLKLAT-DAEFRHD | $A\beta_{1-7}/HA_{307-319}/A\beta_{1-7}$ |
| 35 | DAEFRHD-DAEFRHD-DAEFRHD-PKYVKQNTLKLAT | $A\beta_{1-7} \times 3/HA_{307-319}$ |
| 36 | DAEFRHD-DAEFRHD-PKYVKQNTLKLAT | $A\beta_{1-7} \times 2/HA_{307-319}$ |
| 37 | DAEFRHD-PKYVKQNTLKLAT-EKKIAKMEKASSVFNV-QYIKANSKFIGITEL-FNNFTVSFWLRVPKVSASHLE-DAEFRHD | $A\beta_{1-7}/HA_{307-319}$/Malaria CS/$TT_{830-844}/TT_{947-967}/A\beta_{1-7}$ |
| 38 | DAEFRHD-DAEFRHD-DAEFRHD-QYIKANSKFIGITEL-C-FNNFTVSFWLRVPKVSASHLE | $A\beta_{1-7} \times 3/TT_{830-844}/C/TT_{947-967}$ |
| 39 | DAEFRHD-QYIKANSKFIGITEL-C-FNNFTVSFWLRVPKVSASHLE | $A\beta_{1-7}/TT_{830-844}/C/TT_{947-967}$ |
| 40 | GADDVVDSSKSFVMENFSSYHGTKPGYVDSIQKGIQKPKSGTQGNYDDDWKEFYSTDNKYDAAGYSVDNENPLSGKAGGVVKVTYPGLTKVLALKVDNAETIKKELGLSLTEPLMEQVGTEEFIKRFGDGASRVVLSLPFAEGSSSVEYINNWEQAKALSVELEINFETRGKRGQDAMYEYMAQACAGNRVRRSVGSSLSCINLDWDVIRDKTKTKIESLKEHGPIKNKMSESPNKTVSEEKAKQYLEEFHQTALEHPELSELKTVTGTNPVFAGANYAAWAVNVAQVIDSETADNLEKTTAALSILPGIGSVMGIADGAVHHNTEEIVAQSIALSSLMVAQAIPLVGELVDIGFAAYNFVESIINLFQVVHNSYNRPAYSPGHKTQPFLHDGYAVSWNTVEDSIIRTGFQGESGHDIKITAENTPLPIAGVLLPTIPGKLDVNKSKTHISVNGRKIRMRCRAIDGDVTFCRPKSPVYVGNGVHANLHVAFHRSSSEKIHSNEISSDSIGVLGYQKTVDHTKVNSKLSLFFEIKS | $CRM\beta_{197}$ |
| 41 | ISQAVHAAHAEINEAGR | Albumin fragment |
| 42 | DAEFGHDSGFEVRHQKLVFFAEDVGSNKGAIIGLMVGGVVIA | Murine $A\beta1-42$ |

| SEQ ID NO: | Sequence | Description |
|---|---|---|
| 43 | VFFAEDVG-C | Aβ18-25-C |
| 44 | LVFFAEDV-C | Aβ17-24-C |
| 45 | KLVFFAED-C | Aβ16-23-C |
| 46 | C-VFFAEDVG | C-Aβ18-25 |
| 47 | C-LVFFAEDV | C-Aβ17-24 |
| 48 | C-KLVFFAED | C-Aβ16-23 |
| 49 | VFFAEDV-C | Aβ18-24-C |
| 50 | LVFFAED-C | Aβ17-23-C |
| 51 | KLVFFAE-C | Aβ16-22-C |
| 52 | C-VFFAEDV | C-A$\beta_{18-24}$ |
| 53 | C-LVFFAED | C-A$\beta_{17-23}$ |
| 54 | C-KLVFFAE | C-A$\beta_{16-22}$ |

DETAILED DESCRIPTION OF THE INVENTION

The present invention is directed to methods of generating peptide immunogen-carrier conjugates wherein the unreacted active functional groups on the carrier which are generated during activation are inactivated by using capping reagents such as N-Acetylcysteamine in order to prevent them from reacting further. The present invention is also directed to capped carrier-peptide immunogen conjugates generated by those methods and to immunogenic compositions comprising said conjugates.

The approach of increasing immunogenicity of small or poorly immunogenic molecules, such as saccharides, through conjugation has been utilized successfully for decades (see, e.g., Goebel et al. (1939) *J. Exp. Med.* 69: 53), and many immunogenic compositions have been described in which purified capsular polymers have been conjugated to carrier proteins to create more effective immunogenic compositions by exploiting this "carrier effect". For example, Schneerson et al. (*J. Exp. Med.* 152: 361-376, 1980), describe *Haemophilus influenzae* b polysaccharide protein conjugates that confer immunity to invasive diseases caused by that microorganism. Conjugates of PRP (polyribosylribitol phosphate, a capsular polymer of *H. influenzae* b) have been shown to be more effective than immunogenic compositions based on the polysaccharide alone (Chu et al., (1983) *Infect. Immun.* 40: 245; Schneerson et al. (1984), *Infect. Immun.* 45: 582-591). Conjugation has also been shown to bypass the poor antibody response usually observed in infants when immunized with a free polysaccharide (Anderson et al. (1985) *J. Pediatr.* 107: 346; Insel et al. (1986) *J. Exp. Med.* 158: 294).

A further advantage of using as the protein carrier a bacterial toxin or toxoid against which routine immunization of humans (e.g., tetanus or diphtheria) is a standard practice is that a desired immunity to the toxin or toxoid is induced along with immunity against the pathogens associated with the capsular polymer.

Antigenic determinant/hapten-carrier conjugates also are being used to produce highly specific monoclonal antibodies that can recognize discrete chemical epitopes on the coupled hapten. The resulting monoclonals often are used to investigate the epitopic structure and interactions between native proteins. In many cases, the antigenic determinants/haptens used to generate these monoclonals are small peptide segments representing crucial antigenic sites on the surface of larger proteins. The criteria for a successful carrier to be used in generating an antigenic determinant/hapten-carrier conjugate are the potential for immunogenicity, the presence of suitable functional groups for conjugation with an antigenic determinant/hapten, reasonable solubility properties even after derivatization and lack of toxicity in vivo.

These criteria are met by the conjugates generated by the methods of the instant invention. The conjugates may be any stable peptide immunogen-carrier conjugates generated using the conjugation process described herein. The conjugates are generated using a process of the instant invention wherein a protein/polypeptide carrier having the following structure:

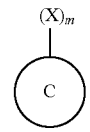

is covalently attached to a protein/polypeptide carrier, wherein,

C is a protein/polypeptide carrier and X is a derivatizable functional group on an amino acid residue on the protein/polypeptide carrier or optionally on an amino acid residue on a peptide linker covalently attached to the protein/polypeptide carrier, and wherein m is an integer greater than 0, but less than or equal to 85, is covalently attached to a peptide immunogen and wherein the peptide immunogen-protein/polypeptide carrier conjugate has the following formula, is represented by the following formula:

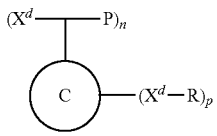

wherein,

C is the protein/polypeptide carrier and $X^d$ is a derivatized functional group on an amino acid residue on the protein/polypeptide carrier or optionally on an amino acid residue on a peptide linker covalently attached to the protein/polypeptide carrier, P is a peptide immunogen covalently attached to the derivatized functional group on the amino acid residue on the protein/polypeptide carrier or optionally on an amino acid residue on a peptide linker covalently attached to a protein/polypeptide carrier, R is a capping molecule covalently attached to the derivatized functional group on an amino acid residue on the protein/polypeptide carrier or optionally on an amino acid residue on a peptide linker covalently attached to a protein/polypeptide carrier thereby preserving the functionality of the carrier, such that it retains its ability to elicit the desired immune responses against the peptide immunogen that would otherwise not occur without a carrier, n is an integer greater than 0, but less than or equal to 85, and p is an integer greater than 0, but less than 85.

Selection of Carriers

Some peptide immunogens contain the appropriate epitope for inducing an immune response, but are too small to be immunogenic. In this situation, the peptide immunogens are linked to a suitable carrier to help elicit an immune response. In the above schematic representation of the peptide immunogens-carrier conjugate generated by a process of the present invention, C is a protein/polypeptide carrier to which peptide immunogens are conjugated directly via derivatized functional groups on amino acid residues on the carrier themselves or indirectly via derivatized functional groups on peptide linkers covalently attached to the carriers. Suitable protein/polypeptide carriers include, but are not limited to, albumin (including humanserum albumin), keyhole limpet hemocyanin, immunoglobulin molecules, thyroglobulin, ovalbumin, MSCRAMMS, tetanus toxoid, or a toxoid from other pathogenic bacteria having reduced toxicity, including mutants, such as diphtheria, *E. coli*, cholera, or *H. pylori*, or an attenuated toxin derivative. One such carrier is the $CRM_{197}$ protein (SEQ ID NO.:40) that is cross-reactive with diphtheria toxin.

Other carriers include T-cell epitopes that bind to multiple MHC alleles, e.g., at least 75% of all human MHC alleles. Such carriers are sometimes known in the art as "universal T-cell epitopes." Exemplary carriers with universal T-cell epitopes include:

```
                                          (SEQ. ID NO. 11)
Influenza Hemagglutinin: HA307-319
PKYVKQNTLKLAT (SEQ. ID NO. 12)
PAN-DR Peptide (PADRE peptide)
AKXVAAWTLKAAA (SEQ. ID NO. 13)
Malaria CS: T3 epitope
EKKIAKMEKASSVFNV (SEQ. ID NO. 14)
Hepatitis B surface antigen: HBsAg19-28
FELLTRILTI (SEQ. ID NO. 15)
Heat Shock Protein 65: hsp65153-171
QSIGDLIAEAMDKVGNEG (SEQ. ID NO. 16)
Bacillus Calmette-Guerin (BCG)
QVHFQPLPPAVVKL (SEQ. ID NO. 17)
Tetanus toxoid: TT830-844
QYIKANSKFIGITEL (SEQ. ID NO. 18)
Tetanus toxoid: TT947-967
NNFTVSFWLRVPKVSASHLE (SEQ. ID NO. 19)
HIV gp120 T1:
KQIINMWQEVGKAMY (SEQ ID NO.: 40)
CRM197
See the Brief Description of the Sequences (SEQ ID NO: 41)
Albumin fragment
ISQAVHAAHAEINEAGR
```

Other carriers for stimulating or enhancing an immune response and to which a peptide immunogen or a hapten can be conjugated include cytokines such as IL-1, IL-1 α and β peptides, IL-2, γINF, IL-10, GM-CSF, and chemokines, such as MIP 1α and β and RANTES. Immunogenic peptides can also be linked to proteins/peptide carriers that enhance transport across tissues, as described in O'Mahony, WO 97/17163 and WO 97/17614, which are hereby incorporated by reference in their entirety for all purposes.

Still further carriers include recombinant Streptococcal C5a peptidase, *Streptococcus pyogenes* ORFs 1224, 1664 and 2452, *Chlamydia pneumoniae* ORFs T367 and T858, *Streptococcus pneumonia* pneumolysin, pneumolysin mutants with reduced toxicity, growth factors, and hormones.

In one preferred embodiment of the present invention, the carrier protein is $CRM_{197}$, a non-toxic mutant of diphtheria toxin with one amino acid change in its primary sequence. The glycine present at the amino acid position 52 of the molecule is replaced with a glutamic acid due to a single nucleic acid codon change. Due to this change, the protein lacks ADP-ribosyl transferase activity and becomes non-toxic. It has a molecular weight of 58,408 Da. $CRM_{197}$ is produced in large quantities by recombinant expression in accordance with U.S. Pat. No. 5,614,382, which is hereby incorporated by reference. Conjugations of saccharides as well as peptides to $CRM_{197}$ are carried out by linking through the ε-amino groups of lysine residues. It has been well established through several commercial products that $CRM_{197}$ is an excellent and safe carrier for B-cell epitopes.

Immunogenic Peptides

As used herein, the term "peptide immunogen" or "hapten" is any protein or subunit structure/fragment/analog derived therefrom that can elicit, facilitate, or be induced to produce an immune response on administration to a mammal. In particular, the term is used to refer to a polypeptide antigenic determinant from any source (bacteria, virus or eukaryote), which may be coupled to a carrier using a method disclosed herein. Such polypeptide immunogen/antigenic determinants may be of viral, bacterial or eukaryotic cell origin.

Peptide immunogens can be conjugated to a carrier for use as an immunotherapeutic in the prevention, treatment, prophylaxis or amelioration of various human diseases. Such peptide immunogens include those derived from Aβ a peptide of 39-43 amino acids, preferably 42 amino acids, which is the principal component of characteristic plaques of Alzheimer's disease (AD) (see U.S. Pat. No. 4,666,829; Glenner & Wong (1984) *Biochem. Biophys. Res. Commun.* 120: 1131, Hardy (1984) *TINS* 20: 1131; Hardy (1977) *TINS* 20: 154), those derived from amyloid peptides of amylin, a polypeptide material produced by pancreatic islet cells that has been implicated in type II diabetes, peptides derived from low density lipoprotein gene products, which have been implicated in atherosclerosis and antigenic peptides derived from inflammatory cytokines and growth factors such as interleukin 6 (IL-6), tumor necrosis factor α (TNF-α) and GDF-8. Such eukaryotic peptide immunogens may include either T-cell (CTL) or B-cell epitope, also known as β-amyloid protein, or A4 peptide.

Aβ, also known as β-amyloid peptide, or A4 peptide (see U.S. Pat. No. 4,666,829; Glenner & Wong, *Biochem. Biophys. Res. Commun.*, 120, 1131 (1984)), is a peptide of 39-43 amino acids, which is the principal component of characteristic plaques of Alzheimer's disease. Aβ is generated by processing of a larger protein APP by two enzymes, termed β and γ secretases (see Hardy, *TINS* 20, 154 (1997)). Known mutations in APP associated with Alzheimer's disease occur proximate to the site of β or γ secretase, or within Aβ. For example, position 717 is proximate to the site of γ-secretase cleavage of APP in its processing to Aβ, and positions 670/671 are proximate to the site of β-secretase cleavage. It is believed that the mutations cause AD by interacting with the cleavage reactions by which Aβ is formed so as to increase the amount of the 42/43 amino acid form of Aβ generated.

Aβ has the unusual property that it can fix and activate both classical and alternate complement cascades. In particular, it binds to C1q and ultimately to C3bi. This association facilitates binding to macrophages leading to activation of B cells. In addition, C3bi breaks down further and then binds to CR2 on B cells in a T cell dependent manner leading to a 10,000-fold increase in activation of these cells. This mechanism causes Aβ to generate an immune response in excess of that of other antigens.

Aβ has several natural occurring forms. The human forms of Aβ are referred to as Aβ39, Aβ40, Aβ41, Aβ42 and Aβ43. The sequences of these peptides and their relationship to the APP precursor are illustrated by FIG. 1 of Hardy et al., TINS 20, 155-158 (1997). For example, Aβ42 has the sequence:

(SEQ ID NO. 21)
H₂N-Asp-Ala-Glu-Phe-Arg-His-Asp-Ser-Gly-Tyr-Glu-

Val-His-His-Gln-Lys-Leu-Val-Phe-Phe-Ala-Glu-Asp-

Val-Gly-Ser-Asn-Lys-Gly-Ala-Ile-Ile-Gly-Leu-Met-

Val-Gly-Gly-Val-Val-Ile-Ala-OH.

Aβ41, Aβ40 and Aβ39 differ from Aβ42 by the omission of Ala, Ala-Ile, and Ala-Ile-Val respectively from the C-terminal end. Aβ43 differs from Aβ42 by the presence of a threonine residue at the C-terminus.

Peptide immunogens which are fragments of Aβ are advantageous relative to the intact molecule for use in the present methods for several reasons. First, because only certain epitopes within Aβ induce a useful immunogenic response for treatment of Alzheimer's disease, an equal dosage of mass of a fragment containing such epitopes provides a greater molar concentration of the useful immunogenic epitopes than a dosage of intact Aβ. Second, certain peptide immunogens of Aβ generate an immunogenic response against amyloid deposits without generating a significant immunogenic response against APP protein from which Aβ derives. Third, peptide immunogens of Aβ are simpler to manufacture than intact Aβ due to their shorter size. Fourth, peptide immunogens of Aβ do not aggregate in the same manner as intact Aβ, simplifying preparation of conjugates with carriers.

Some peptide immunogens of Aβ have a sequence of at least 2, 3, 5, 6, 10, or 20 contiguous amino acids from a natural peptide. Some peptide immunogens have no more than 10, 9, 8, 7, 5 or 3 contiguous residues from Aβ. In a preferred embodiment, peptide immunogens from the N-terminal half of Aβ are used for preparing conjugates. Preferred peptide immunogens include Aβ1-5, 1-6, 1-7, 1-10, 1-11, 3-7, 1-3, and 1-4. The designation Aβ1-5 for example, indicates an N-terminal fragment including residues 1-5 of Aβ. Aβ fragments beginning at the N-terminus and ending at a residue within residues 7-11 of Aβ are particularly preferred. The fragment Aβ1-12 can also be used but is less preferred. In some methods, the fragment is an N-terminal fragment other than Aβ1-10. Other preferred fragments include Aβ13-28, 15-24, 1-28, 25-35, 35-40, 35-42 and other internal fragments and C-terminus fragments.

Some Aβ peptides of the invention are immunogenic peptides that on administration to a human patient or animal generate antibodies that specifically bind to one or more epitopes between residues 16 and 25 of Aβ. Preferred fragments include Aβ16-22, 16-23, 17-23, 17-24, 18-24, and 18-25. Antibodies specifically binding to epitopes between residues 16 and 25 specifically bind to soluble Aβ without binding to plaques of Aβ. These types of antibody can specifically bind to soluble Aβ in the circulation of a patient or animal model without specifically binding to plaques of Aβ deposits in the brain of the patient or model. The specific binding of antibodies to soluble Aβ inhibits the Aβ from being incorporated into plaques thus either inhibiting development of the plaques in a patient or inhibiting a further increase in the size or frequency of plaques if such plaques have already developed before treatment is administered.

Preferably, the fragment of Aβ administered lacks an epitope that would generate a T-cell response to the fragment. Generally, T-cell epitopes are greater than 10 contiguous amino acids. Therefore, preferred fragments of Aβ are of size 5-10 or preferably 7-10 contiguous amino acids or most preferably 7 contiguous amino acids; i.e., sufficient length to generate an antibody response without generating a T-cell response. Absence of T-cell epitopes is preferred because these epitopes are not needed for immunogenic activity of fragments, and may cause an undesired inflammatory response in a subset of patients (Anderson et al., (2002) *J. Immunol.* 168, 3697-3701; Senior (2002) Lancet *Neurol.* 1, 3).

Fragment Aβ15-25 and subfragments of 7-8 contiguous amino acids thereof are preferred because these peptides consistently generate a high immunogenic response to Aβ peptide. These fragments include Aβ16-22, Aβ16-23, Aβ16-24, Aβ17-23, Aβ17-24, Aβ18-24, and Aβ18-25. Particularly preferred Aβ15-25 subfragments are 7 contiguous amino acids in length. The designation Aβ15-21 for example, indicates a fragment including residues 15-21 of Aβ and lacking other residues of Aβ, and preferably 7-10 contiguous amino acids. These fragments can generate an antibody response that includes end-specific antibodies.

Peptide immunogens of Aβs require screening for activity in clearing or preventing amyloid deposits (see WO 00/72880, which is incorporated herein in its entirety for all purposes). Administration of N-terminal fragments of Aβ induces the production of antibodies that recognize Aβ deposits in vivo and in vitro. Fragments lacking at least one, and sometimes at least 5 or 10 C-terminal amino acids present in naturally occurring forms of Aβ are used in some methods. For example, a fragment lacking 5 amino acids from the C-terminal end of Aβ43 includes the first 38 amino acids from the N-terminal end of Aβ.

Unless otherwise indicated, reference to Aβ includes the natural human amino acid sequences indicated above as well as analogs including allelic, species and induced variants. Analogs typically differ from naturally occurring peptides at one, two or a few positions, often by virtue of conservative substitutions. Analogs typically exhibit at least 80 or 90% sequence identity with natural peptides. Some analogs also include unnatural amino acids or modifications of N- or C-terminal amino acids at one, two, or a few positions. For example, the natural aspartic acid residue at position 1 and/or 7 of Aβ can be replaced with iso-aspartic acid.

Examples of unnatural amino acids are D, alpha, alpha-disubstituted amino acids, N-alkyl amino acids, lactic acid, 4-hydroxyproline, gamma-carboxyglutamate, epsilon-N,N, N-trimethyllysine, epsilon-N-acetyllysine, O-phosphoserine, N-acetylserine, N-formylmethionine, 3-methylhistidine, 5-hydroxylysine, omega-N-methylarginine, β-alanine, ornithine, norleucine, norvaline, hydroxproline, thyroxine, gamma-amino butyric acid, homoserine, citrulline, and isoaspartic acid. Immunogenic peptides also include analogs of Aβ and fragments thereof. Some therapeutic agents of the invention are all-D peptides, e.g., all-D Aβ, all-D Aβ fragment, or analogs of all-D Aβ or all-D Aβ fragment. Fragments and analogs can be screened for prophylactic or therapeutic efficacy in transgenic animal models in comparison with untreated or placebo controls as described in WO 00/72880.

Peptide immunogens also include longer polypeptides that include, for example, an immunogenic of Aβ peptide, together with other amino acids. For example, preferred immunogenic peptides include fusion proteins comprising a segment of Aβ linked to a heterologous amino acid sequence that induces a helper T-cell response against the heterologous amino acid sequence and thereby a B-cell response against the Aβ segment. Such polypeptides can be screened for prophylactic or therapeutic efficacy in animal models in comparison with untreated or placebo controls as described in WO 00/72880.

The Aβ peptide, analog, immunogenic fragment or other polypeptide can be administered in disaggregated or aggregated form. Disaggregated Aβ or fragments thereof means monomeric peptide units. Disaggregated Aβ or fragments thereof are generally soluble, and are capable of self-aggregating to form soluble oligomers, protofibrils and ADDLs. Oligomers of Aβ and fragments thereof are usually soluble and exist predominantly as alpha-helices or random coils. Aggregated Aβ or fragments thereof means oligomers of Aβ or fragments thereof that have associate into insoluble beta-sheet assemblies. Aggregated Aβ or fragments thereof also means fibrillar polymers. Fibrils are usually insoluble. Some antibodies bind either soluble Aβ or fragments thereof or aggregated Aβ or fragments thereof. Some antibodies bind both soluble Aβ or fragments thereof and aggregated Aβ or fragments thereof.

Immunogenic peptides also include multimers of monomeric immunogenic peptides. Immunogenic peptides other than Aβ peptides should induce an immunogenic response against one or more of the preferred fragments of Aβ listed above (e.g., Aβ1-3, 1-7, 1-10, and 3-7).

Immunogenic peptides of the present invention are linked to a carrier using a method of the present invention to form a conjugate. The immunogenic peptide can be linked at its amino terminus, its carboxyl terminus, or both to a carrier to form a conjugate. Optionally, multiple repeats of the immunogenic peptide can be present in the conjugate.

An N-terminal fragment of Aβ can be linked at its C-terminus to a carrier peptide to form a conjugate. In such conjugates, the N-terminal residue of the fragment of Aβ constitutes the N-terminal residue of the conjugate. Accordingly, such conjugates are effective in inducing antibodies that bind to an epitope that requires the N-terminal residue of Aβ to be in free form. Some immunogenic peptides of the invention comprise a plurality of repeats of an N-terminal segment of Aβ linked at the C-terminus to one or more copy of a carrier peptide to form a conjugate. The N-terminal fragment of Aβ incorporated into such conjugates sometimes begins at Aβ1-3 and ends at Aβ7-11. Aβ1-7, 1-3, 1-4, 1-5, and 3-7 are preferred N-terminal fragment of Aβ. Some conjugates comprise different N-terminal segments of Aβ in tandem. For example, a conjugate can comprise Aβ1-7 followed by Aβ1-3 linked to a carrier.

In some conjugates, an N-terminal segment of Aβ is linked at its N-terminal end to a carrier peptide. The same variety of N-terminal segments of Aβ can be used as with C-terminal linkage. Some conjugates comprise a carrier peptide linked to the N-terminus of an N-terminal segment of Aβ, which is in turn linked to one or more additional N-terminal segments of Aβ in tandem. Preferably, such immunogenic Aβ fragments, once conjugated to an appropriate carrier, induce an immunogenic response that is specifically directed to the Aβ fragment without being directed to other fragments of Aβ.

Immunogenic peptides of the invention include immunogenic heterologous peptides. In some immunogenic peptides, an Aβ fragment is linked to a carrier to form an immunogenic heterologous peptide. This heterologous peptide is linked to a carrier using a method of the present invention to form a conjugate. Some of these immunogenic heterologous peptides comprise fragments of Aβ linked to tetanus toxoid epitopes such as described in U.S. Pat. No. 5,196,512, EP 378,881 and EP 427,347. Optionally, an immunogenic peptide can be linked to one or multiple copies of a carrier, for example, at both the N and C termini of the carrier to form an immunogenic heterologous peptide. Other of these immunogenic heterologous peptides comprise fragments of Aβ linked to carrier peptides described in U.S. Pat. No. 5,736,142. For example, an immunogenic heterologous peptide can comprise Aβ1-7 followed by Aβ1-3 followed by a carrier. Examples of such immunogenic heterologous peptides include:

```
Aβ 1-7/Tetanus toxoid 830-844 + 947-967 in a
linear configuration
                                    (SEQ ID NO.: 24)
DAEFRHD-QYIKANSKFIGITELFNNFTVSFWLRVPKVSASHLE Peptides described in U.S. Pat. No. 5,736,142
(all in linear configurations):
PADRE/Aβ 1-7:
                                    (SEQ ID NO.: 26)
AKXVAAWTLKAAA-DAEFRHD Aβ1-7 x 3/PADRE:
                                    (SEQ ID NO.: 27)
DAEFRHD-DAEFRHD-DAEFRHD-AKXVAAWTLKAAA PADRE/Aβ1-7 x 3:
                                    (SEQ ID NO.: 28)
AKXVAAWTLKAAA-DAEFRHD-DAEFRHD-DAEFRHD Aβ1-7/PADRE:
                                    (SEQ ID NO.: 29)
DAEFRHD-AKXVAAWTLKAAA
```

-continued

Aβ1-7/albumin fragment:
(SEQ ID NO.: 30)
DAEFRHD-ISQAVHAAHAEINEAGR

Aβ4-10/albumin fragment:
(SEQ ID NO.: 31)
FRHDSGY-ISQAVHAAHAEINEAGR

Aβ3-9/albumin fragment:
(SEQ ID NO.: 32)
EFRHDSG-ISQAVHAAHAEINEAGR $HA_{307-319}/A\beta_{1-7} \times 3$:
(SEQ ID NO.: 33)
PKYVKQNTLKLAT-DAEFRHD-DAEFRHD-DAEFRHD $A\beta_{1-7}/HA_{307-319}/A\beta_{1-7}$:
(SEQ ID NO.: 34)
DAEFRHD-PKYVKQNTLKLAT-DAEFRHD $A\beta_{1-7} \times 3/HA_{307-319}$:
(SEQ ID NO.: 35)
DAEFRHD-DAEFRHD-DAEFRHD-PKYVKQNTLKLAT $A\beta_{1-7} \times 2/HA_{307-319}$:
(SEQ ID NO.: 36)
DAEFRHD-DAEFRHD-PKYVKQNTLKLAT $A\beta_{1-7}/HA_{307-319}/Malaria\ CS/TT_{830-844}/TT_{947-967}/A\beta_{1-7}$
(SEQ ID NO.: 37)
DAEFRHD-PKYVKQNTLKLAT-EKKIAKMEKASSVFNV-
QYIKANSKFIGITEL-FNNFTVSFWLRVPKVSASHLE-DAEFRHD $A\beta_{1-7} \times 3/TT_{830-844}/C/TT_{947-967}$
(SEQ ID NO.: 38)
DAEFRHD-DAEFRHD-DAEFRHD-QYIKANSKFIGITEL-C-
FNNFTVSFWLRVPKVSASHLE $A\beta_{1-7}/TT_{830-844}/C/TT_{947-967}$
(SEQ ID NO.: 39)
DAEFRHD-QYIKANSKFIGITELCFNNFTVSFWLRVPKVSASHLE $A\beta_{1-7}/TT_{830-844}/C/TT_{947-967}/A\beta_{1-7}$
(SEQ ID NO.: 20)
DAEFRHD-QYIKANSKFIGITEL-C-FNNFTVSFWLRVPKVSASHLE-
DAEFRHD Some immunogenic heterologous peptides comprise a multimer of immunogenic peptides represented by the formula $2^x$, in which x is an integer from 1-5. Preferably x is 1, 2 or 3, with 2 being most preferred. When x is two, such a multimer has four immunogenic peptides linked in a preferred configuration referred to as MAP4 (see U.S. Pat. No. 5,229,490). Such immunogenic peptides are then linked to a carrier using a method of the present invention to form a conjugate.

The MAP4 configuration is shown below, where branched structures are produced by initiating peptide synthesis at both the N-terminal and side chain amines of lysine. Depending upon the number of times lysine is incorporated into the sequence and allowed to branch, the resulting structure will present multiple N-termini. In this example, four identical N-termini have been produced on the branched lysine-containing core. Such multiplicity greatly enhances the responsiveness of cognate B cells.

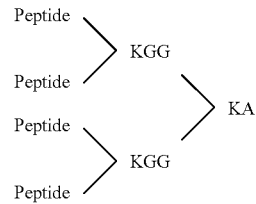

Examples of such immunogenic heterologous peptides include:

Aβ 1-7/Tetanus toxoid 830-844 in a MAP4
configuration:
(SEQ ID NO.: 22)
DAEFRHD-QYIKANSKFIGITEL Aβ 1-7/Tetanus toxoid 947-967 in a MAP4
configuration:
(SEQ ID NO.: 23)
DAEFRHD-FNNFTVSFWLRVPKVSASHLE Aβ 3-9/Tetanus toxoid 830-844 in a MAP4
configuration:
(SEQ ID NO.: 25)
EFRHDSG-QYIKANSKFIGITEL DAEFRHD-QYIKANSKFIGITEL on a 2 branched resin

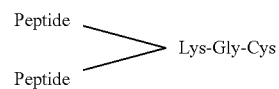

The Aβ peptide, analog, active fragment or other polypeptide can be administered in associated or multimeric form or in dissociated form. Therapeutic agents also include multimers of monomeric immunogenic agents. Agents other than Aβ peptides should induce an immunogenic response against one or more of the preferred fragments of Aβ listed above (e.g., 1-10, 1-7, 1-3, and 3-7), and can also be conjugated to a carrier using a method of the present invention. Preferably, such agents, once conjugated to an appropriate carrier, induce an immunogenic response that is specifically directed to one of these fragments without being directed to other fragments of Aβ. To facilitate the conjugation of an peptide immunogen with a carrier, additional amino acids can be added to the termini of the antigenic determinants. The additional residues can also be used for modifying the physical or chemical properties of the peptide immunogen. Amino acids such as tyrosine, cysteine, lysine, glutamic or aspartic acid, or the like, can be introduced at the C- or N-terminus of the peptide immunogen. Additionally, peptide linkers containing amino acids such as glycine and alanine can also be introduced. In addition, the antigenic determinants can differ from the natural sequence by being modified by terminal $NH_2$-group acylation, e.g., by alkanoyl (C1-C20) or thioglycolyl acetylation, terminal-carboxy amidation, e.g., ammonia, methylamine, etc. In some instances these modifications may provide sites for linking to a support or other molecule.

The peptide immunogens used to generate conjugates of the present invention using a process disclosed herein can be combined via linkage to form polymers (multimers), or can be formulated in a composition without linkage, as an admixture. Where a peptide is linked to an identical peptide, thereby forming a homopolymer, a plurality of repeating epitopic units are presented. For example, multiple antigen peptide (MAP) technology is used to construct polymers containing both CTL and/or antibody peptides and peptides. A "CTL epitope" is one derived from selected eptiopic regions of potential target antigens. When the peptides differ, e.g., a cocktail representing different viral subtypes, different epitopes within a subtype, different HLA restriction specificities, or peptides which contain T-helper epitopes, heteropolymers with repeating units are provided. In addition to covalent linkages, noncovalent linkages capable of forming intermolecular and intrastructural bonds are also contemplated.

Such peptide immunogens and their analogs are synthesized by solid phase peptide synthesis or recombinant expression, or are obtained from natural sources. Automatic peptide synthesizers are commercially available from numerous suppliers, such as Applied Biosystems, Foster City, Calif.

Recombinant expression can be in bacteria (such as *E. coli*), yeast, insect cells or mammalian cells. Procedures for recombinant expression are described by Sambrook et al., *Molecular Cloning: A Laboratory Manual* (Cold Spring Harbor Press, NY, 2nd ed., 1989). Some immunogenic peptides are also available commercially (e.g., American Peptides Company, Inc., Sunnyvale, Calif., and California Peptide Research, Inc., Napa, Calif.).

Random libraries of peptides or other compounds can also be screened for suitability as a peptide immunogen. Combinatorial libraries can be produced for many types of compounds that can be synthesized in a step-by-step fashion. Such compounds include polypeptides, beta-turn mimetics, hormones, oligomeric N-substituted glycines, and oligocarbamates and the like. Large combinatorial libraries of the compounds can be constructed by the encoded synthetic libraries (ESL) method described in WO 95/12608, WO 93/06121, WO 94/08051, WO 95/35503 and WO 95/30642 (each of which is incorporated by reference for all purposes). Peptide libraries can also be generated by phage display methods (see, e.g., Devlin, WO 91/18980).

Derivatization and Conjugation of an Immunogenic Peptide to a Protein Carrier

The site of attachment of a peptide immunogen to a protein/polypeptide carrier, and the nature of the cross-linking agent that is used to attach a peptide immunogen to the carrier are both important to the specificity of the resultant antibody generated against it. For proper recognition, the peptide immunogen must be coupled to the carrier with the appropriate orientation. For an antibody to recognize subsequently the free peptide immunogens without carrier, the peptide immunogen-protein/polypeptide carrier conjugate must present the peptide immunogens in an exposed and accessible form. Optimal orientation is often achieved by directing the cross-linking reaction to specific sites on the peptide immunogens. One way to achieve this with a peptide immunogen is by attaching a terminal cysteine residue during peptide synthesis. This provides a sulfhydryl group on one end of the peptide for conjugation to the carrier. Cross-linking through this group provides attachment of the peptide immunogen only at one end, thereby ensuring consistent orientation.

In peptide immunogen-carrier conjugation, the goal is not to maintain the native state or stability of the carrier, but to present the hapten in the best possible way to the immune system. In reaching this goal, the choice of conjugation chemistry may control the resultant titer, affinity, and specificity of the antibodies generated against the hapten. It may be important in some cases to choose a cross-linking agent containing a spacer arm long enough to present the antigen in an unrestricted fashion. It also may be important to control the density of the peptide immunogen on the surface of the carrier. Too little peptide immunogen substitution may result in little or no response. A peptide immunogen density too high actually may cause immunological suppression and decrease the response. In addition, the cross-linker itself may generate an undesired immune response. These issues need to be taken into consideration in selecting not only the appropriate cross-linking reagents, but also the appropriate ratios of protein/polypeptide carrier and peptide immunogen.

A variety of means of attaching the protein/peptide carriers to the peptide immunogens are possible. Ionic interactions are possible through the termini or through the ε-amino group of lysine. Hydrogen bonding between the side groups of the residues and the peptide immunogen are also possible. Finally, conformation interactions between the protein/peptide carriers and the immunogenic peptide may give rise to a stable attachment.

Peptide immunogens-carrier conjugates have been successfully generated using various cross-linking reagents such as zero-length, homobifunctional or heterobifunctional cross linkers. The smallest available reagent systems for bioconjugation are the so-called zero-length cross-linkers. These compounds mediate the conjugation of two molecules by forming a bond containing no additional atoms. Thus, one atom of a molecule is spacer. In many conjugation schemes, the final complex is bound together by virtue of chemical components that add foreign structures to the substances being cross-linked. In some applications, the presence of these intervening linkers may be detrimental to the intended use. For instance, in the preparation of peptide immunogen-carrier conjugates the complex is formed with the intention of generating an immune response to the attached hapten. Occasionally, a portion of the antibodies produced by this response will have specificity for the cross-linking agent used in the conjugation procedure. Zero-length cross-linking agents eliminate the potential for this type of cross-reactivity by mediating a direct linkage between two substances.

Homobifunctional reagents, which were the first cross-linking reagents used for modification and conjugation of macromolecules, consisted of bireactive compounds containing the same functional group at both ends (Hartman and Wold, 1966). These reagents could tie one protein to another by covalently reacting with the same common groups on both molecules. Thus, the lysine ε-amines or N-terminal amines of one protein could be cross-linked to the same functional groups on a second protein simply by mixing the two together in the presence of the homobifunctional reagent.

Heterobifunctional conjugation reagents contain two different reactive groups that can couple to two different functional targets on proteins and other macromolecules. For example, one part of a cross-linker may contain an amine-reactive group, while another portion may consist of a sulfhydryl-reactive group. The result is the ability to direct the cross-linking reaction to selected parts of target molecules, thus garnering better control over the conjugation process.

Heterobifunctional reagents are used to cross-link proteins and other molecules in a two- or three-step process that limits the degree of polymerization often obtained using homobifunctional cross-linkers.

Many methods are currently available for coupling of peptide immunogens to protein/polypeptide carriers using zero-length, homobifunctional or heterobifunctional crosslinkers. Most methods create amine, amide, urethane, isothiourea, or disulfide bonds, or in some cases thioethers. The more general method of coupling proteins or peptides to peptides utilizes bifunctional crosslinking reagents. These are small spacer molecules having active groups at each end. The spacer molecules can have identical or different active groups at each end. The most common active functionalities, coupling groups, and bonds formed are:
1. Aldehyde-amino→secondary amine
2. Maleimido-sulfhydryl(thioether
3. Succinimido-amino(amide
4. Imidate esters-amino(-amide
5. Phenyl azides-amino(phenyl amine
6. Acyl halide-sulfhydryl(thioether
7. Pyridyldisulfides-sulfhydryl(disulfide
8. Isothiocyanate-amino(isothiourea.

The reactivity of a given carrier protein, in terms of its ability to be modified by a cross-linking agent such that it can be conjugated to an peptide immunogen, is determined by its amino acid composition and the sequence location of the individual amino acids in the three dimensional structure of the molecule, as well as by the amino acid composition of the peptide immunogen.

In the case of linkers ("L") between protein/peptide carriers and other peptides (e.g., a protein/peptide carriers and an peptide immunogen), the spacers are typically selected from Ala, Gly, or other neutral spacers of nonpolar amino acids or neutral polar amino acids. In certain embodiments the neutral spacer is Ala. It will be understood that the optionally present spacer need not be comprised of the same residues and thus may be a hetero- or homo-oligomer. Exemplary spacers include homo-oligomers of Ala. When present, the spacer will usually be at least one or two residues, more usually three to six residues. In other embodiments the protein/polypeptide carrier is conjugated to an peptide immunogen, preferably with the protein/peptide carrier positioned at the amino terminus. The peptide may be joined by a neutral linker, such as Ala-Ala-Ala or the like, and preferably further contain a lipid residue such palmitic acid or the like which is attached to alpha and epsilon amino groups of a Lys residue ((PAM) 2Lys), which is attached to the amino terminus of the peptide conjugate, typically via Ser-Ser linkage or the like.

In some aspects of the invention, the peptide immunogen is an Aβ fragment selected from the group consisting of Aβ1-5-L, Aβ1-7-L, Aβ1-9-L, and Aβ1-12-L. In some aspects of the invention the linker is GAGA (SEQ ID NO:10).

To facilitate the conjugation of a peptide immunogen with a carrier, additional amino acids can be added to the termini of the antigenic determinants. The additional residues can also be used for modifying the physical or chemical properties of the peptide immunogen. Amino acids such as tyrosine, cysteine, lysine, glutamic or aspartic acid, or the like, can be introduced at the C- or N-terminus of the peptide immunogen. Additionally, peptide linkers containing amino acids such as glycine and alanine can also be introduced. In addition, the antigenic determinants can differ from the natural sequence by being modified by terminal $NH_2$-group acylation, e.g., by alkanoyl (C1-C20) or thioglycolyl acetylation, terminal-carboxy amidation, e.g., ammonia, methylamine, etc. In some instances these modifications may provide sites for linking to a support or other molecule.

In some aspects of the invention, the peptide immunogen is an Aβ fragment selected from the group consisting of Aβ1-5-C, Aβ1-7-C, Aβ1-9-C, and Aβ1-12-C, where C is a cysteine amino acid residue. In some aspects of the invention, the peptide immunogen is an Aβ fragment selected from the group consisting of Aβ1-5-L-C, Aβ1-7-L-C, Aβ1-9-L-C, and Aβ1-12-L-C.

The peptide immunogen is linked to the protein/peptide carrier either directly or via a linker either at the amino or carboxy terminus of the peptide immunogen. The amino terminus of either the peptide immunogen or the protein/peptide carrier may be acylated. In addition, the peptide immunogen-protein/peptide carrier conjugate may be linked to certain alkanyol ($C_1$-$C_{20}$) lipids via one or more linking residues such as Gly, Gly-Gly, Ser, Ser-Ser as described below. Other useful lipid moieties include cholesterol, fatty acids, and the like.

Peptide immunogens can be linked to a carrier by chemical crosslinking. Techniques for linking an immunogen to a carrier include the formation of disulfide linkages using N-succinimidyl-3-(2-pyridyl-thio) propionate (SPDP) (Carlsson, J et al. (1978) *Biochem J*, 173: 723) and succinimidyl 4-(N-maleimidomethyl)cyclohexane-1-carboxylate (SMCC) (if the peptide lacks a sulfhydryl group, this can be provided by addition of a cysteine residue to the hapten). These reagents create a disulfide linkage between themselves and peptide cysteine resides on one protein and an amide linkage through the ε-amino on a lysine, or other free amino group in other amino acids. A variety of such disulfide/amide-forming agents are described in Immuno. Rev. 62: 85 (1982). Other bifunctional coupling agents form a thioether rather than a disulfide linkage. The thioether forming agents include reactive ester of 6-maleimidocaproic acid, 2-bromoacetic acid, and 2-iodoacetic acid, 4-(N-maleimido-methyl)cyclohexane-1-carboxylic acid. The carboxyl groups can be activated by combining them with succinimide or 1-hydroxyl-2-nitro-4-sulfonic acid, sodium salt.

Most frequently, lysine residues are the most abundant amino acid residues found on carrier proteins, and these residues are modified using cross-linking reagents to generate neuclephilic sites that are then coupled to a hapten. This coupling is achieved via any of the hydrophilic side chains on the hapten molecules that are chemically active. These include the guanidyl group of arginine, the (-carboxyl groups of glutamate and aspartic acid, the sulfhydryl group of cysteine, and the ε-amino group of lysine, to name a few. Modification of proteins such that they can now be coupled to other moieties is achieved using crosslinking reagents, which react with any of the side chains on the protein carrier or hapten molecules.

In one aspect of the present invention, the carrier protein with or without a linker molecule is functionalized (derivatized) with a reagent that introduces reactive sites into the carrier protein molecule that are amenable to further modification to introduce nucleophilic groups. In one embodiment, the carrier is reacted with a haloacetylating reagent, which preferentially reacts with a number of functional groups on amino acid residues of proteins such as the sulfhydryl group of cysteine, the primary ε-amine group of lysine residue, the α terminal of α-amines, the thioether of methionine and both imidazoyl side chain nitrogens of histidine (Gurd, 1967). In a preferred embodiment, the primary ε-amine groups on lysine residues of the carrier protein are derivatized with b N-hydroxysuccinimidyl bromoacetate to generate a bromoacetylated carrier. Conjugation of peptide immunogen and the activated protein carrier was carried out by slowly adding the activated carrier to the solution containing the peptide immunogen.

By using the process of this invention, the peptide immunogens discussed in section B, above, may be conjugated to any of the carriers discussed in section A, above. The conjugates resulting from the process of this invention are used as immunogens for the generation of antibodies against Aβ for use in passive/active immunotherapy. Furthermore, Aβ or an Aβ fragment linked to a carrier can be administered to a laboratory animal in the production of monoclonal antibodies to Aβ.

In one aspect of the invention, the conjugate is a conjugate selected from the group consisting of Aβ1-7-$CRM_{197}$, (Aβ1-

7×3)-CRM$_{197}$, and (Aβ1-7×5)-CRM$_{197}$. In one aspect of the invention, the conjugate is a conjugate selected from the group consisting of CRM$_{197}$-Aβ1-5, CRM$_{197}$-Aβ1-7, CRM$_{197}$-Aβ1-9, and CRM$_{197}$-Aβ1-12. In another aspect of the invention, the conjugate is a conjugate selected from the group consisting of Aβ1-5-C—CRM$_{197}$, Aβ1-7-C—CRM$_{197}$, Aβ1-9-C—CRM$_{197}$, and Aβ1-12-C—CRM$_{197}$, Aβ16-23-C—CRM$_{197}$, Aβ17-24-C—CRM$_{197}$, Aβ18-25-C—CRM$_{197}$, CRM$_{197}$-C-Aβ16-23, CRM$_{197}$-C-Aβ17-24, CRM$_{197}$-C-Aβ18-25, Aβ16-22-C—CRM$_{197}$, Aβ17-23-C—CRM$_{197}$, Aβ18-24-C—CRM$_{197}$, CRM$_{197}$-C-Aβ16-22, CRM$_{197}$-C-Aβ17-23, and CRM$_{197}$-C-Aβ18-24. Aβ1-9-C—CRM$_{197}$, and Aβ1-12-C—CRM$_{197}$. In yet another aspect of the invention, the conjugate is a conjugate selected from the group consisting of selected from the group consisting of Aβ1-5-L-C—CRM$_{197}$, Aβ1-7-L-C—CRM$_{197}$, Aβ1-9-L-C—CRM$_{197}$, and Aβ1-12-L-C—CRM$_{197}$.

Capping

A disadvantage to the use of coupling reagents, which introduce reactive sites into the side chains of reactive amino acid molecules on carrier and/or hapten molecules, is that the reactive sites if not neutralized are free to react with any unwanted molecule either in vitro or in vivo. In the process of the present invention, capping of the unreacted functional groups is accomplished by reaction of the conjugates with pendant reactive groups with reagents which inactivate/cap the reactive groups. Exemplary inactivating/capping reagents for use with the conjugation process of the present invention include cysteamine, N-acetylcysteamine, and ethanolamine. Alternatively, capping is accomplished by reaction with ammonia or ammonium bicarbonate, either of which converts the haloacetyl groups to aminoacetyl groups. Capping is also accomplished at alkaline pH (9.0-9.8) using sodium hydroxide or sodium carbonate, which converts the haloacetyl groups to hydroxyacetyl groups. One potential advantage of converting the haloacetyl groups to aminoacetyl or hydroxyacetyl groups, as opposed to the reaction with cysteamine derivatives, ethanolamine etc., is the introduction of relatively smaller size chemical functionalities, by reaction with ammonia or hydroxide/carbonate. The resulting capped functional groups, e.g. aminoacetyl or hydroxyacetyl, provide relatively less perturbance in the carrier protein portion of the conjugate. The capped peptide immunogen-carrier protein is purified as necessary using known methods, such as chromatography (gel filtration, ion exchange, hydrophobic interaction or affinity), dialysis, ultrafiltration-diafiltration, selective precipitation using ammonium sulfate or alcohol, and the like.

Immunogenic Conjugates and Compositions

The capped peptide immunogen-carrier protein conjugates are administered in an immunogenic composition to mammals, particularly humans, for prophylactic and/or therapeutic purposes. The conjugates of the present invention are used to elicit and/or enhance immune responses against immunogens. For instance, CTL-carrier conjugates are used to treat and/or prevent viral infection, amyloidogenic diseases, cancer etc. Alternatively, polypeptide immunogen-carrier conjugates, which induce antibody responses, are also used.

In therapeutic applications, a conjugate of the present invention is administered to an individual already suffering from an amyloidogenic disease such as Alzheimer's disease. Those in the incubation phase or the acute phase of the disease may be treated with the conjugate of the present invention separately or in conjunction with other treatments, as appropriate.

In therapeutic applications, an immunogenic composition of the present invention is administered to a patient in an amount sufficient to elicit an effective CTL response or humoral response to the amyloid plaque, and to cure, or at least partially arrest disease progression, symptoms and/or complications. An amount adequate to accomplish this is defined as "therapeutically effective dose." Amounts effective for this use will depend in part on the peptide composition, the manner of administration, the stage and severity of the disease being treated, the weight and general state of health of the patient, and the judgment of the prescribing physician.

Therapeutically effective amounts of the immunogenic compositions of the present invention generally range for the initial immunization for therapeutic or prophylactic administration, from about 0.1 µg to about 10,000 µg of peptide for a 70 kg patient, usually from about 0.1 to about 8000 µg, preferably between about 0.1 to about 5000 µg, and most preferably between 0.1 to about 1,000 µg. These doses are followed by boosting dosages of from about 0.1 µg to about 1000 µg of peptide pursuant to a boosting regimen over weeks to months depending upon the patient's response and condition by measuring specific immune responses.

Further, the present invention is used prophylactically to prevent and/or ameliorate amyloidogenic disease. Effective amounts are as described above. Additionally, one of ordinary skill in the art would also know how to adjust or modify prophylactic treatments, as appropriate, for example by boosting and adjusting dosages and dosing regimes.

Therapeutic administration may begin at the first sign of the disease. This is followed by boosting doses until the disease progression is halted or reversed or the symptoms are substantially abated and for a period thereafter.

Immunogenic compositions of the present invention for therapeutic or prophylactic treatment can be administered by parenteral, topical, intravenous, oral, subcutaneous, intra-arterial, intra-cranial, intra-peritoneal, intra-nasal or intra-muscular means for prophylactic and/or therapeutic treatment. One typical route of administration of an immunogenic agent is subcutaneous, although other routes can be equally effective. Another common route is intra-muscular injection. This type of injection is most typically performed in the arm or leg muscles. In some methods, agents are injected directly into a particular tissue where deposits have accumulated, for example intra-cranial injection. Intra-muscular injection or intravenous infusion is preferred for administration of antibody. In some methods, particular therapeutic antibodies are injected directly into the cranium. Because of the ease of administration, the immunogenic compositions of the invention are particularly suitable for oral administration. The invention further provides immunogenic compositions for parenteral administration, which comprise a solution of the peptides or conjugates, dissolved or suspended in an acceptable carrier, preferably an aqueous carrier.

A variety of diluents, excipients and buffers may be used, e.g., water, buffered water, phosphate buffered saline, 0.3% glycine, hyaluronic acid and the like. These compositions may be sterilized by conventional, well-known sterilization techniques, or may be sterile filtered. The resulting aqueous solutions may be packaged for use as is, or lyophilized, the lyophilized preparation being combined with a sterile solution prior to administration. The compositions may contain pharmaceutically acceptable auxiliary substances as required to approximate physiological conditions, such as buffering agents, tonicity adjusting agents, wetting agents and the like, for example, sodium acetate, sodium lactate, sodium chloride, potassium chloride, calcium chloride, sorbitan monolaurate, triethanolamine oleate, etc.

For solid compositions, conventional nontoxic solid carriers may be used. These may include, for example, pharmaceutical grades of mannitol, lactose, starch, magnesium stearate, sodium saccharin, talcum, cellulose, glucose, sucrose, magnesium carbonate, and the like. For oral administration, a pharmaceutically acceptable nontoxic composition is formed by incorporating any of the normally employed excipients, such as those carriers previously listed, and generally 10-95% of active ingredient, that is, one or more conjugates of the invention, and more preferably at a concentration of 25-75%.

The concentration of immunogenic compositions of the present invention in the pharmaceutical formulations can vary widely, i.e., from less than about 0.1%, usually at or at least about 2% to as much as 20% to 50% or more by weight, and will be selected primarily by fluid volumes, viscosities, etc., in accordance with the particular mode of administration selected.

The conjugates of the present invention may also be administered via liposomes, which serve to target the conjugates to a particular tissue, such as lymphoid tissue, or targeted selectively to infected cells, as well as increase the half-life of the peptide composition. Liposomes include emulsions, foams, micelles, insoluble monolayers, liquid crystals, phospholipid dispersions, lamellar layers and the like. In these preparations the composition to be delivered is incorporated as part of a liposome, alone or in conjunction with a molecule, which binds to, for example, a receptor prevalent among lymphoid cells. These molecules would include monoclonal antibodies, which bind to the CD45 antigen, or with other therapeutic or immunogenic compositions. Thus, liposomes filled with a desired composition of the present invention can be directed to the site of lymphoid cells, where the liposomes then deliver the selected therapeutic/immunogenic peptide compositions. Liposomes for use in the invention are formed from standard vesicle-forming lipids, which generally include neutral and negatively charged phospholipids and a sterol, such as cholesterol. The selection of lipids is generally guided by consideration of liposome size, acid lability and stability of the liposomes in the blood stream. A variety of methods are available for preparing liposomes, as described in, e.g., Szoka, et al., *Ann. Rev. Biophys. Bioeng.* 9:467 (1980), U.S. Pat. Nos. 4,235,871, 4,501,728, 4,837,028, and 5,019,369, incorporated herein by reference.

For aerosol administration, the compositions of the present invention are preferably supplied in finely divided form along with a surfactant and propellant. Typical percentages of the composition are 0.01-20% by weight, preferably 1-10%. The surfactant must, of course, be nontoxic, and preferably soluble in the propellant. Representative of such agents are the esters or partial esters of fatty acids containing from 6 to 22 carbon atoms, such as caproic, octanoic, lauric, palmitic, stearic, linoleic, linolenic, olesteric and oleic acids with an aliphatic polyhydric alcohol or its cyclic anhydride. Mixed esters, such as mixed or natural glycerides may be employed. The surfactant may constitute 0.1-20% by weight of the composition, preferably 0.25-5%. The balance of the composition is ordinarily propellant. A carrier can also be included, if desired, as with lecithin for intranasal delivery.

Conjugates of the present invention can optionally be administered in combination with other agents that are at least partly effective in treatment and/or amelioration of a an amyloid disease and/or its symptoms. In the case of Alzheimer's and Down's syndrome, in which amyloid deposits occur in the brain, the conjugates of the invention can be administered in conjunction with other agents that increase passage of the agents of the invention across the blood-brain bather.

The immunogenic composition typically contains an adjuvant. An adjuvant is a substance that enhances the immune response when administered together with an immunogen or antigen. A number of cytokines or lymphokines have been shown to have immune modulating activity, and thus may be used as adjuvants, including, but not limited to, the interleukins 1-$\alpha$, 1-$\beta$, 2, 4, 5, 6, 7, 8, 10, 12 (see, e.g., U.S. Pat. No. 5,723,127), 13, 14, 15, 16, 17 and 18 (and its mutant forms), the interferons-$\alpha$, $\beta$ and $\gamma$, granulocyte-macrophage colony stimulating factor (see, e.g., U.S. Pat. No. 5,078,996) macrophage colony stimulating factor, granulocyte colony stimulating factor, GSF, and the tumor necrosis factor $\alpha$ and $\beta$. Still other adjuvants useful in this invention include a chemokine, including without limitation, MCP-1, MIP-1$\alpha$, MIP-1$\beta$, and RANTES. Adhesion molecules, such as a selectin, e.g., L-selectin, P-selectin and E-selectin may also be useful as adjuvants. Still other useful adjuvants include, without limitation, a mucin-like molecule, e.g., CD34, GlyCAM-1 and MadCAM-1, a member of the integrin family such as LFA-1, VLA-1, Mac-1 and p150.95, a member of the immunoglobulin super family such as PECAM, ICAMs, e.g., ICAM-1, ICAM-2 and ICAM-3, CD2 and LFA-3, co-stimulatory molecules such as CD40 and CD40L, growth factors including vascular growth factor, nerve growth factor, fibroblast growth factor, epidermal growth factor, B7.2, PDGF, BL-1, and vascular endothelial growth factor, receptor molecules including Fas, TNF receptor, Flt, Apo-1, p55, WSL-1, DR3, TRAMP, Apo-3, AIR, LARD, NGRF, DR4, DR5, KILLER, TRAIL-R2, TRICK2, and DR6. Still another adjuvant molecule includes Caspase (ICE). See, also International Patent Publication Nos. WO98/17799 and WO99/43839, which are incorporated herein by reference in their entirety for all purposes.

Suitable adjuvants used to enhance an immune response include, without limitation, MPL™ (3-O-deacylated monophosphoryl lipid A; Corixa, Hamilton, Mont.), which is described in U.S. Pat. No. 4,912,094, which is hereby incorporated by reference for all purposes. Also suitable for use as adjuvants are synthetic lipid A analogs or aminoalkyl glucosamine phosphate compounds (AGP), or derivatives or analogs thereof, which are available from Corixa (Hamilton, Mont.), and which are described in U.S. Pat. No. 6,113,918, which is hereby incorporated by reference. One such AGP is 2-[(R)-3-Tetradecanoyloxytetradecancylamino]ethyl 2-Deoxy-4-O-phosphono-3-O—[(S)-3-tetradecanoyoxytetradecanoyl]-2-[(R)-3-tetradecanoyloxy-tetradecanoylamino]-b-D-glycopyranoside, which is known as 529 (also known as RC529; Corixa). This 529 adjuvant is formulated as an aqueous form (529 AF) or as a stable emulsion (529 SE).

Still other adjuvants include mineral oil and water emulsions, calcium salts such as calcium phosphate, aluminum salts (alum), such as aluminum hydroxide, aluminum phosphate, etc., Amphigen, Avridine, L121/squalene, D-lactide-polylactide/glycoside, pluronic acids, polyols, muramyl dipeptide, killed *Bordetella*, saponins, such as Stimulon™ QS-21 (Antigenics, Framingham, Mass.), described in U.S. Pat. No. 5,057,540, which is hereby incorporated by reference 3, and particles generated therefrom such as ISCOMS (immunostimulating complexes), *Mycobacterium tuberculosis*, bacterial lipopolysaccharides, synthetic polynucleotides such as oligonucleotides containing a CpG motif (U.S. Pat. No. 6,207,646, which is hereby incorporated by reference), a pertussis toxin (PT), or an *E. coli* heat-labile toxin (LT), particularly LT-K63, LT-R72, PT-K9/G129; see, e.g., International Patent Publication Nos. WO 93/13302 and WO 92/19265, which are/incorporated herein by reference for all purposes.

Also useful as adjuvants are cholera toxins and mutants thereof, including those described in published International Patent Application No. WO 00/18434 (wherein the glutamic acid at amino acid position 29 is replaced by another amino acid (other than aspartic acid, preferably a histidine). Similar CT toxins or mutants are described in published International Patent Application number WO 02/098368 (wherein the isoleucine at amino acid position 16 is replaced by another amino acid, either alone or in combination with the replacement of the serine at amino acid position 68 by another amino acid; and/or wherein the valine at amino acid position 72 is replaced by another amino acid). Other CT toxins are described in published International Patent Application number WO 02/098369 (wherein the arginine at amino acid position 25 is replaced by another amino acid; and/or an amino acid is inserted at amino acid position 49; and/or two amino acids are inserted at amino acid position 35 and 36).

It is to be understood that reference throughout this specification to any theory to explain the results described is not to limit the scope of the invention. Independent of the method by which the invention functions, the results and advantages described herein may be achieved by reference to the following examples of the invention.

It will be apparent to one of ordinary skill in the art that many changes and modifications can be made thereto without departing from the spirit or scope of the appended claims. All publications, patents and patent applications mentioned in this specification are incorporated by reference in their entirety for all purposes to the same extent as if each individual publication, patent or patent application was specifically and individually indicated to be incorporated by reference.

Example 1

Conjugation of $CRM_{197}$ to Aβ Peptide

Conjugation of haptens/antigenic peptides was carried out by reacting activated carrier $CRM_{197}$, which has thirty-nine lysine residues, to a hapten/antigenic peptide having a pendant thiol-group using the method described below (FIG. 1). All the Aβ peptides contained a cysteine residue at the carboxy terminus to facilitate the conjugation of these peptides through the cysteinyl sulfhydryl group to the carrier protein. These peptides were produced by solid phase synthesis.

I. Activation

Free amino groups of $CRM_{197}$ were bromoacetylated by reaction with an excess of bromoacetic acid N-hydroxysuccinimide ester (Sigma Chemical Co., St. Louis, Mo.) (Bernatowicz and Matsueda, 1986). To an ice-cold solution of $CRM_{197}$ (~15 mg), 10% (v/v) 1.0 M $NaHCO_3$ (pH 8.4) was added. Bromoacetic acid N-hydroxysuccinimide ester, equal in weight to that of $CRM_{197}$ used, was dissolved in 200 μL dimethylformamide (DMF), added slowly to the $CRM_{197}$, and gently mixed at room temperature in the dark for 1 hour. The resulting bromoacetylated (activated) protein was purified by passage through a desalting (P6-DG) column using PBS/1 mM EDTA (pH 7.0) as the eluent. Following purification, the fractions corresponding to activated $CRM_{197}$ were pooled and the protein concentration was estimated by BCA protein assay. The protein amino groups, both before and after treatment with bromoacetic acid N-hydroxysuccinimide ester, were reacted with 2,4,6-trinitrobenzenesulfonic acid (TNBSA), which served as an indicator of bromoacetylation (Means et al., 1972).

II. Conjugation

Prior to conjugation, the peptides were reacted with 5,5'-dithio-bis(2-nitrobenzoic acid) [Ellman's reagent] to verify the content of free-SH groups (between 62-88% reduced). For the first four Aβ peptides (amino acids 1-7 without linker, amino acids 1-12 with GAGA (SEQ ID NO.:10) linker, amino acids 1-9 with GAGA (SEQ ID NO.: 10) linker, and amino acids 1-7 with GAGA (SEQ ID NO.: 10) linker), approximately 8.0-10.0 mg of peptide was dissolved in sterile distilled water to an approximate concentration of 20 mg/ml. The peptide was slowly added to cold activated $CRM_{197}$ in a 1:1 ratio (w/w) and the pH was adjusted to approximately 7.0-7.2 with the addition of 20-36 μl of 1 N NaOH. The resulting material was gently mixed overnight at 4° C. in the dark followed by dialysis in the dark against two 1 L changes of PBS, pH 7.2. For the next four Aβ peptides (amino acids 1-5 without linker, amino acids 1-9 without linker, amino acids 1-12 without linker, and amino acids 1-5 with linker), reaction with Ellman's reagent was used to verify the free —SH groups. $CRM_{197}$ was bromoacetylated, purified, and reacted with TNBSA as previously described. The pH of each peptide was adjusted to 7.0 with the addition of 0.1 M $NaPO_4$ (pH 8.5) at 2.2× the volume of the dissolved peptide. The peptide was slowly added to cold activated $CRM_{197}$ in a 1:1 ratio and allowed to react overnight at 4° C. in the dark. The resulting material was dialyzed. A final control peptide (1-12 mer in reverse orientation) was conjugated to $CRM_{197}$ as described above with the following modification. Rather than adjusting the pH of the peptide to 7.0, the pH of the activated $CRM_{197}$ was adjusted to approximately 7.5 with the addition of 20% (v/v) 0.5 M $NaPO_4$ (pH 8.0). Each conjugate, after dialysis, was transferred into a sterile 15 mL polypropylene tube, wrapped in aluminum foil, and stored at 4° C. Activation of the reactive amino residues on the carrier was then subsequently verified using mass spectrometry.

| Conjugate | Immunogenic Peptide |
|---|---|
| Aβ1-5-C-$CRM_{197}$ | DAEFR-C (SEQ. ID. NO.: 1) |
| Aβ1-7-C-$CRM_{197}$ | DAEFRHD-C (SEQ. ID NO.: 2) |
| Aβ1-9-C-$CRM_{197}$ | DAEFRHDSG-C (SEQ ID NO: 3) |
| Aβ1-12-C-$CRM_{197}$ | DAEFRHDSGYEV-C (SEQ ID NO: 4) |
| Aβ1-5-L-C-$CRM_{197}$ | DAEFR-GAGA-C (SEQ ID NO.: 5) |
| Aβ1-7-L-C-$CRM_{197}$ | DAEFRHD-GAGA-C (SEQ ID NO.: 6) |
| Aβ1-9-L-C-$CRM_{197}$ | DAEFRHDSG-GAGA-C (SEQ ID NO.: 7) |
| Aβ1-12-L-C-$CRM_{197}$ | DAEFRHDSGYEV-GAGA-C (SEQ ID NO.: 8) |
| Aβ12-1-C-$CRM_{197}$ (-VE CONTROL) | VEYGSDHRFEAD-C (SEQ ID NO.: 9) |
| L = linker (GAGA) | (SEQ ID NO.: 10) |

Example 2

Preparation of Aβ Peptide-$CRM_{197}$ and Purification by Ultrafiltration Bromoacetylation of $CRM_{197}$ $CRM_{197}$ (100 mg) in 0.01 M sodium phosphate buffer, 0.9% NaCl, pH 7.0, was reacted with bromoacetic acid N-hydroxysucinimide ester (dissolved to 20 mg/mL in DMSO) at a 1:1 weight ratio under an argon atmosphere. The reaction was titrated as needed to maintain the pH at 7.0. The mixture was stirred in dark for 1.5 hours at room temperature. The reaction mixture was 1.2 μm filtered into the retentate reservoir of a UF/DF system (Millipore Labscale TFF, Billerica, Mass.). Purification was done using a 10K or 30K UF membrane by diafiltration (30-fold) against 0.01 M sodium phosphate buffer/0.9% NaCl, pH 7.0. The bromoacetylated $CRM_{197}$ was filtered by passing through a 0.2 μm filter. The degree of bromoacetylation was determined by reacting the activated $CRM_{197}$ with cysteine, followed by amino acid analysis and quantitation of the resulting carboxymethylcysteine (CMC).

Conjugation of Aβ Peptide and Bromoacetylated $CRM_{197}$ and Capping with N-Acetylacysteamine Bromoacetylated $CRM_{197}$ (50 mg) was transferred to a reaction vessel. To the stirred solution, maintained at 2-8° C., was added 1 M sodium carbonate/bicarbonate. Titration was performed to achieve a target pH of 9.0, under argon atmosphere. Separately, 50 mg of Aβ peptide was weighed out and dissolved in water for injection (WFI) to 20 mg/mL. To this solution was added 1 M sodium carbonate/bicarbonate until pH 9.0 was attained. The peptide solution was added to the bromoacetylated $CRM_{197}$ solution, and the mixture was stirred at 2-8° C. for 14-18 hours. The remaining bromoacetyl groups were capped with a 20-fold molar excess of N-acetyl-cysteamine for 3-6 hours at 2-8° C.

The reaction mixture was filtered through 1.2 μm filter into the retentate reservoir of a UF/DF system (Millipore XL), and the conjugate was purified at room temperature by 30-fold diafiltration on a 10K or 30K. MWCO membrane (Millipore) by diafiltering against 0.01 M sodium phosphate buffer/0.9% NaCl, pH 7.0. The retentate was collected and 0.2 μm filtered and analyzed for protein content (Lowry or Micro-BCA colorimetric assay), by SDS-PAGE, by amino acid analysis, and for immunogenicity in mice.

Example 3

Conversion by Capping of the Unreacted Bromoacetyl Groups to Aminoacetyl Groups

Bromoacetylated $CRM_{197}$ (50 mg), prepared as described above in Example 2, was transferred to a reaction vessel. To the stirred solution, maintained at 2-8° C., was added 1M sodium carbonate/bicarbonate. Titration was performed to achieve a target pH of 9.0, under argon atmosphere. Separately, 50 mg of Aβ peptide was weighed out and dissolved in WFI to 20 mg/mL. To this solution was added 1 M sodium carbonate/bicarbonate until pH 9.0 was attained. The peptide solution was added to the bromoacetylated $CRM_{197}$ solution, and the mixture was stirred at 2-8° C. for 14-18 hours. The remaining bromoacetyl groups were capped using 8% ammonium bicarbonate solution for 4 hours at 2-8° C.

The reaction mixture was 1.2 μm filtered into the retentate reservoir of a UF/DF system (Millipore XL), and the conjugate was purified at room temperature by 30-fold diafiltration on a 10K or 30K MWCO membrane by diafiltering vs 0.01 M sodium phosphate buffer/0.9% NaCl, pH 7.0. The retentate was collected and 0.2 μm filtered and analyzed for protein content (Lowry or Micro-BCA colorimetric assay), by SDS-PAGE, by amino acid analysis, and for immunogenicity in mice.

Example 4

Figure 2:
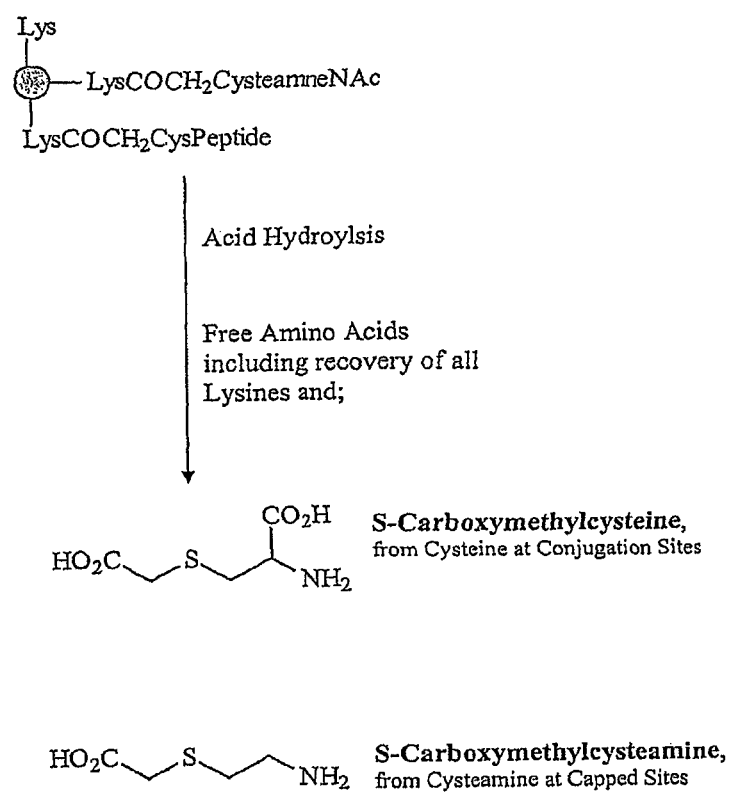
FIG. 2: Flow chart depicting acid hydrolysis chemistry used for quantitative determination of S-carboxymethylcysteine and S-carboxymethylcysteamine as evaluation of the degree of conjugation of peptide immunogen-protein/polypeptide conjugates such as the Aβ/CRM$_{197}$ conjugate.

Quantitative Determination of S-Carboxymethylcysteine and S-Carboxymethylcysteamine as Evaluation of Degree of Conjugation and Capping of Peptide Immunogen-Protein/Polypeptide Conjugates Acid hydrolysis of protein-peptide conjugates generated using bromoacetyl activation chemistry resulted in the formation of acid stable S-carboxymethylcysteine (CMC) from the cysteines at the conjugated sites and the formation of acid stable S-carboxymethyleysteamine (CMCA) from the cysteamine at the capped sites (FIG. 2). All of the conjugated and capped lysines were converted back to lysine and detected as such. All other amino acids were hydrolyzed back to free amino acids except for tryptophan and cysteine, which were destroyed by the hydrolysis conditions. Asparagine and glutamine were converted to aspartic acid and glutamic acid respectively.

Conjugate samples were diluted with deionized water to a total protein concentration of less then 1 mg/mL. Two 10 microgram aliquots of each conjugate were dried and resuspended in 100 μL of 6N HCl [Pierce], 5 μL of melted phenol [Sigma-Aldrich], and 1 μL of 2-mercaptoethanol [Sigma-Aldrich]. The samples were then incubated under vacuum (100 mT) at 110° C. for 22 hours. The resulting hydrolysates were dried, resuspended in 250 μL of Beckman Na—S sodium citrate sample dilution buffer (pH 2.2) [Beckman Instruments, Inc., Fullerton, Calif.], and filtered using Whatman 0.2 μm nylon syringe tip filters and 1 mL syringes.

Each sample was then loaded into a Beckman 6300 amino acid analyzer sample loop and placed in the analyzer. The amino acids of each hydrolyzed sample and control were separated using ion exchange chromatography followed by reaction with Beckman Ninhydrin NinRX solution at 135° C. The derivatized amino acids were then detected in the visible range at 570 nm and 440 nm (see Table 1). A standard set of amino acids [Pierce Amino Acid Standard H] containing 500 picomoles of each amino acid was run along with the samples and controls for each set of analysis. S-carboxymethylcysteine [Sigma-Aldrich] was added to the standard.

TABLE 1

Retention Times for Amino Acids Using Gradient Program 1 on the Beckman 6300 Amino Acid Analyzer

| Retention Time (min.) | Amino Acid | | Wavelength used for Detection |
|---|---|---|---|
| 8.3 | Carboxymethylcysteine | CMC | 570 |
| 9.6 | Aspartic Acid & Asparagine | Asx | 570 |
| 11.3 | Threonine | Thr | 570 |
| 12.2 | Serine | Ser | 570 |
| 15.8 | Glutamic Acid & Glutamine | Glx | 570 & 440 |
| 18.5 | Proline | Pro | 440 |
| 21.8 | Glycine | Gly | 570 |
| 23.3 | Alanine | Ala | 570 |
| 29.0 | Valine | Val | 570 |
| 32.8 | Methionine | Met | 570 |
| 35.5 | Isoleucine | Ile | 570 |
| 36.8 | Leucine | Leu | 570 |
| 40.5 | Tyrosine | Tyr | 570 |
| 42.3 | Phenylalanine | Phe | 570 |
| 45.4 | Carboxymethylcysteamine | CMCA | 570 |
| 48.8 | Histidine | His | 570 |
| 53.6 | Lysine | Lys | 570 |
| 70.8 | Arginine | Arg | 570 |

The areas of each standard peak were used as a quantitative equivalence for proportional evaluation of each sample. Praline was determined from 440 inn and was converted to an equivalence in 570 inn using Glutamic acid, the closest amino acid.

Each of these picomole values was converted to a molar ratio of amino acid residues using a comparison of picomoles of lysine to the theoretical lysine value present in the protein. Lysine was chosen for this evaluation based on its covalent attachment to Cysteine and Cysteamine and the expected similar hydrolysis. The resulting numbers of moles of amino acids were then compared to the amino acid composition of the protein and reported along with the values for CMC and CMCA. The CMC value was used directly for evaluation of the degree of conjugation and the CMCA value was used directly for evaluation of the degree of capping.

Example 5

Characterization and Optimization of Aβ-CRM$_{197}$ Peptide Conjugates

To verify conjugation, all peptide-CRM$_{197}$ conjugates were analyzed by amino acid analysis and matrix-assisted laser desorption ionization-time of flight (MALDI-TOF) mass spectrometry. For each conjugate, the moles of peptide conjugated to each mole CRM$_{197}$ was determined by amino acid analysis (number of S-carboxymethylcysteine residues) and MALDI-TOF mass spectrometry. The values determined by each method were generally in agreement.

I. Size Exclusion Chromatography:

Batch concentrate samples were removed from storage and allowed to warm to room temperature. The Aβ peptide conjugate sample was gently mixed to insure a homogeneous preparation. The Aβ peptide conjugate sample was spun in an Eppendorf micro-centrifuge to remove any particulates. The supernatant was withdrawn for TosoHaas TSK-Gel G3000SW chromatography (TosoHaas, Stuttgart, Germany). A TosoHaas TSK-Gel G3000SW column was connected to a HPLC system and the pressure limit was set to 1.4 MPa. The column was equilibrated with at least 30 mL of PBS (10 mM sodium phosphate, 150 mM NaCl, pH 7.2±0.1) at a flow rate of 0.75 mL/min. The Aβ peptide conjugate sample was loaded onto the TosoHaas TSK-Gel G3000SW column using the following parameters:

Concentration of Aβ peptide conjugate sample: 1.5±1.0 mg/mL
Flow rate: 0.75 mL/min
Sample Volume: 0.1 mL
Run Time: 30 minutes The absorbance was monitored at both 280 nm and 210 nm. For long term storage, the TosoHaas TSK-Gel G3000SW column was equilibrated with at least 50 mL of 20% ethanol at a flow rate of 0.5-1.0 mL/min.

II. PAGE (Polyacrylamide Gel Electrophoresis):

The activated (bromoacetylated) CRM$_{197}$ and the Aβ peptide-CRM$_{197}$ conjugates were examined by SDS-Gels using a NuPAGE Bis-Tris Electrophoresis (Novex, Frankfurt, Germany) with a neutral pH, pre-cast polyacrylamide mini-gel system and NuPAGE MES SDS Running Buffer. An 8 μg aliquot of each activated CRM or conjugate was mixed with reducing sample buffer and heated at 100° C. for 5 minutes. The conjugates and molecular weight (MW) standards (Invitrogen, Carlsbad, Calif.) were loaded on a 10% (w/v, acrylamide) NuPage gel (Novex) based upon a Bis-Tris-HCl buffered system and run on MES SDS Running Buffer-PAGE (Laemmli). Following SDS-PAGE, the gel was stained with Pierce Gel Code Blue (Pierce, Rockford, Ill.). Aβ peptide-CRM$_{197}$ conjugate was represented by a major band around 66 kDa, above the band of native CRM and a dimer band around 120 kDa, along with minor multimer bands (data not shown).

III. MALDI-TOF Mass Spectrometry Analysis of Peptide-CRM$_{197}$ Conjugates:

Mass spectrometry was used for immediate approximation of the degree of conjugation. Suitable aliquots of activated CRM$_{197}$ and conjugate samples were analyzed by MALDI-TOF mass spectrometry using 3,5-dimethoxy-4-hydroxycinnamic acid (sinapinic acid) as the matrix. The molecular weight of activated CRM$_{197}$ determined by MALDI-TOF mass spectrometry (Finnigan MAT Lasermat 2000 Mass Spectrometer, Ringoes, N.Y.) was found to be centered around 60.5 kDa and for conjugates varied from 65 kDa to 74 kDa depending on the degree of conjugation (data not shown). Up to 22 of the lysines (~50%) in CRM$_{197}$ were found to be modified at 1:1 ratio.

Figure 3:
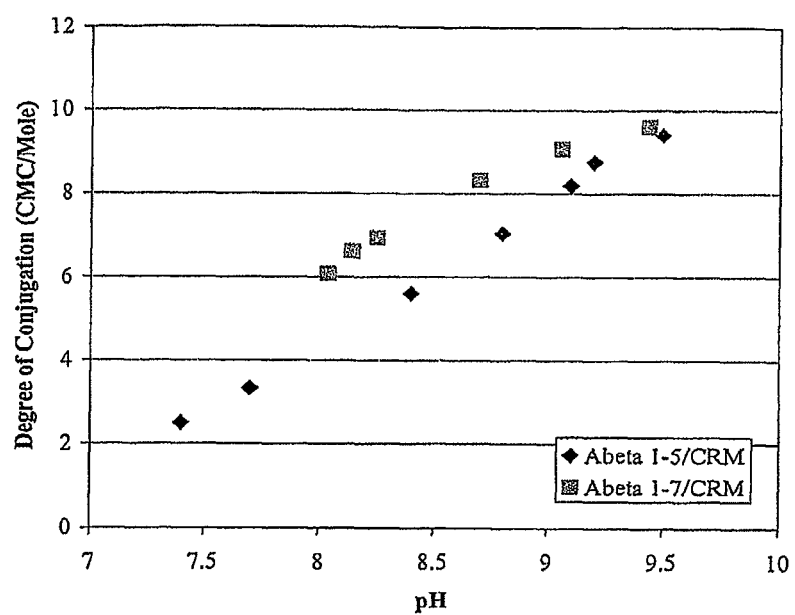
FIG. 3: This figure depicts the pH dependence of the Aβ peptide/CRM conjugation reaction.
Figure 4:
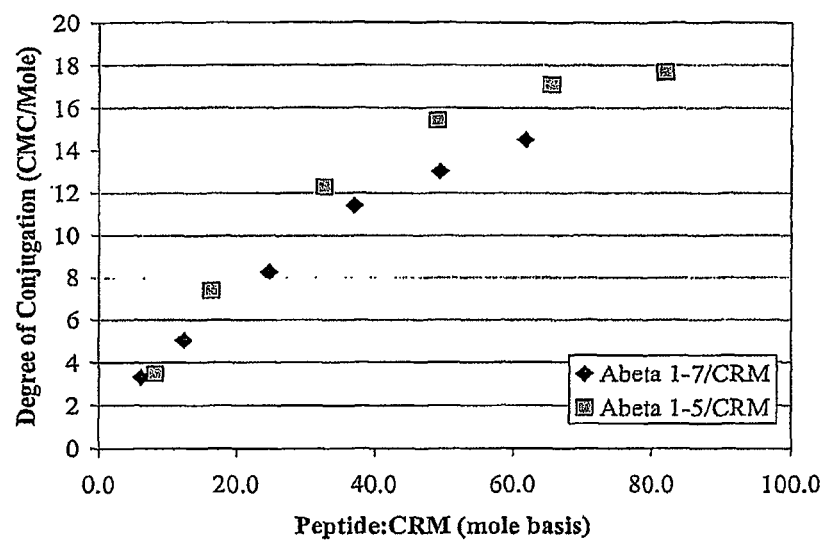
FIG. 4: This figure depicts the dependence of Aβ-peptide/CRM conjugation on peptide:CRM ratio.

IV. Optimization Experiments:

The degree of activation and conjugation are a function of reagent:protein ratio, temperature of the reaction and pH of the reaction buffer. Some examples are given below to illustrate the optimal conjugation conditions carried out to identify the optimal pH conditions in order to have reproducible process control parameters for conjugation reactions. Results (FIG. 3) showed that the conjugation reaction to Aβ 5 mer (DAEFRC) (SEQ ID NO:1) as well as Aβ 7 mer (DAEFRHDC) (SEQ ID NO:2) is pH dependent and yields a higher degree of modification/conjugation when the pH of the reaction condition is increased. Using the TFA salt of 5 mer and 7 mer peptides, the degree of conjugation was evaluated at pH 9.0 with varying amounts of peptide load (FIG. 4). It is evident from these results that peptide conjugates with a defined number of peptide copies per CRM molecule can be generated by varying the peptide/activated CRM ratio during the conjugation process. Similar experiments were done using acetate salt of Aβ 7 mer peptide.

Figure 5:
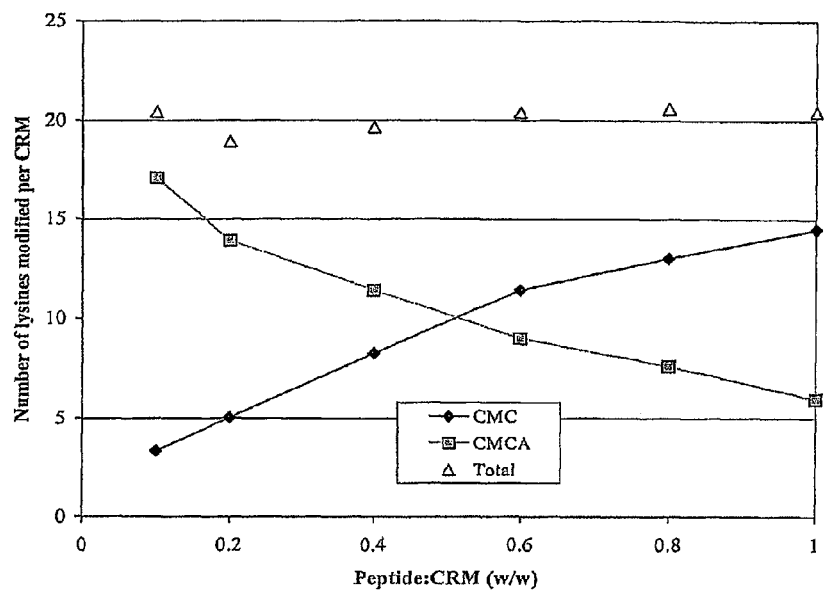
FIG. 5: Verification of capping process for Aβ1-7/CRM conjugation. The pH of the reaction was 9.15. Reaction time with peptide was 16 hrs, capping with N-acetylcysteamine was 8 hrs.
Figure 6:
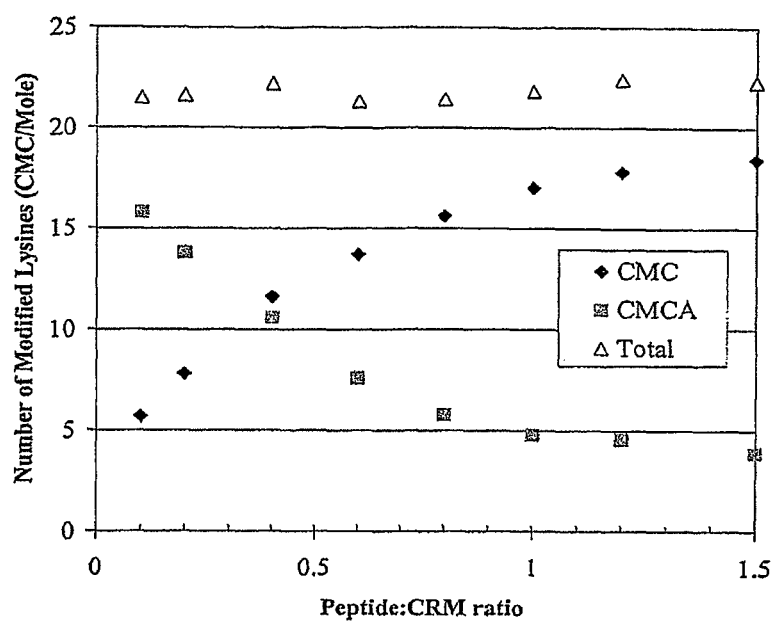
FIG. 6: Conjugation and capping with various peptide:CRM ratios with peptide. The pH of the reaction was 9.0. Reaction time with peptide was 16 hrs, capping with N-acetylcysteamine was 8 hrs.

For the Aβ1-7/CRM conjugation, the capping process was evaluated by comparing the moles of CMCA per CRM to the moles of CMC per CRM. Since the total of the CMC and CMCA was constant for each peptide:CRM ratio tested, the capping process was presumed to be complete (FIG. 5). The total modification in the conjugate stayed between 19 and 21, comparable to the number of lysines bromoacetylated (FIG. 5). These experiments were done with TFA as the counterion for the peptide. The Aβ1-7/CRM conjugation was repeated using the acetate salt of the peptide rather than the TFA salt, and these data are shown in FIGS. 5 and 6. The capping process appeared to go to completion, with the total of the CMC and CMCA for each point staying between 20 and 22. The conditions for the Aβ-CRM conjugation reaction have been optimized at pH 9.0, with the degree of conjugation controlled by the peptide to CRM ratio in the reaction. By varying the ratio from 0.1 to 1.5, the degree of conjugation can be varied (FIG. 6).

The degree of activation and conjugation are a function of reagent:protein ratio, temperature of the reaction and pH of the reaction buffer. The degree of modification (conjugation) for each conjugate was calculated by subtracting the mass value of activated CRM$_{197}$ from the mass value of each conjugate and dividing by the mass of the peptide used to prepare the conjugate. The degree of modification (conjugation) for all of the conjugates is described in the Table 2.

The degree of conjugation was also compared to the values determined by the estimated amount of S-carboxymethylcysteine residues formed per mole of $CRM_{197}$ (also shown in Table 2).

TABLE 2

Degree of Modification: Comparison of MALDI-TOF and AAA Data

| Sample | Da (From Mass Spectrometry) | Degree of conjugation (From Mass Spectrometry) | Degree of conjugation (From CMC-Amino Acid Analysis) |
|---|---|---|---|
| $CRM_{197}$ | 58,408 | — | — |
| BrAc-CRM | 60,752 | 19 | — |
| Aβ1-7/CRM | 74,463 | 14 | 15 |
| Aβ1-7/CRM | 72,375 | 12 | 14 |
| Aβ1-5/CRM | 75,425 | 20 | 21 |
| Aβ1-5/CRM | 71,690 | 15 | 18 |

Example 6

Immunogenicity Studies of Aβ Peptide Conjugates

Peptides spanning N-terminal residues 1-5, 1-7, 1-9, and 1-12 of Aβ (with and without the linker sequence GAGAC) and a peptide corresponding to the N-terminus of Aβ in reverse sequence from amino acid twelve to amino acid one (1-12 mer in reverse sequence), each conjugated to $CRM_{197}$, were used to immunize mice along with an unconjugated Aβ1-12 mer peptide in a formulation with STIMULON™ QS-21. Each group of mice was immunized subcutaneously with a dose of either 30 µg or 5 µg of one of the samples formulated with 20 µg of the adjuvant STIMULON™ QS-21, at the beginning of the study (week 0) and subsequently at weeks 3 and 6. The study protocol is illustrated in Table 3.

As shown in Table 3, peptides spanning N-terminal residues 1-5, 1-7, 1-9, and 1-12 of Aβ (with and without the linker sequence GAGAC) and a peptide corresponding to the N-terminus of Aβ in reverse sequence from amino acid twelve to amino acid one (1-12 mer in reverse) conjugated to $CRM_{197}$ were used to immunize mice along with unconjugated Aβ 1-12 mer peptide in a formulation with QS-21. Each group of mice was vaccinated subcutaneously with a dose of either 30 µg or 5 µg of one of the samples formulated with 20 µg of the adjuvant QS-21, at the beginning of the study (week 0) and subsequently at weeks 3 and 6. Swiss Webster mice were used for the entire study with 5 mice in each group. Injection volume=100 µl; B=Bleed; V=vaccinate; E=exsanguinate.

Anti-Aβ titers were measured by ELISA against Aβ and $CRM_{197}$ as described below. Briefly, Costar 96 well plates (#3591) were coated overnight at room temperature with 2 µg/mL Aβ1-42 in sterile carbonate/bicarbonate buffer, pH 9.6. Plates were emptied and blocked for two hours at room temperature with 200 µl/well of 0.05% BSA in 1×PBS/0.05% Tween 20. Blocked plates were emptied and washed with a plate washer containing TBS, 0.1% Brij-35 (without azide) wash buffer. All primary antisera were serially diluted with 0.05% BSA in 1×PBS containing 0.05% Tween 20/0.02% Azide and 100 µL of each dilution was then transferred to the appropriate plate wells and incubated at room temperature for 2 hours. Plates were then emptied/washed as described above. Alkaline phosphatase conjugated goat anti-mouse IgG secondary antibody from Southern Biotech (city, state) was diluted 1:1000 with 0.05% BSA in PBS containing 0.05% Tween 20/0.02% Azide and 100 µL was added to each well and incubated at room temperature for 1 hour. Plates were then emptied/washed as described above and finally incubated at room temperature for 1 hour with 100 µL/well of a 1 mg/mL solution of p-nitrophenyl phosphate substrate prepared in diethanolamine/$MgCl_2$, pH 9.8. The color development was stopped with the addition of 50 µL/well of 3 N NaOH. Plates were read at 405 nM with a 690 nM reference. Endpoint titers were calculated at an O.D. of 0.1 AU.

TABLE 3

Mouse Immunization Study Protocol

| Group Code | Description | Dose (µg) | Wk 0 | Wk 3 | Wk 6 | Wk 8 | Wk 13 | Wk 16 |
|---|---|---|---|---|---|---|---|---|
| AE488 | CRM/1-7 w/o linker | 30 | B, V | B, V | B, V | B | B | E |
| AE489 | CRM/1-12 with linker | 30 | B, V | B, V | B, V | B | B | E |
| AE490 | CRM/1-9 with linker | 30 | B, V | B, V | B, V | B | B | E |
| AE491 | CRM/1-7 with linker | 30 | B, V | B, V | B, V | B | B | E |
| AE492 | CRM/1-5 w/o linker | 30 | B, V | B, V | B, V | B | B | E |
| AE493 | CRM/1-9 w/o linker | 30 | B, V | B, V | B, V | B | B | E |
| AE494 | CRM/1-12 w/o linker | 30 | B, V | B, V | B, V | B | B | E |
| AE495 | CRM/1-5 with linker | 30 | B, V | B, V | B, V | B | B | E |
| AE496 | CRM/1-7 w/o linker | 5 | B, V | B, V | B, V | B | B | E |
| AE497 | CRM/1-12 with linker | 5 | B, V | B, V | B, V | B | B | E |
| AE498 | CRM/1-9 with linker | 5 | B, V | B, V | B, V | B | B | E |
| AE499 | CRM/1-7 with linker | 5 | B, V | B, V | B, V | B | B | E |
| AE500 | CRM/1-5 w/o linker | 5 | B,V | B,V | B,V | B | B | E |
| AE501 | CRM/1-9 w/o linker | 5 | B, V | B, V | B, V | B | B | E |

TABLE 3-continued

Mouse Immunization Study Protocol

| Group Code | Description | Dose (µg) | Wk 0 | Wk 3 | Wk 6 | Wk 8 | Wk 13 | Wk 16 |
|---|---|---|---|---|---|---|---|---|
| AE502 | CRM/1-12 w/o linker | 5 | B, V | B, V | B, V | B | B | E |
| AE503 | CRM/1-5 with linker | 5 | B, V | B, V | B, V | B | B | E |
| AE504 | CRM$_{197}$ C1-6151 | 30 | B, V | B, V | B, V | B | B | E |
| AE505 | CRM$_{197}$ C1-6151 | 5 | B, V | B, V | B, V | B | B | E |
| AE506 | CRM/12-1mer | 30 | B, V | B, V | B, V | B | B | E |
| AE507 | CRM/12-1mer | 5 | B, V | B, V | B, V | B | B | E |
| AE508 | 1-12mer peptide | 30 | B, V | B, V | B, V | B | B | E |
| AE509 | 1-12mer peptide | 5 | B, V | B, V | B, V | B | B | E |
| AE510 | Ab | 30 | B, V | B, V | B, V | B | B | E |
| AE511 | Ab | 5 | B, V | B, V | B, V | B | B | E |

CRM$_{197}$ ELISA

Greiner 96 well plates (#650011) were coated at 37° C. for 90 minutes with 5.0 µg/mL (100 µl/well) of CRM$_{197}$ in sterile carbonate/bicarbonate buffer, pH 9.6. Plates were emptied and washed with a plate washer containing 1×TBS, 0.1% Brij-35 wash buffer. All primary antisera were serially diluted with 1×PBS containing 0.3% Tween 20/EDTA and 100 µL of each dilution was then transferred to the appropriate plate wells and incubated at 37° C. for 1 hour. The plates were then emptied/washed as described above. Alkaline phosphatase conjugated goat anti-mouse IgG secondary antibody from Southern Biotech was diluted 1:1000 with 1×PBS containing 0.05% Tween 20/0.02% Azide and 100 µl was added to each well and incubated at 37° C. for 1 hour. Plates were then emptied/washed as described above and finally incubated at room temperature for 1 hour with 100 µL/well of a 1 mg/mL solution of p-nitrophenyl phosphate substrate prepared in diethanolamine/MgCl$_2$, pH 9.8. The development was stopped with the addition of 50 µL/well of 3 N NaOH. Plates were read at 405 nM with a 690 nM reference. Endpoint titers were calculated at an O.D. of 0.1 AU.

Tables 4-6 illustrate end point ELISA titers against Aβ. Following primary immunization, all eight conjugates (excluding the negative control) induced measurable anti-Aβ IgG immune responses. However, the 30 µg dose, but not the 5 µg dose, of Aβ gave a positive response at week 3 following primary immunization. Among all the conjugates, it appears that Aβ 1-7 peptide conjugated without linker elicited as good as or better response than other conjugates studied. At 5 µg dose, Aβ 1-5C did better at weeks 8-16. Aβ 1-7C was best at 30 µg dose. Analysis of antibody titers after second and third immunization with either 5 or 30 µg dose indicate that the maximal immune response to Aβ for most of the conjugates was seen after the second immunization. At least in mice, the third immunization did not appear to enhance the immune response. Aβ peptide however, needed three immunizations with the 30 µg dose to reach maximal immune response against the peptide (Table 5). In terms of antibody decay over an extended period of time, the antibody level from the groups immunized with conjugates was reduced by 2 to 3 fold as compared to the highest level within that group. Individual samples from weeks 6 and 8 were analyzed to calculate GMTs against Aβ for each of the group (Table 6) to see if any conjugate group was substantially better than the others. Statistical analysis of week 6 titers from Aβ1-5C, Aβ 1-7C and Aβ 1-9C conjugates indicated that the Aβ 1-7 conjugate induced a significantly higher titer. It is also evident from this experiment that the linker sequence GAGAC did not contribute to enhancing the immune response to the peptide.

TABLE 4

| Group | Week 3 | Week 6 | Week 8 | Week 13 | Week 16 |
|---|---|---|---|---|---|
| 1-5C | <100 | 14,960 | 687,691 | 882,012 | 625,208 | 771,828 |
| 1-7C | <100 | 51,253 | 1,280,181 | 860,463 | 520,060 | 571,043 |
| 1-9C | <100 | 18,615 | 1,008,872 | 622,325 | 348,967 | 380,755 |
| 1-12C | <100 | 615 | 132,009 | 390,624 | 166,162 | 184,170 |
| 1-5LC | <100 | 4,999 | 458,075 | 454,631 | 237,573 | 220,091 |
| 1-7LC | <100 | 17,693 | 849,170 | 842,402 | 446,089 | 400,536 |
| 1-9LC | <100 | 18,544 | 1,465,115 | 1,180,347 | 571,127 | 579,477 |
| 1-12LC | <100 | 12,664 | 908,360 | 598,867 | 368,101 | 316,075 |
| CRM$_{197}$ | <100 | <100 | <100 | <100 | <100 | <100 |
| 1-42 | <100 | <100 | <100 | <100 | <100 | <100 |
| 1-12 | <100 | <100 | <100 | <100 | <100 | <100 |
| 12-1C | <100 | <100 | <100 | <100 | <100 | <100 |

Weeks 0, 3, 6, 8, 13, and 16 ELISA endpoint titers against Aβ using antiserum from 5 µg dose of peptide conjugates spanning varying lengths of the N-terminus of Amyloid Aβ peptide,
Ref: Elan hyperimmune polyclonal #592 = 3,073,307.

Endpoint at O.D. 0.1 AU. Swiss Webster mice were immunized SC-N with 5 µg of above antigens formulated with 20 µg STIMULON ™ QS-21 at weeks 0, 3, and 6.

TABLE 5

| Group | Week 0 | Week 3 | Week 6 | Week 8 | Week 13 | Week 16 |
|---|---|---|---|---|---|---|
| 1-5C | <100 | 18,150 | 590,355 | 332,832 | 204,645 | 176,159 |
| 1-7C | <100 | 100,672 | 1,840,741 | 647,470 | 592,638 | 779,072 |
| 1-9C | <100 | 18,520 | 1,184,696 | 713,494 | 363,459 | 327,065 |
| 1-12C | <100 | 7,837 | 1,325,725 | 1,126,389 | 681,268 | 577,604 |
| 1-5LC | <100 | 16,347 | 469,191 | 184,077 | 177,358 | 164,680 |
| 1-7LC | <100 | 47,866 | 971,229 | 462,200 | 463,466 | 529,726 |
| 1-9LC | <100 | 59,002 | 921,544 | 787,273 | 405,023 | 500,468 |
| 1-12LC | <100 | 27,348 | 697,150 | 483,320 | 284,800 | 397,816 |
| CRM$_{197}$ | <100 | <100 | <100 | <100 | <100 | <100 |
| 1-42 | <100 | 160 | 3,327 | 109,718 | 48,646 | 27,901 |
| 1-12 | <100 | <100 | <100 | <100 | <100 | <100 |
| 12-1C | <100 | <100 | <100 | <100 | <100 | <100 |

Weeks 0, 3, 6, 8, 13, and 16 ELISA endpoint titers against Aβ using antiserum from 30 µg dose of peptide conjugates spanning varying lengths of the N-terminus of Amyloid Aβ peptide.
Ref: Elan hyperimmune polyclonal #592 = 3,073,307.

Endpoint at O.D. 0.1 AU. Swiss Webster mice were immunized SC-N with 30 µg of above antigens formulated with 20 µg STIMULON ™ QS-21 at weeks 0, 3, and 6.

TABLE 6

Table 6. Weeks 6 and 8 ELISA endpoint GMTs against Aβ using antisera from 30 μg dose of peptide conjugates spanning varying lengths of the N-terminus of Amyloid-Aβ. Ref: Elan Hyperimmune Polyclonal #592 = 3,073,307. Endpoint at O.D. 0.1 AU. Swiss Webster mice were immunized SC-N with 30 μg of above antigens formulated with 20 μg STIMULON™ QS-21 at weeks 0, 3, and 6

| Group | Week 6 | Week 8 |
|---|---|---|
| 1-5C | 237,668 [a] | 161,671 [b] |
| 1-7C | 1,866,702 [a] | 881,146 [b] |
| 1-9C | 963,323 [a] | 595,414 [b] |
| 1-12C | 940,260 | 955,470 |
| 1-5LC | 395,553 | 141,084 |
| 1-7LC | 516,921 | 394,521 |
| 1-9LC | 826,773 | 562,458 |
| 1-12LC | 544,768 | 376,952 |
| 1-42 | 365 | 4,565 |

[a] Statistical analysis of week 6 titers from 1-5C, 1-7C, and 1-9C using Tukey-Kramer show a statistical difference between 1-5C vs 1-7C only, whereas, analysis using Student's T-test shows a statistical difference between 1-5C vs 1-7C and 1-5C vs 1-9C.
[b] Statistical analysis of week 8 titers from 1-5C, 1-7C, and 1-9C does not show a statistical difference among the three groups. However, there appears to be a trend that may indicate a difference between 1-5C vs 1-7C.

PDAPP Mouse Brain Tissue Staining

The PDAPP brain tissue staining assay provides an indication of the functionality of the Aβ peptide conjugates and/or Aβ 1-42 antiserum. Serum samples from individual mouse groups were separately analyzed for their ability to recognize PDAPP mouse brain tissue plaques containing amyloid peptide. The results are shown in Table 7A and 7B. With the exception of the Aβ 5 mer conjugate antisera, there was a dose-related response in recognizing the plaques. Independent of the linker, 30 μg conjugate-induced antisera had better reactivity patterns as compared to that of 5 μg conjugate antisera. However, with the Aβ 5 mer conjugate antisera, there seems be similar or better reactivity for the 5 μg group. Comparing all these results, it is concluded that conjugates made from Aβ 1-5 mer through Aβ 1-9 mer are sufficient in eliciting plaques recognizing immune response in mice and the presence of linker is not essential. The following conclusions can be drawn from this study: (a) All of the peptide conjugates induced high titered antiserum against the carrier protein CRM$_{197}$ to equal or slightly higher levels as compared to the unconjugated CRM$_{197}$ control (not shown). (b) The conjugates with the GAGAC linker did not enhance immunogenicity or functionality compared to conjugates without the linker. (c) The immunogenicity data and PDAPP brain tissue staining (an initial indication of functional antibody) show that the Aβ 1-5 mer and Aβ 1-7 mer conjugates appeared to be the preferred immunogens for further development.

TABLE 7A

PDAPP mouse brain tissue staining.
5 μg Dose

| | Without Linker | | | With Linker | |
|---|---|---|---|---|---|
| Vaccine | Animal # | PDAPP Staining | Vaccine | Animal # | PDAPP Staining |
| CRM/Aβ 1-5 | 1 | +(no diffuse) | CRM/Aβ 1-5 | 1 | – |
| | 2 | ++/+++ | | 2 | – |
| | 3 | ++/+++ | | 3 | ± |
| | 4 | ++ | | 4 | ± |
| | 5 | ++ | | 5 | ± |
| CRM/Aβ 1-7 | 1 | ++ | CRM/Aβ 1-7 | 1 | + |
| | 2 | ++ | | 2 | ++ |
| | 3 | ++ | | 3 | ++ |
| | 4 | ++ | | 4 | + |
| | 5 | ++ | | 5 | ++ |
| CRM/Aβ 1-9 | 1 | + | CRM/Aβ 1-9 | 1 | ++ |
| | 2 | +/++ | | 2 | ++ |
| | 3 | ± | | 3 | + |
| | 4 | ± | | 4 | + |
| | 5 | ± | | 5 | + |
| CRM/Aβ 1-12 | 1 | – | CRM/Aβ 1-12 | 1 | + |
| | 2 | ? | | 2 | + |
| | 3 | ± | | 3 | ++ |
| | 4 | – | | 4 | – |
| | 5 | ± | | 5 | ± |
| CRM/Aβ 12-1mer | 1 | – | Aβ42 | 1 | – |
| | 2 | – | | 2 | – |
| | 3 | ± | | 3 | – |
| | 4 | – | | 4 | – |
| | 5 | ± | | 5 | – |

All antiserum diluted 1:1000 for staining procedure.

TABLE 7B

PDAPP mouse brain tissue staining.
30 μg Dose

| | Without Linker | | | With Linker | |
|---|---|---|---|---|---|
| Vaccine | Animal # | PDAPP Staining | Vaccine | Animal # | PDAPP Staining |
| CRM/Aβ 1-5 | 1 | – | CRM/Aβ 1-5 | 1 | + |
| | 2 | +/++ | | 2 | – |
| | 3 | – | | 3 | – |
| | 4 | ± | | 4 | ± |
| | 5 | ++ | | 5 | – |
| CRM/Aβ 1-7 | 1 | +/++ | CRM/Aβ 1-7 | 1 | + |
| | 2 | ++ | | 2 | ±/+ |
| | 3 | ++ | | 3 | +/++ |
| | 4 | ++ | | 4 | ±/+ |
| | 5 | ++/+++ | | 5 | +/++ |
| CRM/Aβ 1-9 | 1 | ++/+++ | CRM/Aβ 1-9 | 1 | +/++ |
| | 2 | ++ | | 2 | ++ |
| | 3 | ++ | | 3 | ++ |
| | 4 | + | | 4 | ± |
| | 5 | + | | 5 | +/++ |
| CRM/Aβ 1-12 | 1 | – | CRM/Aβ 1-12 | 1 | +/++ |
| | 2 | +/++ | | 2 | + |
| | 3 | +/++ | | 3 | – |
| | 4 | ± | | 4 | +/++ |
| | 5 | ± | | 5 | + |
| CRM/Aβ 12-1mer | 1 | – | Aβ 42 | 1 | ± |
| | 2 | – | | 2 | – |
| | 3 | – | | 3 | – |
| | 4 | – | | 4 | – |
| | 5 | – | | 5 | – |

All antiserum diluted 1:1000 for staining procedure.

Example 7

Immunogenicity Studies in Monkeys

Figure 7:
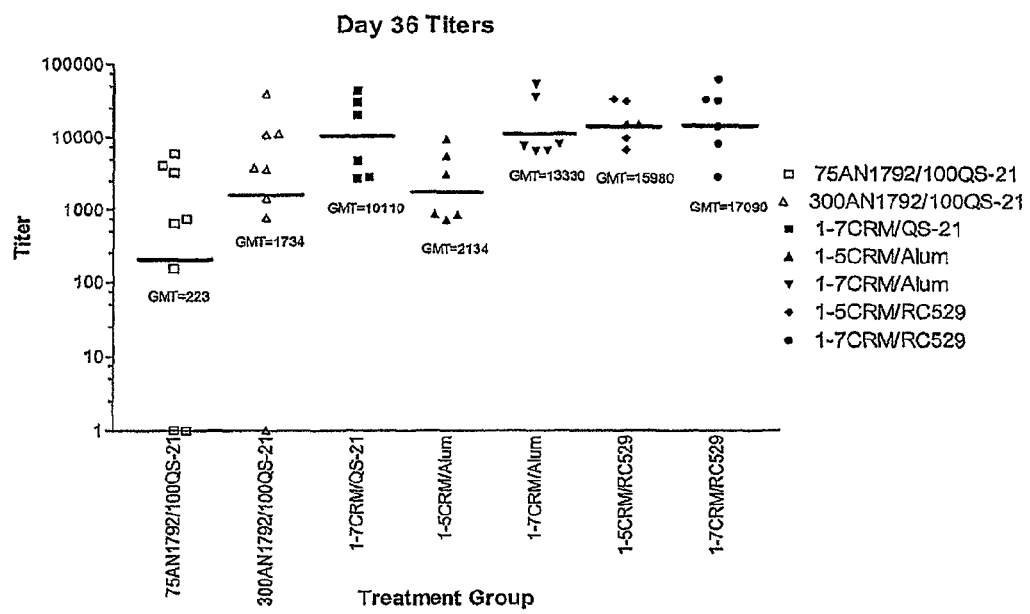
FIG. 7: Day 36 titers of primate sera following immunization of primates with Aβ peptide conjugates with various adjuvants.
Figure 8:
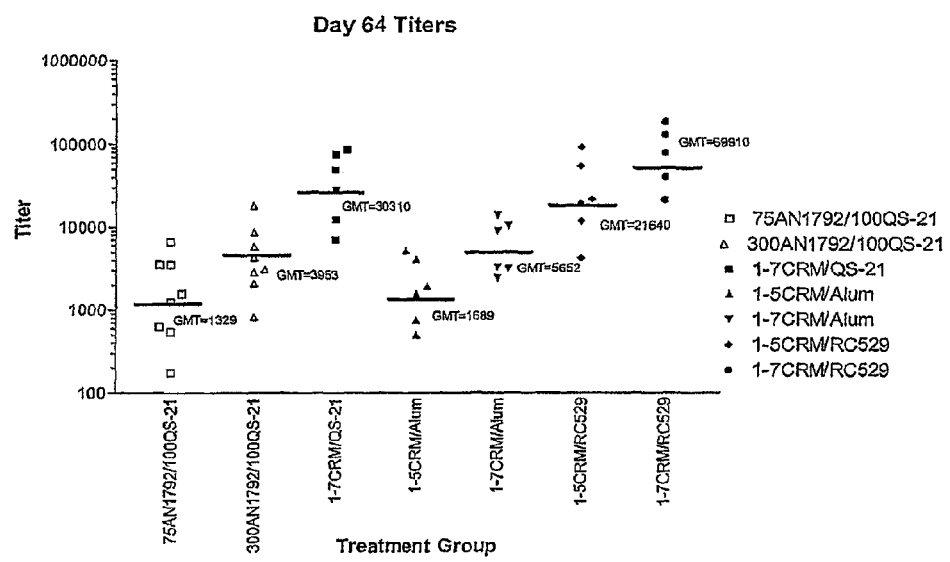
FIG. 8: Day 64 titers of primate sera following immunization of primates with Aβ-peptide conjugates with various adjuvants.
Figure 9:
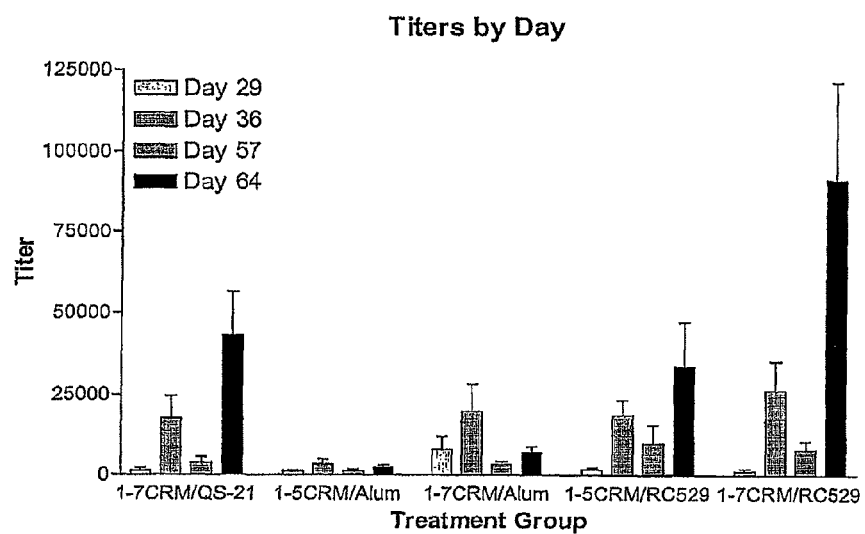
FIG. 9: Primate titers by day and treatment group. Primates were immunized with Aβ 1-7 or Aβ 1-5 CRM$_{197}$ conjugates with alum or RC529 as adjuvants and titers of anti-Aβ antibodies were measured at day 29, 36, 57 and 54.

Groups of 6 monkeys received 30 ug of 7 mer conjugate (total conjugate) adjuvanted with either STIMULON™ QS-21, alum or RC529 SE formulation at days 0, 29 and 58. Additional groups included were 30 ug 5 mer conjugate with either alum (Al(OH)$_3$) or RC529 SE, 75 and 300 μg of Aβ with STIMULON™ QS-21 as positive controls. Positive controls were immunized every two weeks. At day 36 and 64 the anti-Aβ antibody titers were determined (FIGS. 7-9). On day 36, 7 mer/CRM conjugates with STIMULON™ QS-21, Alum and RC529 SE elicited GMT titers of 10110, 13330 and 17090 respectively (FIG. 7). In contrast, Aβ 1-42 plus STIMULON™ QS-21 elicited GMTs of 223 and 1734 at 75 and 300 µg dose levels, respectively. The Aβ 5 mer conjugate elicited a titer of 2134 with alum and 15980 with RC529 SE. On day 64, i.e. after 3 doses of conjugates with either STIMULON™ QS21 or RC-529 SE induced substantially higher titers than post second dose (GMTs 69910 for 7 mer/RC-529 SE; 21640 for Aβ 5 mer/RC-529 SE and 30310 for Aβ 7 mer/STIMULON™ QS-21) (FIG. 8). Conjugates with alum elicited reduced titers at post third immunization compared to post second immunization. It appears that the Aβ 7 mer conjugate elicited a better response as compared to the Aβ 5 mer conjugate. In monkeys, adjuvanting Aβ 7 mer conjugate with RC-529 SE or STIMULON™ QS-21 elicited the highest response (FIG. 9). The response to the Aβ 7 mer conjugate with alum was moderate and similar to that of 300 µg Aβ 1-42 with STIMULON™ QS-21.

Several conclusions can be drawn from the current example. First, both conjugates are very immunogenic in primate species. Second, the presence of adjuvants in the immunization formulation significantly influences the immune response. Third, except for the aluminum adjuvant, RC-529 SE and STIMULON™ QS-21 enhance the immune response after each dose of immunization at least up to three doses (FIG. 9). Overall, Aβ 7 mer conjugate induced higher antibody response in the presence of 529, followed by STIMULON™ QS-21 (see FIG. 9).

Example 8

Preparation of Multiple Antigenic Peptide (Map) Conjugates and their Immunogenicity Study Several methods are available for generating multiple antigenic sites on the carriers. In the previous examples, each antigenic site is separately conjugated to the carrier by defined conjugation and capping chemistries. In this example, multiple antigenic sites are constructed by solid phase synthesis of tandem repeats of Aβ1-7 mer. Alternatively these tandem repeats can be coupled with T-cell epitopes with or without linking through a lysine core as described elsewhere. These multiple antigenic peptides were synthesized with an additional cysteinyl residue for conjugation to the carrier protein. Peptides containing one, repeat unit $(1-7)$, three repeat units $(1-7)_3$ and five repeat units $(1-7)_5$ with an additional cysteinyl residue at the carboxyl end were synthesized. These peptides were covalently attached to bromoacetylated CRM overnight through their C-terminal cysteine residues. The reaction was carried out at pH 9.0-9.2 with peptide:CRM ratios added as outlined in Table 8. Bromoacetyl groups, which did not react with peptide, were capped with N-acetylcysteamine. These lots represent conjugates containing one single copy, three tandem copies, and five tandem copies of the Aβ1-7 peptide conjugated to CRM, respectively. Table 8 briefly outlines the properties of the samples.

TABLE 8

Multiple Antigenic Peptide (MAP) Conjugate Samples

| Conjugate | Peptide: CRM (w/w) | pH of reaction |
|---|---|---|
| Ab(1-7)$_1$/CRM | 0.37 | 8.99 |
| Ab(1-7)$_3$/CRM | 1.02 | 8.95 |
| Ab(1-7)$_5$/CRM | 1.67 | 9.17 |

Peptide load (the average number of Aβ 1-7 peptides per carrier) and capping numbers (Table 9) are the numbers of unique amino acids (CMC or CMCA) per carrier as determined by amino acid analysis. The CMC and CMCA values were referenced to lysine.

TABLE 9

Degree of Conjugation and Capping of Each Conjugate

| CONJUGATE | Peptide Load (CMC) | Capping (CMCA) |
|---|---|---|
| Aβ(1-7)$_1$/CRM | 12.5 | 11.7 |
| Aβ(1-7)$_3$/CRM | 10.4 | 15.2 |
| Aβ(1-7)$_5$/CRM | 9.8 | 15.9 |

Swiss-Webster mice (10 per group) were immunized subcutaneously with 1 or 0.1 µg Aβ/CRM conjugated peptide. Half of the mice were immunized with the composition formulated with 100 µg of the adjuvant Al(OH)$_3$, and half were immunized without adjuvant. Immunizations were scheduled at weeks 0 and 3. Bleeds were scheduled for weeks 0, 3, and 6. Serum samples were analyzed for antibody response against Aβ1-42 mer peptide. The results are shown in Table 10.

TABLE 10

Anti-Aβ Endpoint Titers for Multiple Antigenic Peptide (MAP) Conjugates

| Group Code | Sample Description | Adjuvant | Wk 0 Pool | Wk 3 GMT | Wk 6 GMT |
|---|---|---|---|---|---|
| AG332 | 1 µg Aβ (1-7)$_1$/CRM | Al(OH)$_3$ | <100 | 18,096 | 100,279 |
| AG333 | 1 µg Aβ (1-7)$_3$/CRM | Al(OH)$_3$ | <100 | 44,911 | 420,235 |
| AG334 | 1 µg Aβ (1-7)$_5$/CRM | Al(OH)$_3$ | <100 | 27,032 | 394,488 |
| AG335 | 0.1 µg Aβ (1-7)$_1$/CRM | Al(OH)$_3$ | <100 | 19,350 | 66,834 |
| AG336 | 0.1 µbg Aβ (1-7)$_3$/CRM | Al(OH)$_3$ | <100 | 13,307 | 208,272 |
| AG337 | 0.1 µg Aβ (1-7)$_5$/CRM | Al(OH)$_3$ | <100 | 1,196 | 22,665 |
| AG338 | 1 µg Aβ (1-7)$_1$/CRM | None | <100 | 5,273 | 370,980 |
| AG339 | 1 µg Aβ (1-7)$_3$/CRM | None | <100 | 9,299 | 541,093 |
| AG340 | 1 µg Aβ (1-7)$_5$/CRM | None | <100 | 3,100 | 185,272 |
| AG341 | 0.1 µg Aβ (1-7)$_1$/CRM | None | <100 | 340 | 25,839 |
| AG342 | 0.1 µg Aβ (1-7)$_3$/CRM | None | <100 | 128 | 5,553 |
| AG343 | 0.1 µg Aβ (1-7)$_5$/CRM | None | <100 | 668 | 2,098 |

All conjugates induced anti-Aβ 1-42 antibody titer after primary immunization and the levels were substantially increased after the booster dose. In the absence of aluminum adjuvant, the differences in dose response were evident both at week 3 and week 6 bleeds. The higher dose elicited high-titered antibody response. Aluminum adjuvant elicited substantially higher antibody response at week 3 at both dose levels (0.1 and 1 µg) as compared to the unadjuvanted groups. After secondary immunization, conjugates given at 1 µg dose elicited 5 to 10 fold increase in antibody levels. At this dose level peptide conjugates with 3 and 5 repeats induced higher antibody response than a single repeat containing conjugate. The titers against the CRM carrier were also determined, and these are listed in Table 11.

TABLE 11

Anti-CRM Endpoint Titers for Multiple Antigenic Peptide (MAP) Conjugates

| Group Code | Sample Description | Adjuvant | Wk 0 Pool | Wk 3 GMT | Wk 6 GMT |
|---|---|---|---|---|---|
| AG332 | 1 μg Aβ (1-7)$_1$/CRM | Al(OH)$_3$ | <50 | 10,531 | 114,602 |
| AG333 | 1 μg Aβ (1-7)$_3$/CRM | Al(OH)$_3$ | <50 | 4,274 | 83,065 |
| AG334 | 1 μg Aβ (1-7)$_5$/CRM | Al(OH)$_3$ | <50 | 1,680 | 49,320 |
| AG335 | 0.1 μg Aβ (1-7)$_1$/CRM | Al(OH)$_3$ | <50 | 1,114 | 13,231 |
| AG336 | 0.1 μg Aβ (1-7)$_3$/CRM | Al(OH)$_3$ | <50 | 197 | 1,484 |
| AG337 | 0.1 μg Aβ (1-7)$_5$/CRM | Al(OH)$_3$ | <50 | 65 | 222 |
| AG338 | 1 μg Aβ (1-7)$_1$/CRM | None | <50 | 35 | 309 |
| AG339 | 1 μg Aβ (1-7)$_3$/CRM | None | <50 | 29 | 1,085 |
| AG340 | 1 μg Aβ (1-7)$_5$/CRM | None | <50 | 29 | 542 |
| AG341 | 0.1 μg Aβ (1-7)$_1$/CRM | None | <50 | 25 | 55 |
| AG342 | 0.1 μg Aβ (1-7)$_3$/CRM | None | <50 | 25 | 34 |
| AG343 | 0.1 μg Aβ (1-7)$_5$/CRM | None | <50 | 29 | ND |

Animals were immunized at weeks 0 and 3 and bled at weeks 0, 3, and 6.
Adjuvant: 100 μg Al(OH)$_3$ or none.
ND = Not Determined.

Data in Table 11 indicates that the unadjuvanted groups induced very low levels of anti-CRM antibody response at both 1 μg as well as 0.1 μg dose levels even after two immunizations. However conjugates with aluminum hydroxide adjuvant induced substantial levels of anti-CRM antibody response at 1 μg dose and much lower response at 0.1 μg dose. In the presence of the adjuvant, CRM titers were highest for the single repeat conjugate, intermediate for the triple repeat conjugate, and lowest for the quintuple repeat conjugate. This is as expected, since the CRM dose per peptide dose is lowest for Aβ(1-7)$_5$/CRM, and highest for Aβ(1-7)$_1$/CRM. The differences were only statistically significant at week 6 for the 0.1μ μg dose.

The objective of the current invention is to elicit high titered immunogenic response against the antigenic hapten and not necessarily against the carrier protein. Under certain circumstances it is desirable to elicit optimal immune response against the hapten antigenic determinant with least or no immune response against the carrier protein. For such applications, conjugates with tandem repeats of multiple antigenic determinants with unadjuvanted formulation will serve the need.

Example 9

Preparation of Aβ-Peptide Conjugates with Various Carrier Proteins and their Immunogenicity This example compares the immunogenicity of conjugates using six different carrier proteins. The acetate salt of Aβ1-7 was added to bromoacetylated carriers in a 1:1 ratio by weight at pH 9. All conjugates except Aβ1-7/rC5ap were capped with N-acetylcysteamine. All of the alternative carriers are recombinant bacterial proteins, including CRM (diphtheria toxoid), recombinant C5a peptidase (rC5ap; cloned from *Streptococcus agalactiae*, includes D130A and S512A mutations), ORFS1224, 1664, 2452 (all cloned from *Streptococcus pyogenes*), and T367, T858 (each cloned from *Chlamydia pneumoniae*). A summary of the carriers used is found in Table 12. The degree of conjugation and capping of each Aβ 1-7 conjugate to these carriers are presented in Table 13.

This study showed that the recombinant C5a peptidase conjugate induced higher titers against Aβ than most of the other carriers tested, including CRM. This difference was statistically significant for week 6 titers of groups that received aluminum hydroxide. In addition, the Aβ1-7/T858 conjugate was significantly more immunogenic than most other conjugates in the absence of adjuvant. The only conjugate that performed poorly relative to the CRM control conjugate was Aβ1-7/T367, a conjugate that also did not react with an Aβ specific monoclonal antibody by Western blot. This study confirms that numerous other carriers can be successfully used to immunize against the Aβ peptide.

TABLE 12

List of Carriers and Conjugate Properties

| CARRIER PROTEIN | MW of carrier (Da) | # of lysines |
|---|---|---|
| CRM | 58,408 | 39 |
| rC5ap | 108,560 | 85 |
| ORF1224 | 30,950 | 18 |
| ORF1664 | 31,270 | 38 |
| ORF2452 | 31,790 | 29 |
| T367 | 49,700 | 29 |
| T858 | 37,190 | 23 |

TABLE 13

Degree Of Conjugation and Capping of Each Conjugate

| CONJUGATE | Peptide load (CMC) | Capping (CMCA) |
|---|---|---|
| Aβ1-7/rC5ap | 25.9 | — |
| Aβ1-7/ORF1224 | 12.8 | 5.7 |
| Aβ1-7/ORF1664 | 13.4 | 10.8 |
| Aβ1-7/ORF2452 | 12.03 | 10.5 |
| Aβ1-7/T367 | 13.2 | 8.2 |
| Aβ1-7/T858 | 5.2 | 1.7 |

Conjugation results: Peptide load (the average number of Aβ1-7 peptides per carrier) and capping number are the numbers of unique amino acids (CMC or CMCA) per carrier as determined by amino acid analysis. The CMC and CMCA values were referenced to lysine.

Immunization Results

The geometric mean titer for each group in this study is listed in Table 14. At week 3, regardless of the presence of adjuvant, Aβ1-7/rC5ap induced significantly higher anti-Aβ titers than the corresponding conjugates prepared with *Streptococcus pyogenes* ORFs 1224, 1664, 2452, or *Chlamydia pneumoniae* ORFs T367 and T858. At week 3 in the absence of adjuvant, Aβ1-7/rC5ap was also more immunogenic than all other conjugates except Aβ1-7/T858. The T858 conjugate without Al(OH)$_3$ induced higher titers than the ORF1224, ORF1664, ORF2452, and CRM conjugates without adjuvant. The only conjugate that was significantly less immunogenic than Aβ1-7/CRM was Aβ1-7/T367 (p<0.00002). The T367 carrier performed poorly with or without adjuvant at both weeks 3 and 6. At week 6, the rC5ap conjugate with aluminum hydroxide was more immunogenic (p<0.04) than all the other conjugates except Aβ1-7/ORF2452. In the absence of adjuvant, both Aβ1-7/rC5ap and Aβ1-7/T858 induced significantly higher titers than the ORF1224, ORF1664, or T367 conjugates. Aβ1-7/CRM without aluminum hydroxide induced higher titers than either Aβ1-7/ORF1664 or Aβ1-7/T367.

TABLE 14

Anti-Aβ1-42 Endpoint Titers.

| GROUP CODE | SAMPLE DESCRIPTION | ADJUVANT | WK 0 POOL | WK 3 GMT | WK 6 GMT |
|---|---|---|---|---|---|
| AG344 | 5 μg Aβ1-7/CRM | Al(OH)$_3$ | <100 | 21,404 | 54,157 |
| AG345 | 5 μg Aβ1-7/rC5ap | Al(OH)$_3$ | <100 | 61,967 | 402,972 |
| AG346 | 5 μg Aβ1-7/ORF1224 | Al(OH)$_3$ | <100 | 10,711 | 30,084 |
| AG347 | 5 μg Aβ1-7/ORF1664 | Al(OH)$_3$ | <100 | 7,188 | 43,226 |
| AG348 | 5 μg Aβ1-7/ORF2452 | Al(OH)$_3$ | <100 | 11,437 | 109,091 |
| AG349 | 5 μg Aβ1-7/T367 | Al(OH)$_3$ | <100 | 321 | 5,139 |
| AG350 | 5 μg Aβ1-7/T858 | Al(OH)$_3$ | <100 | 16,656 | 33,328 |
| AG351 | 5 μg Aβ1-7/CRM | None | <100 | 2,615 | 119,488 |
| AG352 | 5 μg Aβ1-7/rC5ap | None | <100 | 11,858 | 279,113 |
| AG353 | 5 μg Aβ1-7/ORF1224 | None | <100 | 1,674 | 18,719 |
| AG354 | 5 μg Aβ1-7/ORF1664 | None | <100 | 119 | 9,832 |
| AG355 | 5 μg Aβ1-7/ORF2452 | None | <100 | 2,493 | 76,038 |
| AG356 | 5 μg Aβ1-7/T367 | None | <100 | 50 | 620 |
| AG357 | 5 μg Aβ1-7/T858 | None | <100 | 28,820 | 275,202 |

Animals were immunized at weeks 0 and 3 and bled at weeks 0, 3, and 6. Dose is based on the total amount of conjugate.
Adjuvant: 100 μg Al(OH)$_3$ or none.

Example 10

Preparation of Additional Aβ Peptide-Protein Conjugates

I. Activation

Thawed CRM$_{197}$ (8 mL, 59.84 mg, at 7.48 mg/mL) was dissolved in 0.1 M borate buffer (pH 9, 3.968 mL) to bring the concentration to 5 mg/mL. The solution was cooled in an ice bath to 0-5° C. Bromoacetic acid N-hydroxysuccinimide (59.9 mg) (Aldrich-Sigma) was dissolved in DMF (100 μL) (Aldrich-Sigma) and added dropwise, to the solution of CRM$_{197}$. Upon addition of the bromoacetic acid N-hydroxysuccinimide, a precipitate was observed. When the pH was checked, it decreased to pH 6. The pH of the reaction mixture was brought back to pH 9 by adding more 0.1 M borate buffer. Reaction mixture was then stirred at 4° C. for 1 hr, with gentle swirling. The mixture was purified and concentrated using YM-10 centriprep centrifugal concentration and repurified on Sephadex G-25 using 10 mM borate as the eluent. Fractions positive to Bradford Reagent were pooled and concentrated using centriprep YM-10. The degree of bromoacetylation was determined by Bradford assay (linear). The concentration was found to be 5.36 mg/mL (Yielded 30 mg). The final concentration was then adjusted to be 5 mg/mL and was stored in the freezer in 5% sucrose until further use.

II. Conjugation

For each conjugation, thawed bromoacetylated CRM$_{197}$ was used. Peptides were dissolved in borate buffer (2.5 mg in 125 ml of 0.1 M borate buffer). Slight insolubility was observed with Aβ peptides KLVFFAEDC (SEQ ID NO:45), CLVFFAEDV (SEQ ID NO:47), CKLVFFAED (SEQ ID NO:48), and LVFFAEDC (SEQ ID NO:50). Bromoacetylated CRM$_{197}$ (5 mg/mL) was treated with the peptide solutions/suspensions. The ratio of the peptide and protein in the mixture was 1:2. Turbidity was observed in the conjugate mixtures with peptides KLVFFAEDC (SEQ ID NO:45), CLVFFAEDV (SEQ ID NO:47), CKLVFFAED (SEQ ID NO:48), and KLVFFAEDC (SEQ ID NO:45). The mixtures were then checked for pH (pH 9) and incubated at 4° C. overnight with slow swirling. Final concentrations of the mixtures were made to 3 mg/mL before incubation. The turbidity of the conjugate mixtures with peptides CLVFFAEDV (SEQ ID NO:47) and LVFFAEDC (SEQ ID NO:50) disappeared after incubation. However, KLVFFAEDC (SEQ ID NO:45) and CKLVFFAED (SEQ ID NO:48) were still slightly turbid. Soluble mock protein conjugate was also prepared with cysteamine at a ratio of 1:1 (w/w). Synthesized peptides were obtained from BIOSOURCE with about 95% purity.

```
Octamers:
LVFFAEDVC           (SEQ ID NO: 44)

KLVFFAEDC           (SEQ ID NO: 45)

VFFAEDVGC           (SEQ ID NO: 43)

CLVFFAEDV           (SEQ ID NO: 47)

CKLVFFAED           (SEQ ID NO: 48)

CVFFAEDVG           (SEQ ID NO: 46)

Heptamers:
VFFAEDVC            (SEQ ID NO: 49)

LVFFAEDC            (SEQ ID NO: 50)
```

III. Capping Unreacted Lysine Groups on Protein:

The unreacted lysines were capped with N-acetylcysteamine (CMCA; Aldrich-Sigma) at a ratio of 1/1 (w/w) for 4 hr at 4° C. while swirling in the dark. The unreacted peptides and capping reagents were removed from the conjugates by dialysis using Slide-A-Lyzer cassette (M$_w$ cut off 10,000) (Pierce) against PBS buffer (2 L) overnight (13 hr). Buffer exchange and dialysis was done twice (2×14 hr). Slight insolubility was observed in the conjugates with peptides KLVFFAEDC (SEQ ID NO:45) and CKLVFFAED (SEQ ID NO:48). All conjugates were then stored in the refrigerator at 4° C. in a perservative.

IV. Characterization of the Protein Carrier:

MALDI-TOF MS was used to determine the mass of bromoacetylated CRM$_{197}$ and the mass of the mock conjugate N-acetylcysteamine-CRM$_{197}$. Based on the masses of the CRM$_{197}$ and bromoacetylated CRM$_{197}$, 11 lysine residues were modified.

(59941.46−58590.29)/122=11

Where;
Mw of CRM$_{197}$ is 58624.29
Mw of bromoacetylated CRM$_{197}$ is 59941.46
Mw of bromoacetate is 122

The degree of bromoacetylation was more than 28%. (The total number of lysines in CRM$_{197}$ was 39). From these 11 modified lysine residues, 10 were coupled with cysteamine. The coupling efficiency was 90%.

(61143−59941)/119=10

Where;
Mw of bromoacetylated CRM$_{197}$ is 59941.46
Mw of mock conjugate is 61143
Mw of the N-acetylcysteamine is 119

(10/11)×100=90

Figure 10:
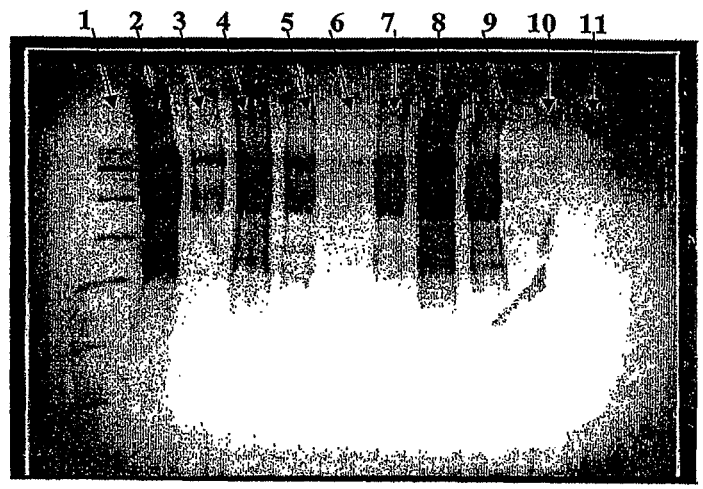
FIG. 10: Peptide-protein conjugates were characterized using SDS-PAGE Western blot analysis with a tris-tricine precast gel. The lanes are: marker (lane 1); L-28375 24/01 (lane 2); L-28375 24/02 (lane 3); L-28375 24/03 (lane 4); L-28375 24/04 (lane 5); L-28375 24/05 (lane 6); L-28375 24/06 (lane 7) L-28375 24/07 (lane 8); L-28375 24/08 (lane 9); L-28375 24/09 (Mock) (lane 10); and, BrAcCRM$_{197}$ (lane 11).

V. Characterization of the Peptide-Protein Conjugates by SDS-PAGE Western Blot Analysis with Tris-Tricine Precast Gel:

The protein-peptide conjugates were analyzed by Western blot. The lanes are: marker (lane 1); L-28375 24/01 (lane 2); L-28375 24/02 (lane 3); L-28375 24/03 (lane 4); L-28375 24/04 (lane 5); L-28375 24/05 (lane 6); L-28375 24/06 (lane 7) L-28375 24/07 (lane 8); L-28375 24/08 (lane 9); L-28375 24/09 (Mock) (lane 10); and, BrAcCRM$_{197}$ (lane 11). A peptide specific monoclonal antibody from mice (248-6H9-806 Aβ 17-28) was used as the primary antibody (antisera) (1:3000 dilution was found to be the best). Goat-Anti mouse IgG (H+L)-HPR was the secondary antibody (1:1000 dilution). It was observed that all the conjugates were recognized by the primary antibody, except for the mock conjugate and the activated CRM$_{197}$. (See FIG. 10.)

Protein Concentration

Protein concentrations of the conjugate samples were determined by the Pierce BCA assay. (See Table 15.)

Amino Acid Analysis

Amino acid analysis was carried out to determine the degree of conjugation. T degree of conjugation was calculated based on the CMCA (carboxymethylcycteamine) residues found in the conjugates. CMCA was used to cap the unreacted activated sites after conjugation with the peptides. (See Table 15.)

TABLE 15

Degree of Conjugation of Peptides with BrAcCRM$_{197}$

| Conjugate Code | Peptide Sequence (SEQ ID NO:) | Final Concentration (mg/mL) | Degree of Conjugation (Based on CMCA) |
|---|---|---|---|
| L-28375 24/01 | LVFFAEDV-C (SEQ ID NO: 44) | 1.67 | 8/10 |
| L-28375 24/02 | KLVFFAED-C (SEQ ID NO: 45) | 0.82 | 5/10 |
| L-28375 24/03 | VFFAEDVG-C (SEQ ID NO: 43) | 1.43 | 8/10 |
| L-28375 24/04 | C-LVFFAEDV (SEQ ID NO: 47) | 1.04 | 9/10 |
| L-28375 24/05 | C-KLVFFAED (SEQ ID NO: 48) | 0.78 | 1/10 |
| L-28375 24/06 | C-VFFAEDVG (SEQ ID NO: 46) | 0.97 | 9/10 |
| L-28375 24/07 | VFFAEDV-C (SEQ ID NO: 49) | 1.00 | 7/10 |
| L-28375 24/08 | LVFFAED-C (SEQ ID NO: 50) | 0.99 | 8/10 |
| L-28375 24/09 (Mock) | | 1.89 | 10/11 |

All colorimetric assays were performed using microplate spectrophotometer and SOFTmax Pro.

Example 11

Immunogenic Studies of Aβ Peptide Conjugates in Swiss Webster Mice

Outbred Swiss Webster mice were immunized with VFFAEDVG-C (SEQ ID NO:43), LVFFAEDV-C (SEQ ID NO:44), KLVFFAED-C (SEQ ID NO:45), C-VFFAEDVG (SEQ ID NO:46), C-LVFFAEDV (SEQ ID NO:47), C-KLVFFAED (SEQ ID NO:48), VFFAEDV-C (SEQ ID NO:49), LVFFAED-C (SEQ ID NO:50) each conjugated to CRM$_{197}$, or with Aβ1-7CRM$_{197}$, all formulated with the adjuvant RC 529 SE. Nine groups of 10 animals per group were immunized subcutaneously with one of the Aβ peptide conjugates at the beginning of the study (week 0) and subsequently at week 4. Serum was collected prior to, but on the same days as immunization.

Immunogenic Studies of Aβ Peptide Conjugates in Inbred Balb/c Mice

Inbred Balb/c mice were immunized as in the preceding paragraph, but were also boosted with conjugate and adjuvant at week 12.

Results

Sera from both studies are being collected for analysis of Aβ$_{13-28}$ peptide-specific IgG antibody titer. Sera from Balb/c mice are also collected for analysis one day prior to the week 12 boost, and one week thereafter. Spleen cells from animals used in Example 11 are evaluated for their potential to respond in-vitro to stimulation with an overlapping pool of peptides spanning Aβ$_{1-42}$, full length Aβ$_{1-42}$, CRM$_{197}$, or polyclonal activators. Analysis is comprised of Elispot readout for interleukins 4 and 5, and interferon-gamma. Upon completion, the Aβ peptide conjugates are be evaluated as described above and as described in Example 6.

Example 12

Immunogenic Studies of Aβ Peptide Conjugates in PSAPP Mice

PSAPP mice are immunized with VFFAEDVG-C (SEQ ID NO:43), LVFFAEDV-C (SEQ ID NO:44), KLVFFAED-C (SEQ ID NO:45), C-VFFAEDVG (SEQ ID NO:46), C-LVFFAEDV (SEQ ID NO:47), C-KLVFFAED (SEQ ID NO:48), VFFAEDV-C (SEQ ID NO:49), LVFFAED-C (SEQ ID NO:50). The PSAPP mouse, a doubly transgenic mouse (PSAPP) overexpressing mutant APP and PS1 transgenes, is described in Holcomb, et al. (1998) *Nature Medicine* 4:97-11.

Immunogenic Studies of Aβ Peptide Conjugates in PDAPP Mice

PDAPP mice are immunized with VFFAEDVG-C (SEQ ID NO:43), LVFFAEDV-C (SEQ ID NO:44), KLVFFAED-C (SEQ ID NO:45), C-VFFAEDVG (SEQ ID NO:46), C-LVFFAEDV (SEQ ID NO:47), C-KLVFFAED (SEQ ID NO:48), VFFAEDV-C (SEQ ID NO:49), LVFFAED-C (SEQ ID NO:50) The PDAPP mouse expresses a mutant form of human APP (APP$^{V71F}$) and develops Alzheimer's disease at a young age (Bard, et al. (2000) *Nature Medicine* 6:916-919; Masliah E, et al. (1996) *J. Neurosci.* 15; 16(18):5795-811).

Results

Sera from both studies are collected for analysis of Aβ$_{13-28}$ peptide-specific IgG antibody titer. Upon completion, the Aβ peptide conjugates will be evaluated as described above and as described in Examples 6 and 11, as well as in the contextual fear conditioning (CFC) assay.

Contextual fear conditioning is a common form of learning that is exceptionally reliable and rapidly acquired in most animals, for example, mammals. Test animals learn to fear a previously neutral stimulus and/or environment because of its association with an aversive experience. (see, e.g., Fanselow, *Anim. Learn. Behav.* 18:264-270 (1990); Wehner et al., *Nature Genet.* 17:331-334. (1997); Caldarone et al., *Nature Genet.* 17:335-337 (1997)).

Contextual fear conditioning is especially useful for determining cognitive function or dysfunction, e.g., as a result of disease or a disorder, such as a neurodegenerative disease or disorder, an Aβ-related disease or disorder, an amyloidogenic disease or disorder, the presence of an unfavorable genetic alteration effecting cognitive function (e.g., genetic mutation, gene disruption, or undesired genotype), and/or the efficacy of an agent, e.g., an Aβ conjugate agent, on cognitive ability. Accordingly, the CFC assay provides a method for independently testing and/or validating the therapeutic effect of agents for preventing or treating a cognitive disease or disorder, and in particular, a disease or disorder affecting one or more regions of the brains, e.g., the hippocampus, subiculum, cingulated cortex, prefrontal cortex, perirhinal cortex, sensory cortex, and medial temporal lobe.

Typically, the CFC assay is performed using standard animal chambers and the employment of conditioning training comprising a mild shock (e.g., 0.35 mA foot shock) paired with an auditory (e.g., a period of 85 db white noise), olfactory (e.g., almond or lemon extract), touch (e.g., floor cage texture), and/or visual cue (light flash). The response to the aversive experience (shock) is typically one of freezing (absence of movement except for respiration) but may also include eye blink, or change in the nictitating membrane reflex, depending on the test animal selected. The aversive response is usually characterized on the first day of training to determine a baseline for unconditioned fear, with aversive response results on subsequent test days, e.g., freezing in presence of the context and/or cue but in the absence of the aversive experience, being characterized as context and cue conditioned fear, respectively. For improved reliability, test animals are typically tested separately by independent technicians and scored over time. Additional experimental design details can be found in the art, for example, in Crawley, J N, *What's Wrong with my Mouse; Behavioral Phenotyping of Transgenic and Knockout Mice*, Wiley-Liss, NY (2000).

Exemplary test animals (e.g., model animals) include mammals (e.g. rodents or non-human primates) that exhibit prominent symptoms or pathology that is characteristic of an amyloidogenic disorder such as Alzheimer's. Model animals may be created by selective inbreeding for a desired or they may genetically engineered using transgenic techniques that are well-known in the art, such that a targeted genetic alteration (e.g. a genetic mutation, gene disruption) in a gene that is associated with the dementia disorder, leading to aberrant expression or function of the targeted gene. For example, several transgenic mouse strains are available that overexpress APP and develop amyloid plaque pathology and/or develop cognitive deficits that are characteristic of Alzheimer's disease (see for example, Games et al., supra, Johnson-Wood et al., *Proc. Natl. Acad. Sci. USA* 94:1550 (1997); Masliah E and Rockenstein E. (2000) *J Neural Transm Suppl.;* 59:175-83).

Alternatively, the model animal can be created using chemical compounds (e.g. neurotoxins, anesthetics) or surgical techniques (e.g. stereotactic ablation, axotomization, transection, aspiration) that ablate or otherwise interfere with the normal function of an anatomical brain region (e.g. hippocampus, amygdala, perirhinal cortex, medial septal nucleus, locus coeruleus, mammalary bodies) or specific neurons (e.g. serotonergic, cholinergic, or dopaminergic neurons) that are associated with characteristic symptoms or pathology of the amyloidogenic disorder. In certain preferred embodiments, the animal model exhibits a prominent cognitive deficit associated with learning or memory in addition to the neurodegenerative pathology that associated with a amyloidogenic disorder. More preferably, the cognitive deficit progressively worsens with increasing age, such that the disease progression in the model animal parallels the disease progression in a subject suffering from the amyloidogenic disorder.

Contextual fear conditioning and other in vivo assays to test the functionality of the conjugates described herein may be performed using wild-type mice or mice having a certain genetic alteration leading to impaired memory or mouse models of neurodegenerative disease, e.g., Alzheimer's disease, including mouse models which display elevated levels of soluble Aβ in the cerebrospinal fluid (CSF) or plasma. For example, animal models for Alzheimer's disease include transgenic mice that overexpress the "Swedish" mutation of human amyloid precursor protein (hAPP swe; Tg2576) which show age-dependent memory deficits and plaques (Hsiao et al. (1996) *Science* 274:99-102). The in vivo functionality of the conjugates described herein can also be tested using the PS-1 mutant mouse, described in Duff, et al. (1996) *Nature* 383, 710-713. Other genetically altered transgenic models of Alzheimer's disease are described in Masliah E and Rockenstein E. (2000) *J Neural Transm Suppl.* 59:175-83.

In various aspects, the methods of the invention comprise the administration of an Aβ conjugate, that is capable of improving cognition in a subject wherein the Aβ conjugate has been identified in using an assay which is suitably predictive of immunotherapeutic efficacy in the subject. In exemplary embodiments, the assay is a model animal assay that is based, at least in part, on comparing cognition, as determined from a contextual fear conditioning study, of an animal after administration of a test immunological reagent to the animal, as compared to a suitable control. The CFC assay evaluates changes in cognition of an animal (typically a mouse or rat) upon treatment with a potential therapeutic compound. In certain embodiments, the change in cognition evaluated is an improvement in memory impairment status or a reversal of memory deficit. Accordingly, the CFC assay provides a direct method for determining the therapeutic effect of agents for preventing or treating cognitive disease, and in particular, a disease or disorder affecting one or more regions of the brains, e.g., the hippocampus, subiculum, cingulated cortex, prefrontal cortex, perirhinal cortex, sensory cortex, and medial temporal lobe. Such CFC assays are discussed in copending U.S. Patent Application Ser. No. 60/636,842 entitled "Contextual Fear Conditioning for Predicting Immunotherapeutic Efficacy", filed on Dec. 15, 2004, and U.S. Patent Application Ser. No. 60/637,253 entitled "Contextual Fear Conditioning for Predicting Immunotherapeutic Efficacy" the entire contents of which are hereby incorporated by reference.

What is claimed is:

1. A method of producing an immunogenic conjugate, the method comprising the steps of:
   (a) derivatizing one or more functional groups of a carrier protein to generate an activated functional group on the carrier protein;
   (b) reacting a peptide immunogen comprising an Aβ fragment with the carrier protein of step (a) under conditions to form a conjugate, wherein the Aβ fragment comprises residues 16-23 of Aβ (SEQ ID NO:21) and the peptide immunogen is covalently attached to the activated functional group on the carrier protein; and
   (c) further reacting the conjugate of step (b) with N-acetylcysteamine to inactivate any remaining activated functional group on the carrier protein to generate the immunogenic conjugate, wherein a capping molecule, formed by reaction of the conjugate with the N-acetyl-cysteamine, is covalently attached to the remaining activated functional group on the carrier protein, wherein the immunogenic conjugate has the formula:

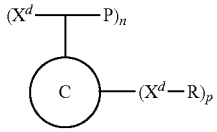

wherein,

C is a $CRM_{197}$ carrier protein, $X^d$ is a derivatized functional group of an amino acid residue of the carrier protein, P is the peptide immunogen comprising the Aβ fragment covalently attached to the derivatized functional group of the amino acid residue of the carrier protein, R is the capping molecule covalently attached to the derivatized functional group of an amino acid residue of the carrier protein, wherein the functionality of the carrier protein is preserved such that it retains its ability to elicit the desired immune response against the peptide immunogen that would otherwise not occur without a carrier, n is an integer greater than 0, but less than or equal to 38, and p is an integer greater than 0, but less than or equal to 38.

2. The method of claim 1, further comprising a step of introducing a reactive group into the peptide immunogen before step (b).

3. The method of claim 2, wherein the step of introducing the reactive group into the peptide immunogen comprises adding an amino acid residue having the reactive group.

4. The method of claim 3, wherein the amino acid residue is a cysteine residue in which the reactive group comprises —SH, or the amino acid residue is an arginine residue and the reactive group comprises a guanidyl group, or the amino acid residue is a glutamate or aspartate residue and the reactive group comprises —COOH, or the amino acid residue is a lysine residue and the reactive group comprises —NH₂.

5. The method of claim 4, wherein the reactive group introduced into the peptide immunogen comprises a —SH of a cysteine residue, and wherein the cysteine residue is introduced into the peptide immunogen during peptide synthesis.

6. The method of claim 5, wherein the cysteine residue is added to the carboxy-terminus of the peptide immunogen.

7. The method of claim 5, wherein the cysteine residue is added to the amino-terminus of the peptide immunogen.

8. The method of claim 5, wherein the peptide immunogen further comprises a peptide linker disposed between the Aβ fragment and the cysteine residue.

9. The method of claim 2, wherein the step of introducing the reactive group into the peptide immunogen comprises generating a pendant thiol group on an amino acid residue susceptible to such modification via a thiolating reagent.

10. The method of claim 9, wherein the thiolating reagent is N-acetylhomocysteine thiolactone.

11. The method of claim 9, wherein the amino acid residue is localized at the amino-terminus of the peptide immunogen or at carboxy-terminus of the peptide immunogen.

12. The method of claim 1, wherein the immunogenic conjugate comprises from 5 to 25 peptide immunogens covalently attached to the carrier protein.

13. The method of claim 12, wherein the immunogenic conjugate comprises from 12 to 20 peptide immunogens covalently attached to the carrier protein.

14. The method of claim 13, wherein the immunogenic conjugate comprises from 12 to 15 peptide immunogens covalently attached to the carrier protein.

15. The method of claim 6, wherein the peptide immunogen is KLVFFAED-C(SEQ ID NO:45).

16. A method of producing an immunogenic conjugate, the method comprising:

(a) derivatizing one or more lysine residues of a $CRM_{197}$ carrier protein to generate an activated functional group on the carrier protein;

(b) reacting a peptide immunogen comprising residues 16-23 of Aβ (SEQ ID NO:21) and a C-terminal cysteine residue with the carrier protein of step (a) under conditions to form a conjugate; and (c) further reacting the conjugate of step (b) with N-acetylcysteamine to inactivate any remaining activated functional group on the carrier protein to generate the immunogenic conjugate, wherein the immunogenic conjugate has the formula:

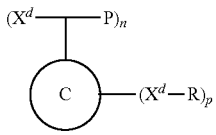

wherein,

C is $CRM_{197}$, $X^d$ is a derivatized lysine residue of $CRM_{197}$,

P is the peptide immunogen covalently attached to the derivatized lysine residue via the C-terminal cysteine residue, R is a capping molecule formed by reaction of the conjugate with N-acetylcysteamine in step (c) covalently attached to the derivatized lysine residue of $CRM_{197}$, wherein the functionality of the carrier protein is preserved such that it retains its ability to elicit the desired immune response against the peptide immunogen that would otherwise not occur without a carrier, n is an integer greater than 0, but less than or equal to 38, and p is an integer greater than 0, but less than or equal to 38.

17. The method of claim 16, wherein n is an integer greater than or equal to 5, but less than or equal to 25.

18. The method of claim 17, wherein n is an integer greater than or equal to 12, but less than or equal to 15.

19. The method of claim 18, wherein the peptide immunogen is KLVFFAED-C(SEQ ID NO:45).

20. The method of claim 16, wherein the immunogenic conjugate has the formula:

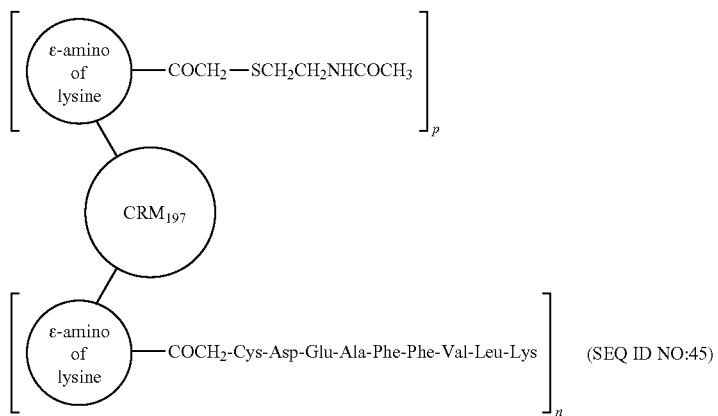
wherein,
n is an integer greater than 0, but less than or equal to 38, and
p is an integer greater than 0, but less than or equal to 38.
21. The method of claim 20, wherein n plus p equals from 20 to 22.
* * * * *